US012736542B2

(12) United States Patent
Lemoine et al.

(10) Patent No.: US 12,736,542 B2
(45) Date of Patent: Sep. 15, 2026

(54) IDENTIFICATION OF MICROORGANISMS BASED ON IDENTIFICATION OF PEPTIDES USING A LIQUID SEPARATION DEVICE COUPLED WITH A MASS SPECTROMETER AND PROCESSING MEANS

(71) Applicants: Université Claude Bernard Lyon 1, Villeurbanne (FR); Centre National de la Recherche Scientifique (CNRS), Paris (FR); Institut National de la Santé et de la Recherche Médicale (INSERM), Paris (FR); Ecole Normale Superieure de Lyon, Lyons (FR); Hospices Civils de Lyon, Lyons (FR)

(72) Inventors: Jérôme Lemoine, Lucenay (FR); Maud Gregson, Lyons (FR); Julie Gil, Venissieux (FR); Romain Carriere, Farnay (FR); François Vandenesch, Rillieux-la-Pape (FR)

(73) Assignees: Université Claude Bernard Lyon 1, Villeurbanne (FR); Centre National de la Recherche Scientifique (CNRS), Paris (FR); Institut National de la Santé et de la Recherche Médicale (INSERM), Paris (FR); Ecole Normale Superieure de Lyon, Lyons (FR); Hospices Civils de Lyon, Lyons (FR)

( * ) Notice: Subject to any disclaimer, the term of this patent is extended or adjusted under 35 U.S.C. 154(b) by 330 days.

(21) Appl. No.: 18/578,465

(22) PCT Filed: Jul. 15, 2022

(86) PCT No.: PCT/EP2022/069857
§ 371 (c)(1),
(2) Date: Jan. 11, 2024

(87) PCT Pub. No.: WO2023/285653
PCT Pub. Date: Jan. 19, 2023

(65) Prior Publication Data

US 2025/0003980 A1 Jan. 2, 2025

(30) Foreign Application Priority Data

Jul. 15, 2021 (EP) .................................... 21305988

(51) Int. Cl.
*G01N 33/68* (2006.01)
*G01N 30/72* (2006.01)
(Continued)

(52) U.S. Cl.
CPC ..... *G01N 33/6848* (2013.01); *G01N 30/7233* (2013.01); *G01N 30/8624* (2013.01);
(Continued)

(58) Field of Classification Search
None
See application file for complete search history.

(56) References Cited

U.S. PATENT DOCUMENTS 8,620,595 B2 12/2013 Krokhin et al.
2007/0006950 A1 1/2007 Okada et al.
2019/0371586 A1* 12/2019 Lemoine ................ G01N 30/86

FOREIGN PATENT DOCUMENTS

EP 3384517 B1 10/2018
WO WO-2005015209 A2 * 2/2005 ......... G01N 30/8675
(Continued)

OTHER PUBLICATIONS

Blumenscheit et al., *Unbiased antimicrobial resistance detection from clinical bacterial isolates using proteomics*, BIORXIV (Dec. 10, 2020).

(Continued)

*Primary Examiner* — Yung-Sheng M Tsui
(74) *Attorney, Agent, or Firm* — Panitch Schwarze Belisario & Nadel LLP; Erin M. Dunston

(57) ABSTRACT

Identification of at least one microorganism present in a sample based on the detection of peptides issued from the
(Continued)

cleavage of ribosomal proteins of said microorganism, comprising lysis of microorganism(s) and cleavage of the proteins, obtaining a mixture of peptides, decomplexing the peptide mixture using a liquid separation device coupled with a mass spectrometer, nebulizing the liquid to produce an ion current, receiving the ion current from the ion source, executing on the ion current a series of filtering steps for detecting a transition, receiving data on the transitions, assigning the transitions associated with peptides into two or more contiguous groups, monitoring, and optionally generating a chromatogram or electropherogram, wherein the microorganism is identified according to the detection of said peptide(s).

12 Claims, 5 Drawing Sheets

Specification includes a Sequence Listing.

(51) Int. Cl.
*G01N 30/86* (2006.01)
*G01N 30/88* (2006.01)
*H01J 49/00* (2006.01)
*G01N 30/02* (2006.01)

(52) U.S. Cl.
CPC ............ *G01N 30/88* (2013.01); *H01J 49/004* (2013.01); *G01N 2030/027* (2013.01); *G01N 2030/8831* (2013.01)

(56) References Cited

FOREIGN PATENT DOCUMENTS

| | | | | | |
|---|---|---|---|---|---|
| WO | WO-2005098071 | A1 | | 10/2005 | |
| WO | WO-2011045544 | A2 | | 4/2011 | |
| WO | WO-2012143534 | A2 | | 10/2012 | |
| WO | WO-2012143535 | A2 | | 10/2012 | |
| WO | WO-2014116711 | A1 | * | 7/2014 | ............. G16B 40/10 |
| WO | WO-2017093861 | A1 | | 6/2017 | |
| WO | WO-2022074610 | A1 | * | 4/2022 | .......... H01J 49/0027 |
| WO | WO-2023281387 | A1 | * | 1/2023 | ............. G01N 33/94 |

OTHER PUBLICATIONS

Boulund et al., *Typing and Characterization of Bacteria Using Bottom-up Tandem Mass Spectrometry Proteomics*, 16(6) Mol. Cell Proteomics 1052-1063 (2017).
Holland et al., *Identification of bacterial proteins observed in MALDI TOF mass spectra from whole cells*, 71 Analytical Chemistry 3226-3230 (1999).
Lasch et al., *Identification of Microorganisms by Liquid Chromatography-Mass Spectrometry (LC-MS[1]) and in Silico Peptide Mass Libraries*, 19(12) Mol. Cell Proteomics 2125-2139 (2020).
Roux-Dalvai et al., *Fast and Accurate Bacterial Species Identification in Urine Specimens Using LC-MS/MS Mass Spectrometry and Machine Learning*, 18 Molecular & Cellular Proteomics 2492-2505 (2019).
Rougemont et al., *Scout-MRM: Multiplexed Targeted Mass Spectrometry-Based Assay without Retention Time Scheduling Exemplified by* Dickeya dadantii *Proteomic Analysis during Plant Infection*, 89 Anal. Chem. 1421-1426 (2017).
Suarez et al., *Ribosomal proteins as biomarkers for bacterial identification by mass spectrometry in the clinical microbiology laboratory*, 94(3) J. Microbiol. Methods 390-396 (Sep. 2013).
Charretier et al. Rapid Bacterial Identification, Resistance, Virulence and Type Profiling using Selected Reaction Monitoring Mass Spectrometry, 5(13944) Scientific Reports 1-11 (2014).
Karlsson et al., Discovery of Species-unique Peptide Biomarkers of Bacterial Pathogens by Tandem Mass Spectrometry-based Proteotyping, 19 Molecular & Cellular Proteomics 518-528 (2020).
Japanese Office Action in counterpart Japanese Patent Application No. 2024-501945, with English translation (mailed on Jun. 8, 2026).

* cited by examiner

SEQUENCE LISTING

```
Sequence total quantity: 428
SEQ ID NO: 1            moltype = AA  length = 10
FEATURE                 Location/Qualifiers
source                  1..10
                        mol_type = protein
                        organism = Abiotrophia defectiva
SEQUENCE: 1
SDEEAHALLK                                                              10

SEQ ID NO: 2            moltype = AA  length = 11
FEATURE                 Location/Qualifiers
source                  1..11
                        mol_type = protein
                        organism = Abiotrophia defectiva
SEQUENCE: 2
GAMVLPHGTG K                                                            11

SEQ ID NO: 3            moltype = AA  length = 11
FEATURE                 Location/Qualifiers
source                  1..11
                        mol_type = protein
                        organism = Abiotrophia defectiva
SEQUENCE: 3
GSEAVSLTVN R                                                            11

SEQ ID NO: 4            moltype = AA  length = 10
FEATURE                 Location/Qualifiers
source                  1..10
                        mol_type = protein
                        organism = Abiotrophia defectiva
SEQUENCE: 4
FVDQMITLGK                                                              10

SEQ ID NO: 5            moltype = AA  length = 19
FEATURE                 Location/Qualifiers
source                  1..19
                        mol_type = protein
                        organism = Abiotrophia defectiva
SEQUENCE: 5
AAALANLVEG SIVEGTVAR                                                    19

SEQ ID NO: 6            moltype = AA  length = 12
FEATURE                 Location/Qualifiers
source                  1..12
                        mol_type = protein
                        organism = Abiotrophia defectiva
SEQUENCE: 6
EYAVVNLEAL NR                                                           12

SEQ ID NO: 7            moltype = AA  length = 12
FEATURE                 Location/Qualifiers
source                  1..12
                        mol_type = protein
                        organism = Abiotrophia defectiva
SEQUENCE: 7
LGFEGGQTQL FR                                                           12

SEQ ID NO: 8            moltype = AA  length = 10
FEATURE                 Location/Qualifiers
source                  1..10
                        mol_type = protein
                        organism = Abiotrophia defectiva
SEQUENCE: 8
ELDLIGVGYR                                                              10

SEQ ID NO: 9            moltype = AA  length = 13
FEATURE                 Location/Qualifiers
source                  1..13
                        mol_type = protein
                        organism = Achromobacter xylosoxidans
SEQUENCE: 9
LMQVILAPIV TEK                                                          13

SEQ ID NO: 10           moltype = AA  length = 12
FEATURE                 Location/Qualifiers
source                  1..12
                        mol_type = protein
                        organism = Achromobacter xylosoxidans
```

-continued

```
SEQUENCE: 10
VVGALGQILG PR                                                    12

SEQ ID NO: 11          moltype = AA  length = 10
FEATURE                Location/Qualifiers
source                 1..10
                       mol_type = protein
                       organism = Achromobacter xylosoxidans
SEQUENCE: 11
VIEPLITLGK                                                       10

SEQ ID NO: 12          moltype = AA  length = 14
FEATURE                Location/Qualifiers
source                 1..14
                       mol_type = protein
                       organism = Achromobacter xylosoxidans
SEQUENCE: 12
GNTGETLIQL LESR                                                  14

SEQ ID NO: 13          moltype = AA  length = 14
FEATURE                Location/Qualifiers
source                 1..14
                       mol_type = protein
                       organism = Acinetobacter baumannii
SEQUENCE: 13
ILYEIEGVNE DLAR                                                  14

SEQ ID NO: 14          moltype = AA  length = 17
FEATURE                Location/Qualifiers
source                 1..17
                       mol_type = protein
                       organism = Acinetobacter baumannii
SEQUENCE: 14
TDLPEFAPGD TVVVQVK                                               17

SEQ ID NO: 15          moltype = AA  length = 13
FEATURE                Location/Qualifiers
source                 1..13
                       mol_type = protein
                       organism = Acinetobacter baumannii
SEQUENCE: 15
ATIANVNASD EER                                                   13

SEQ ID NO: 16          moltype = AA  length = 12
FEATURE                Location/Qualifiers
source                 1..12
                       mol_type = protein
                       organism = Acinetobacter baumannii
SEQUENCE: 16
SGTTGNIEAA TK                                                    12

SEQ ID NO: 17          moltype = AA  length = 10
FEATURE                Location/Qualifiers
source                 1..10
                       mol_type = protein
                       organism = Acinetobacter baumannii
SEQUENCE: 17
STGESVAVAK                                                       10

SEQ ID NO: 18          moltype = AA  length = 8
FEATURE                Location/Qualifiers
source                 1..8
                       mol_type = protein
                       organism = Acinetobacter common
SEQUENCE: 18
TLEQYFGR                                                         8

SEQ ID NO: 19          moltype = AA  length = 12
FEATURE                Location/Qualifiers
source                 1..12
                       mol_type = protein
                       organism = Acinetobacter common
SEQUENCE: 19
QGLGIAIVST SK                                                    12

SEQ ID NO: 20          moltype = AA  length = 11
FEATURE                Location/Qualifiers
source                 1..11
                       mol_type = protein
```

```
                        organism = Acinetobacter common
SEQUENCE: 20
GGFTVDIGPV R                                                   11

SEQ ID NO: 21           moltype = AA  length = 11
FEATURE                 Location/Qualifiers
source                  1..11
                        mol_type = protein
                        organism = Acinetobacter common
SEQUENCE: 21
GIQPVSPWGQ K                                                   11

SEQ ID NO: 22           moltype = AA  length = 12
FEATURE                 Location/Qualifiers
source                  1..12
                        mol_type = protein
                        organism = Acinetobacter common
SEQUENCE: 22
VEGDIVSLET LK                                                  12

SEQ ID NO: 23           moltype = AA  length = 15
FEATURE                 Location/Qualifiers
source                  1..15
                        mol_type = protein
                        organism = Acinetobacter common
SEQUENCE: 23
AGDAAPMAYV ELVDR                                               15

SEQ ID NO: 24           moltype = AA  length = 8
FEATURE                 Location/Qualifiers
source                  1..8
                        mol_type = protein
                        organism = Acinetobacter common
SEQUENCE: 24
AALDYGLK                                                       8

SEQ ID NO: 25           moltype = AA  length = 7
FEATURE                 Location/Qualifiers
source                  1..7
                        mol_type = protein
                        organism = Acinetobacter common
SEQUENCE: 25
EISMNIK                                                        7

SEQ ID NO: 26           moltype = AA  length = 12
FEATURE                 Location/Qualifiers
source                  1..12
                        mol_type = protein
                        organism = Acinetobacter common
SEQUENCE: 26
EPDLTGADLD AR                                                  12

SEQ ID NO: 27           moltype = AA  length = 7
FEATURE                 Location/Qualifiers
source                  1..7
                        mol_type = protein
                        organism = Acinetobacter common
SEQUENCE: 27
NVMEIPR                                                        7

SEQ ID NO: 28           moltype = AA  length = 10
FEATURE                 Location/Qualifiers
source                  1..10
                        mol_type = protein
                        organism = Acinetobacter common
SEQUENCE: 28
LADEVEATLK                                                     10

SEQ ID NO: 29           moltype = AA  length = 11
FEATURE                 Location/Qualifiers
source                  1..11
                        mol_type = protein
                        organism = Acinetobacter common
SEQUENCE: 29
FNVLTSPHVN K                                                   11

SEQ ID NO: 30           moltype = AA  length = 9
FEATURE                 Location/Qualifiers
source                  1..9
```

-continued

```
                          mol_type = protein
                          organism = Acinetobacter common
SEQUENCE: 30
VNIASIQVK                                                                9

SEQ ID NO: 31             moltype = AA  length = 10
FEATURE                   Location/Qualifiers
source                    1..10
                          mol_type = protein
                          organism = Acinetobacter common
SEQUENCE: 31
LIDIVQPTDK                                                               10

SEQ ID NO: 32             moltype = AA  length = 11
FEATURE                   Location/Qualifiers
source                    1..11
                          mol_type = protein
                          organism = Acinetobacter common
SEQUENCE: 32
AFTVQGVALT K                                                             11

SEQ ID NO: 33             moltype = AA  length = 15
FEATURE                   Location/Qualifiers
source                    1..15
                          mol_type = protein
                          organism = Acinetobacter common
SEQUENCE: 33
IFEDGEIVTG VISGK                                                         15

SEQ ID NO: 34             moltype = AA  length = 17
FEATURE                   Location/Qualifiers
source                    1..17
                          mol_type = protein
                          organism = Acinetobacter Iwoffii
SEQUENCE: 34
GMAMNPVDHP HGGGEGR                                                       17

SEQ ID NO: 35             moltype = AA  length = 12
FEATURE                   Location/Qualifiers
source                    1..12
                          mol_type = protein
                          organism = Acinetobacter Iwoffii
SEQUENCE: 35
AVEQLFGVEV VK                                                            12

SEQ ID NO: 36             moltype = AA  length = 13
FEATURE                   Location/Qualifiers
source                    1..13
                          mol_type = protein
                          organism = Acinetobacter Iwoffii
SEQUENCE: 36
QLGEDPWLAI MNR                                                           13

SEQ ID NO: 37             moltype = AA  length = 13
FEATURE                   Location/Qualifiers
source                    1..13
                          mol_type = protein
                          organism = Acinetobacter Iwoffii
SEQUENCE: 37
SIAESIVYGA LDR                                                           13

SEQ ID NO: 38             moltype = AA  length = 7
FEATURE                   Location/Qualifiers
source                    1..7
                          mol_type = protein
                          organism = Acinetobacter pittii
SEQUENCE: 38
LQLAPVK                                                                  7

SEQ ID NO: 39             moltype = AA  length = 14
FEATURE                   Location/Qualifiers
source                    1..14
                          mol_type = protein
                          organism = Acinetobacter pittii
SEQUENCE: 39
ILYEIEGVNE ELAR                                                          14

SEQ ID NO: 40             moltype = AA  length = 7
FEATURE                   Location/Qualifiers
```

```
source                  1..7
                        mol_type = protein
                        organism = Acinetobacter pittii
SEQUENCE: 40
LFEDFAK                                                    7

SEQ ID NO: 41           moltype = AA  length = 14
FEATURE                 Location/Qualifiers
source                  1..14
                        mol_type = protein
                        organism = Acinetobacter pittii
SEQUENCE: 41
AQVLGDTVGV QVFK                                            14

SEQ ID NO: 42           moltype = AA  length = 11
FEATURE                 Location/Qualifiers
source                  1..11
                        mol_type = protein
                        organism = Acinetobacter pittii
SEQUENCE: 42
QPLELLEVTE K                                               11

SEQ ID NO: 43           moltype = AA  length = 12
FEATURE                 Location/Qualifiers
source                  1..12
                        mol_type = protein
                        organism = Actinomyces odontolyticus
SEQUENCE: 43
GTHFHPGDGV GR                                              12

SEQ ID NO: 44           moltype = AA  length = 11
FEATURE                 Location/Qualifiers
source                  1..11
                        mol_type = protein
                        organism = Actinomyces odontolyticus
SEQUENCE: 44
IQVFQGVVIA R                                               11

SEQ ID NO: 45           moltype = AA  length = 16
FEATURE                 Location/Qualifiers
source                  1..16
                        mol_type = protein
                        organism = Actinomyces odontolyticus
SEQUENCE: 45
TAGLTGENLV ELLEMR                                          16

SEQ ID NO: 46           moltype = AA  length = 17
FEATURE                 Location/Qualifiers
source                  1..17
                        mol_type = protein
                        organism = Actinomyces odontolyticus
SEQUENCE: 46
VEDGIEGLVH ISELAQR                                         17

SEQ ID NO: 47           moltype = AA  length = 11
FEATURE                 Location/Qualifiers
source                  1..11
                        mol_type = protein
                        organism = Aerococcus viridans
SEQUENCE: 47
EATASAVSAQ R                                               11

SEQ ID NO: 48           moltype = AA  length = 8
FEATURE                 Location/Qualifiers
source                  1..8
                        mol_type = protein
                        organism = Aerococcus viridans
SEQUENCE: 48
GASSGWGK                                                   8

SEQ ID NO: 49           moltype = AA  length = 8
FEATURE                 Location/Qualifiers
source                  1..8
                        mol_type = protein
                        organism = Aerococcus viridans
SEQUENCE: 49
MLDQAASK                                                   8

SEQ ID NO: 50           moltype = AA  length = 8
```

-continued

```
FEATURE                 Location/Qualifiers
source                  1..8
                        mol_type = protein
                        organism = Aerococcus viridans
SEQUENCE: 50
IAIQEAHK                                                                  8

SEQ ID NO: 51           moltype = AA  length = 11
FEATURE                 Location/Qualifiers
source                  1..11
                        mol_type = protein
                        organism = Aerococcus viridans
SEQUENCE: 51
VGDTLELVVI K                                                              11

SEQ ID NO: 52           moltype = AA  length = 11
FEATURE                 Location/Qualifiers
source                  1..11
                        mol_type = protein
                        organism = Aerococcus viridans
SEQUENCE: 52
YALSEAIELL K                                                              11

SEQ ID NO: 53           moltype = AA  length = 14
FEATURE                 Location/Qualifiers
source                  1..14
                        mol_type = protein
                        organism = Aerococcus viridans
SEQUENCE: 53
NWVVLDATDV PLGR                                                           14

SEQ ID NO: 54           moltype = AA  length = 10
FEATURE                 Location/Qualifiers
source                  1..10
                        mol_type = protein
                        organism = Bacillus simplex
SEQUENCE: 54
VATIEYDPNR                                                                10

SEQ ID NO: 55           moltype = AA  length = 10
FEATURE                 Location/Qualifiers
source                  1..10
                        mol_type = protein
                        organism = Bacillus simplex
SEQUENCE: 55
MYAIIETGGK                                                                10

SEQ ID NO: 56           moltype = AA  length = 12
FEATURE                 Location/Qualifiers
source                  1..12
                        mol_type = protein
                        organism = Bacillus simplex
SEQUENCE: 56
LDLPSGVDIE IK                                                             12

SEQ ID NO: 57           moltype = AA  length = 14
FEATURE                 Location/Qualifiers
source                  1..14
                        mol_type = protein
                        organism = Bacillus simplex
SEQUENCE: 57
WLGGTLTNFE TIQK                                                           14

SEQ ID NO: 58           moltype = AA  length = 12
FEATURE                 Location/Qualifiers
source                  1..12
                        mol_type = protein
                        organism = Bacillus simplex
SEQUENCE: 58
EQLIFPEIDY DK                                                             12

SEQ ID NO: 59           moltype = AA  length = 9
FEATURE                 Location/Qualifiers
source                  1..9
                        mol_type = protein
                        organism = Bacillus simplex
SEQUENCE: 59
MADAILEAK                                                                 9
```

-continued

```
SEQ ID NO: 60           moltype = AA  length = 10
FEATURE                 Location/Qualifiers
source                  1..10
                        mol_type = protein
                        organism = Bacillus simplex
SEQUENCE: 60
TGTVTFDVTK                                                          10

SEQ ID NO: 61           moltype = AA  length = 14
FEATURE                 Location/Qualifiers
source                  1..14
                        mol_type = protein
                        organism = Bacteroides fragilis
SEQUENCE: 61
GITGEVLLQM LEGR                                                     14

SEQ ID NO: 62           moltype = AA  length = 10
FEATURE                 Location/Qualifiers
source                  1..10
                        mol_type = protein
                        organism = Bacteroides fragilis
SEQUENCE: 62
LLVVLPEANK                                                          10

SEQ ID NO: 63           moltype = AA  length = 19
FEATURE                 Location/Qualifiers
source                  1..19
                        mol_type = protein
                        organism = Bacteroides fragilis
SEQUENCE: 63
QLTPHPWDAL DPNLQVGDK                                                19

SEQ ID NO: 64           moltype = AA  length = 12
FEATURE                 Location/Qualifiers
source                  1..12
                        mol_type = protein
                        organism = Bacteroides fragilis
SEQUENCE: 64
AFAEQLVNLT VK                                                       12

SEQ ID NO: 65           moltype = AA  length = 12
FEATURE                 Location/Qualifiers
source                  1..12
                        mol_type = protein
                        organism = Bacteroides fragilis
SEQUENCE: 65
LNVVILDFDD EK                                                       12

SEQ ID NO: 66           moltype = AA  length = 14
FEATURE                 Location/Qualifiers
source                  1..14
                        mol_type = protein
                        organism = Bacteroides fragilis
SEQUENCE: 66
VINGLGIAII STSK                                                     14

SEQ ID NO: 67           moltype = AA  length = 7
FEATURE                 Location/Qualifiers
source                  1..7
                        mol_type = protein
                        organism = Bacteroides thetaiotaomicron
SEQUENCE: 67
VGEMIAK                                                             7

SEQ ID NO: 68           moltype = AA  length = 14
FEATURE                 Location/Qualifiers
source                  1..14
                        mol_type = protein
                        organism = Bacteroides thetaiotaomicron
SEQUENCE: 68
FIPVYVTENM VGHK                                                     14

SEQ ID NO: 69           moltype = AA  length = 14
FEATURE                 Location/Qualifiers
source                  1..14
                        mol_type = protein
                        organism = Bacteroides thetaiotaomicron
SEQUENCE: 69
GAPEGFVAPV TPGR                                                     14
```

```
SEQ ID NO: 70          moltype = AA  length = 8
FEATURE                Location/Qualifiers
source                 1..8
                       mol_type = protein
                       organism = Bacteroides thetaiotaomicron
SEQUENCE: 70
TSFDVVLK                                                                    8

SEQ ID NO: 71          moltype = AA  length = 10
FEATURE                Location/Qualifiers
source                 1..10
                       mol_type = protein
                       organism = Bacteroides vulgatus
SEQUENCE: 71
AGDTITVAYR                                                                  10

SEQ ID NO: 72          moltype = AA  length = 9
FEATURE                Location/Qualifiers
source                 1..9
                       mol_type = protein
                       organism = Bacteroides vulgatus
SEQUENCE: 72
ALYNVIPER                                                                   9

SEQ ID NO: 73          moltype = AA  length = 9
FEATURE                Location/Qualifiers
source                 1..9
                       mol_type = protein
                       organism = Campylobacter coli
SEQUENCE: 73
HSGYFGSVK                                                                   9

SEQ ID NO: 74          moltype = AA  length = 10
FEATURE                Location/Qualifiers
source                 1..10
                       mol_type = protein
                       organism = Campylobacter coli
SEQUENCE: 74
LDVGDALLVR                                                                  10

SEQ ID NO: 75          moltype = AA  length = 12
FEATURE                Location/Qualifiers
source                 1..12
                       mol_type = protein
                       organism = Campylobacter coli
SEQUENCE: 75
SLGSNNSANV VR                                                               12

SEQ ID NO: 76          moltype = AA  length = 8
FEATURE                Location/Qualifiers
source                 1..8
                       mol_type = protein
                       organism = Campylobacter coli
SEQUENCE: 76
FMYGVSEK                                                                    8

SEQ ID NO: 77          moltype = AA  length = 12
FEATURE                Location/Qualifiers
source                 1..12
                       mol_type = protein
                       organism = Campylobacter coli
SEQUENCE: 77
LAAELLDAAN SK                                                               12

SEQ ID NO: 78          moltype = AA  length = 9
FEATURE                Location/Qualifiers
source                 1..9
                       mol_type = protein
                       organism = Campylobacter coli
SEQUENCE: 78
ALMDLGSFR                                                                   9

SEQ ID NO: 79          moltype = AA  length = 17
FEATURE                Location/Qualifiers
source                 1..17
                       mol_type = protein
                       organism = Campylobacter coli
SEQUENCE: 79
```

-continued

```
MLDIVAATPD TVDSLTK                                         17

SEQ ID NO: 80          moltype = AA  length = 11
FEATURE                Location/Qualifiers
source                 1..11
                       mol_type = protein
                       organism = Campylobacter coli
SEQUENCE: 80
LLELIGVPFT K                                               11

SEQ ID NO: 81          moltype = AA  length = 15
FEATURE                Location/Qualifiers
source                 1..15
                       mol_type = protein
                       organism = Candida albicans
SEQUENCE: 81
VETGNFSWGS EGVSR                                           15

SEQ ID NO: 82          moltype = AA  length = 13
FEATURE                Location/Qualifiers
source                 1..13
                       mol_type = protein
                       organism = Candida albicans
SEQUENCE: 82
IIVAPIATET AMK                                             13

SEQ ID NO: 83          moltype = AA  length = 12
FEATURE                Location/Qualifiers
source                 1..12
                       mol_type = protein
                       organism = Candida albicans
SEQUENCE: 83
YGNVNNDFVL LK                                              12

SEQ ID NO: 84          moltype = AA  length = 11
FEATURE                Location/Qualifiers
source                 1..11
                       mol_type = protein
                       organism = Candida albicans
SEQUENCE: 84
QVVFEIPGES H                                               11

SEQ ID NO: 85          moltype = AA  length = 11
FEATURE                Location/Qualifiers
source                 1..11
                       mol_type = protein
                       organism = Candida albicans
SEQUENCE: 85
SVDAALLSEI K                                               11

SEQ ID NO: 86          moltype = AA  length = 11
FEATURE                Location/Qualifiers
source                 1..11
                       mol_type = protein
                       organism = Candida albicans
SEQUENCE: 86
AVASGASVVS K                                               11

SEQ ID NO: 87          moltype = AA  length = 7
FEATURE                Location/Qualifiers
source                 1..7
                       mol_type = protein
                       organism = Candida auris
SEQUENCE: 87
APSTFER                                                    7

SEQ ID NO: 88          moltype = AA  length = 7
FEATURE                Location/Qualifiers
source                 1..7
                       mol_type = protein
                       organism = Candida auris
SEQUENCE: 88
AVEVPEK                                                    7

SEQ ID NO: 89          moltype = AA  length = 7
FEATURE                Location/Qualifiers
source                 1..7
                       mol_type = protein
                       organism = Candida auris
```

-continued

```
SEQUENCE: 89
TAYETLR                                                        7

SEQ ID NO: 90          moltype = AA  length = 8
FEATURE                Location/Qualifiers
source                 1..8
                       mol_type = protein
                       organism = Candida auris
SEQUENCE: 90
LVMVTGGK                                                       8

SEQ ID NO: 91          moltype = AA  length = 8
FEATURE                Location/Qualifiers
source                 1..8
                       mol_type = protein
                       organism = Candida auris
SEQUENCE: 91
VGVLPEDK                                                       8

SEQ ID NO: 92          moltype = AA  length = 7
FEATURE                Location/Qualifiers
source                 1..7
                       mol_type = protein
                       organism = Candida auris
SEQUENCE: 92
AVDPFAK                                                        7

SEQ ID NO: 93          moltype = AA  length = 7
FEATURE                Location/Qualifiers
source                 1..7
                       mol_type = protein
                       organism = Candida auris
SEQUENCE: 93
EVGLGFK                                                        7

SEQ ID NO: 94          moltype = AA  length = 9
FEATURE                Location/Qualifiers
source                 1..9
                       mol_type = protein
                       organism = Candida auris
SEQUENCE: 94
VAPLPLAAK                                                      9

SEQ ID NO: 95          moltype = AA  length = 8
FEATURE                Location/Qualifiers
source                 1..8
                       mol_type = protein
                       organism = Candida auris
SEQUENCE: 95
LLAGLPIR                                                       8

SEQ ID NO: 96          moltype = AA  length = 11
FEATURE                Location/Qualifiers
source                 1..11
                       mol_type = protein
                       organism = Candida auris
SEQUENCE: 96
SPLDVFSEEA K                                                   11

SEQ ID NO: 97          moltype = AA  length = 14
FEATURE                Location/Qualifiers
source                 1..14
                       mol_type = protein
                       organism = Candida auris
SEQUENCE: 97
SIVSEVSGLA PYER                                                14

SEQ ID NO: 98          moltype = AA  length = 10
FEATURE                Location/Qualifiers
source                 1..10
                       mol_type = protein
                       organism = Candida auris
SEQUENCE: 98
TINPLGGFVR                                                     10

SEQ ID NO: 99          moltype = AA  length = 12
FEATURE                Location/Qualifiers
source                 1..12
                       mol_type = protein
```

```
                        organism = Candida auris
SEQUENCE: 99
VIDLQAPAQI VK                                                   12

SEQ ID NO: 100          moltype = AA  length = 11
FEATURE                 Location/Qualifiers
source                  1..11
                        mol_type = protein
                        organism = Candida auris
SEQUENCE: 100
GQLPQVPIIV K                                                    11

SEQ ID NO: 101          moltype = AA  length = 15
FEATURE                 Location/Qualifiers
source                  1..15
                        mol_type = protein
                        organism = Candida auris
SEQUENCE: 101
ALAIFVPVPS LVGYR                                                15

SEQ ID NO: 102          moltype = AA  length = 12
FEATURE                 Location/Qualifiers
source                  1..12
                        mol_type = protein
                        organism = Candida common
SEQUENCE: 102
TSFFQALGVP TK                                                   12

SEQ ID NO: 103          moltype = AA  length = 8
FEATURE                 Location/Qualifiers
source                  1..8
                        mol_type = protein
                        organism = Candida common
SEQUENCE: 103
AFLIEEQK                                                        8

SEQ ID NO: 104          moltype = AA  length = 7
FEATURE                 Location/Qualifiers
source                  1..7
                        mol_type = protein
                        organism = Candida common
SEQUENCE: 104
LLGTAFK                                                         7

SEQ ID NO: 105          moltype = AA  length = 9
FEATURE                 Location/Qualifiers
source                  1..9
                        mol_type = protein
                        organism = Candida common
SEQUENCE: 105
IGPLGLSPK                                                       9

SEQ ID NO: 106          moltype = AA  length = 7
FEATURE                 Location/Qualifiers
source                  1..7
                        mol_type = protein
                        organism = Candida common
SEQUENCE: 106
FQTPAEK                                                         7

SEQ ID NO: 107          moltype = AA  length = 7
FEATURE                 Location/Qualifiers
source                  1..7
                        mol_type = protein
                        organism = Candida common
SEQUENCE: 107
TFGASVR                                                         7

SEQ ID NO: 108          moltype = AA  length = 9
FEATURE                 Location/Qualifiers
source                  1..9
                        mol_type = protein
                        organism = Candida glabrata
SEQUENCE: 108
ALSEQAEAR                                                       9

SEQ ID NO: 109          moltype = AA  length = 7
FEATURE                 Location/Qualifiers
source                  1..7
```

-continued

```
                        mol_type = protein
                        organism = Candida glabrata
SEQUENCE: 109
TLVQAPR                                                     7

SEQ ID NO: 110          moltype = AA  length = 7
FEATURE                 Location/Qualifiers
source                  1..7
                        mol_type = protein
                        organism = Candida glabrata
SEQUENCE: 110
TPVTLAR                                                     7

SEQ ID NO: 111          moltype = AA  length = 8
FEATURE                 Location/Qualifiers
source                  1..8
                        mol_type = protein
                        organism = Candida glabrata
SEQUENCE: 111
DDEVLVTR                                                    8

SEQ ID NO: 112          moltype = AA  length = 10
FEATURE                 Location/Qualifiers
source                  1..10
                        mol_type = protein
                        organism = Candida glabrata
SEQUENCE: 112
LAASVIGAGK                                                  10

SEQ ID NO: 113          moltype = AA  length = 8
FEATURE                 Location/Qualifiers
source                  1..8
                        mol_type = protein
                        organism = Candida glabrata
SEQUENCE: 113
VISDILTR                                                    8

SEQ ID NO: 114          moltype = AA  length = 7
FEATURE                 Location/Qualifiers
source                  1..7
                        mol_type = protein
                        organism = Candida glabrata
SEQUENCE: 114
QFLELTR                                                     7

SEQ ID NO: 115          moltype = AA  length = 11
FEATURE                 Location/Qualifiers
source                  1..11
                        mol_type = protein
                        organism = Candida glabrata
SEQUENCE: 115
GVIGVIAGGG R                                                11

SEQ ID NO: 116          moltype = AA  length = 9
FEATURE                 Location/Qualifiers
source                  1..9
                        mol_type = protein
                        organism = Candida glabrata
SEQUENCE: 116
YTLDVESFK                                                   9

SEQ ID NO: 117          moltype = AA  length = 11
FEATURE                 Location/Qualifiers
source                  1..11
                        mol_type = protein
                        organism = Candida glabrata
SEQUENCE: 117
LLEMSTEDFI K                                                11

SEQ ID NO: 118          moltype = AA  length = 8
FEATURE                 Location/Qualifiers
source                  1..8
                        mol_type = protein
                        organism = Candida glabrata
SEQUENCE: 118
GFSLAEIK                                                    8

SEQ ID NO: 119          moltype = AA  length = 10
FEATURE                 Location/Qualifiers
```

-continued

```
source                  1..10
                        mol_type = protein
                        organism = Candida glabrata
SEQUENCE: 119
QIVFEIPETH                                                   10

SEQ ID NO: 120          moltype = AA  length = 7
FEATURE                 Location/Qualifiers
source                  1..7
                        mol_type = protein
                        organism = Candida kefyr
SEQUENCE: 120
QYATVSR                                                      7

SEQ ID NO: 121          moltype = AA  length = 7
FEATURE                 Location/Qualifiers
source                  1..7
                        mol_type = protein
                        organism = Candida kefyr
SEQUENCE: 121
TPGGVLR                                                      7

SEQ ID NO: 122          moltype = AA  length = 13
FEATURE                 Location/Qualifiers
source                  1..13
                        mol_type = protein
                        organism = Candida kefyr
SEQUENCE: 122
VIEQPITSET AMK                                               13

SEQ ID NO: 123          moltype = AA  length = 9
FEATURE                 Location/Qualifiers
source                  1..9
                        mol_type = protein
                        organism = Candida kefyr
SEQUENCE: 123
VVYALTTIR                                                    9

SEQ ID NO: 124          moltype = AA  length = 11
FEATURE                 Location/Qualifiers
source                  1..11
                        mol_type = protein
                        organism = Candida kefyr
SEQUENCE: 124
AVVGASLELI K                                                 11

SEQ ID NO: 125          moltype = AA  length = 9
FEATURE                 Location/Qualifiers
source                  1..9
                        mol_type = protein
                        organism = Candida kefyr
SEQUENCE: 125
LWTLVPEEK                                                    9

SEQ ID NO: 126          moltype = AA  length = 12
FEATURE                 Location/Qualifiers
source                  1..12
                        mol_type = protein
                        organism = Candida kefyr
SEQUENCE: 126
EGDILVLMES ER                                                12

SEQ ID NO: 127          moltype = AA  length = 11
FEATURE                 Location/Qualifiers
source                  1..11
                        mol_type = protein
                        organism = Candida krusei
SEQUENCE: 127
AVVVPEQTAY R                                                 11

SEQ ID NO: 128          moltype = AA  length = 8
FEATURE                 Location/Qualifiers
source                  1..8
                        mol_type = protein
                        organism = Candida krusei
SEQUENCE: 128
ALEQVNLK                                                     8

SEQ ID NO: 129          moltype = AA  length = 13
```

-continued

```
FEATURE               Location/Qualifiers
source                1..13
                      mol_type = protein
                      organism = Candida krusei
SEQUENCE: 129
VIQSPITSES ATK                                                    13

SEQ ID NO: 130        moltype = AA  length = 9
FEATURE               Location/Qualifiers
source                1..9
                      mol_type = protein
                      organism = Candida krusei
SEQUENCE: 130
VFLDVGLQR                                                         9

SEQ ID NO: 131        moltype = AA  length = 10
FEATURE               Location/Qualifiers
source                1..10
                      mol_type = protein
                      organism = Candida krusei
SEQUENCE: 131
TITPMGGFVR                                                        10

SEQ ID NO: 132        moltype = AA  length = 11
FEATURE               Location/Qualifiers
source                1..11
                      mol_type = protein
                      organism = Candida krusei
SEQUENCE: 132
AIVGASLDLI K                                                      11

SEQ ID NO: 133        moltype = AA  length = 14
FEATURE               Location/Qualifiers
source                1..14
                      mol_type = protein
                      organism = Candida krusei
SEQUENCE: 133
ILDDLVFPTE IVGK                                                   14

SEQ ID NO: 134        moltype = AA  length = 12
FEATURE               Location/Qualifiers
source                1..12
                      mol_type = protein
                      organism = Candida krusei
SEQUENCE: 134
FTPGSFTNYI TK                                                     12

SEQ ID NO: 135        moltype = AA  length = 12
FEATURE               Location/Qualifiers
source                1..12
                      mol_type = protein
                      organism = Candida krusei
SEQUENCE: 135
SAIVQIDATP FK                                                     12

SEQ ID NO: 136        moltype = AA  length = 12
FEATURE               Location/Qualifiers
source                1..12
                      mol_type = protein
                      organism = Candida krusei
SEQUENCE: 136
MIIIAANTPV LR                                                     12

SEQ ID NO: 137        moltype = AA  length = 10
FEATURE               Location/Qualifiers
source                1..10
                      mol_type = protein
                      organism = Candida parapsilosis
SEQUENCE: 137
NSLVHDGLAR                                                        10

SEQ ID NO: 138        moltype = AA  length = 11
FEATURE               Location/Qualifiers
source                1..11
                      mol_type = protein
                      organism = Candida parapsilosis
SEQUENCE: 138
AVEVPEQSAY R                                                      11
```

-continued

```
SEQ ID NO: 139          moltype = AA  length = 7
FEATURE                 Location/Qualifiers
source                  1..7
                        mol_type = protein
                        organism = Candida parapsilosis
SEQUENCE: 139
LLVQQPR                                                     7

SEQ ID NO: 140          moltype = AA  length = 15
FEATURE                 Location/Qualifiers
source                  1..15
                        mol_type = protein
                        organism = Candida parapsilosis
SEQUENCE: 140
IAGVVYHPSN NELVR                                            15

SEQ ID NO: 141          moltype = AA  length = 12
FEATURE                 Location/Qualifiers
source                  1..12
                        mol_type = protein
                        organism = Candida parapsilosis
SEQUENCE: 141
LISTIDANYL QK                                               12

SEQ ID NO: 142          moltype = AA  length = 12
FEATURE                 Location/Qualifiers
source                  1..12
                        mol_type = protein
                        organism = Candida parapsilosis
SEQUENCE: 142
ILAESPSPLD LK                                               12

SEQ ID NO: 143          moltype = AA  length = 11
FEATURE                 Location/Qualifiers
source                  1..11
                        mol_type = protein
                        organism = Candida parapsilosis
SEQUENCE: 143
QVVFEIPGET H                                                11

SEQ ID NO: 144          moltype = AA  length = 15
FEATURE                 Location/Qualifiers
source                  1..15
                        mol_type = protein
                        organism = Candida parapsilosis
SEQUENCE: 144
ALAIFVPPPS VVGYR                                            15

SEQ ID NO: 145          moltype = AA  length = 7
FEATURE                 Location/Qualifiers
source                  1..7
                        mol_type = protein
                        organism = Candida tropicalis
SEQUENCE: 145
YASSIGR                                                     7

SEQ ID NO: 146          moltype = AA  length = 11
FEATURE                 Location/Qualifiers
source                  1..11
                        mol_type = protein
                        organism = Candida tropicalis
SEQUENCE: 146
LAASGASVVS K                                                11

SEQ ID NO: 147          moltype = AA  length = 11
FEATURE                 Location/Qualifiers
source                  1..11
                        mol_type = protein
                        organism = Candida tropicalis
SEQUENCE: 147
NFGIGQSVQP K                                                11

SEQ ID NO: 148          moltype = AA  length = 11
FEATURE                 Location/Qualifiers
source                  1..11
                        mol_type = protein
                        organism = Candida tropicalis
SEQUENCE: 148
QVVFEIPGEN H                                                11
```

-continued

```
SEQ ID NO: 149          moltype = AA  length = 17
FEATURE                 Location/Qualifiers
source                  1..17
                        mol_type = protein
                        organism = Candida tropicalis
SEQUENCE: 149
SGYTLPANII SNTDVTR                                                  17

SEQ ID NO: 150          moltype = AA  length = 15
FEATURE                 Location/Qualifiers
source                  1..15
                        mol_type = protein
                        organism = Candida tropicalis
SEQUENCE: 150
ALAVFVPPPS LAAYR                                                    15

SEQ ID NO: 151          moltype = AA  length = 13
FEATURE                 Location/Qualifiers
source                  1..13
                        mol_type = protein
                        organism = Capnocytophaga sputigena
SEQUENCE: 151
TAPAAVQLLE AAK                                                      13

SEQ ID NO: 152          moltype = AA  length = 12
FEATURE                 Location/Qualifiers
source                  1..12
                        mol_type = protein
                        organism = Capnocytophaga sputigena
SEQUENCE: 152
NFAEQLVNLT VK                                                       12

SEQ ID NO: 153          moltype = AA  length = 13
FEATURE                 Location/Qualifiers
source                  1..13
                        mol_type = protein
                        organism = Capnocytophaga sputigena
SEQUENCE: 153
STLGDLEVLQ ELK                                                      13

SEQ ID NO: 154          moltype = AA  length = 14
FEATURE                 Location/Qualifiers
source                  1..14
                        mol_type = protein
                        organism = Capnocytophaga sputigena
SEQUENCE: 154
IMFEVGGVPL DVAK                                                     14

SEQ ID NO: 155          moltype = AA  length = 14
FEATURE                 Location/Qualifiers
source                  1..14
                        mol_type = protein
                        organism = Citrobacter freundii and Citrobacter braakii
SEQUENCE: 155
GNTGENLLGL LEGR                                                     14

SEQ ID NO: 156          moltype = AA  length = 11
FEATURE                 Location/Qualifiers
source                  1..11
                        mol_type = protein
                        organism = Citrobacter freundii and Citrobacter braakii
SEQUENCE: 156
LADVLSAAEA R                                                        11

SEQ ID NO: 157          moltype = AA  length = 8
FEATURE                 Location/Qualifiers
source                  1..8
                        mol_type = protein
                        organism = Citrobacter koseri
SEQUENCE: 157
LATELALR                                                            8

SEQ ID NO: 158          moltype = AA  length = 10
FEATURE                 Location/Qualifiers
source                  1..10
                        mol_type = protein
                        organism = Citrobacter koseri
SEQUENCE: 158
```

VSVVNNPTGR 10

SEQ ID NO: 159 moltype = AA length = 15
FEATURE Location/Qualifiers
source 1..15
mol_type = protein
organism = Clostridium perfringens
SEQUENCE: 159
NALYTPAEAL ELAVK 15

SEQ ID NO: 160 moltype = AA length = 16
FEATURE Location/Qualifiers
source 1..16
mol_type = protein
organism = Clostridium perfringens
SEQUENCE: 160
ALLNNMVVGV SQGFSK 16

SEQ ID NO: 161 moltype = AA length = 12
FEATURE Location/Qualifiers
source 1..12
mol_type = protein
organism = Clostridium perfringens
SEQUENCE: 161
VLFELSGVDE EK 12

SEQ ID NO: 162 moltype = AA length = 12
FEATURE Location/Qualifiers
source 1..12
mol_type = protein
organism = Clostridium perfringens
SEQUENCE: 162
EIETYFGLET LR 12

SEQ ID NO: 163 moltype = AA length = 13
FEATURE Location/Qualifiers
source 1..13
mol_type = protein
organism = Clostridium perfringens
SEQUENCE: 163
AIVNILLQEG YLK 13

SEQ ID NO: 164 moltype = AA length = 12
FEATURE Location/Qualifiers
source 1..12
mol_type = protein
organism = Eggerthella lenta
SEQUENCE: 164
EALVNYALTP FK 12

SEQ ID NO: 165 moltype = AA length = 9
FEATURE Location/Qualifiers
source 1..9
mol_type = protein
organism = Eggerthella lenta
SEQUENCE: 165
SLLAPLSNK 9

SEQ ID NO: 166 moltype = AA length = 10
FEATURE Location/Qualifiers
source 1..10
mol_type = protein
organism = Eggerthella lenta
SEQUENCE: 166
LLDAAMGDLR 10

SEQ ID NO: 167 moltype = AA length = 8
FEATURE Location/Qualifiers
source 1..8
mol_type = protein
organism = Eggerthella lenta
SEQUENCE: 167
AADLLVIK 8

SEQ ID NO: 168 moltype = AA length = 9
FEATURE Location/Qualifiers
source 1..9
mol_type = protein
organism = Enterobacter asburiae -continued

```
SEQUENCE: 168
GISNVSFDR                                                     9

SEQ ID NO: 169         moltype = AA  length = 10
FEATURE                Location/Qualifiers
source                 1..10
                       mol_type = protein
                       organism = Enterobacterales common
SEQUENCE: 169
YLSLLPYTDR                                                    10

SEQ ID NO: 170         moltype = AA  length = 12
FEATURE                Location/Qualifiers
source                 1..12
                       mol_type = protein
                       organism = Enterobacterales common
SEQUENCE: 170
QLGEDPWVAI AK                                                 12

SEQ ID NO: 171         moltype = AA  length = 11
FEATURE                Location/Qualifiers
source                 1..11
                       mol_type = protein
                       organism = Enterobacterales common
SEQUENCE: 171
FTVLISPHVN K                                                  11

SEQ ID NO: 172         moltype = AA  length = 10
FEATURE                Location/Qualifiers
source                 1..10
                       mol_type = protein
                       organism = Enterobacterales common
SEQUENCE: 172
VVEPLITLAK                                                    10

SEQ ID NO: 173         moltype = AA  length = 12
FEATURE                Location/Qualifiers
source                 1..12
                       mol_type = protein
                       organism = Enterobacterales common
SEQUENCE: 173
LVADSITSQL ER                                                 12

SEQ ID NO: 174         moltype = AA  length = 6
FEATURE                Location/Qualifiers
source                 1..6
                       mol_type = protein
                       organism = Enterobacterales common
SEQUENCE: 174
FGFTSR                                                        6

SEQ ID NO: 175         moltype = AA  length = 14
FEATURE                Location/Qualifiers
source                 1..14
                       mol_type = protein
                       organism = Enterobacterales common
SEQUENCE: 175
VANLGSLGDQ VNVK                                               14

SEQ ID NO: 176         moltype = AA  length = 11
FEATURE                Location/Qualifiers
source                 1..11
                       mol_type = protein
                       organism = Enterobacterales common
SEQUENCE: 176
GGFTVELNGI R                                                  11

SEQ ID NO: 177         moltype = AA  length = 8
FEATURE                Location/Qualifiers
source                 1..8
                       mol_type = protein
                       organism = Enterobacterales common
SEQUENCE: 177
NYITESGK                                                      8

SEQ ID NO: 178         moltype = AA  length = 11
FEATURE                Location/Qualifiers
source                 1..11
                       mol_type = protein
```

```
                         organism = Enterobacterales common
SEQUENCE: 178
AVIESENSAE R                                                   11

SEQ ID NO: 179           moltype = AA  length = 8
FEATURE                  Location/Qualifiers
source                   1..8
                         mol_type = protein
                         organism = Enterobacterales common
SEQUENCE: 179
NMAGSLVR                                                       8

SEQ ID NO: 180           moltype = AA  length = 10
FEATURE                  Location/Qualifiers
source                   1..10
                         mol_type = protein
                         organism = Enterobacterales common
SEQUENCE: 180
FVNILMVDGK                                                     10

SEQ ID NO: 181           moltype = AA  length = 10
FEATURE                  Location/Qualifiers
source                   1..10
                         mol_type = protein
                         organism = Enterococcus common
SEQUENCE: 181
EGVVLAAFPK                                                     10

SEQ ID NO: 182           moltype = AA  length = 9
FEATURE                  Location/Qualifiers
source                   1..9
                         mol_type = protein
                         organism = Enterococcus common
SEQUENCE: 182
TQTVLVFAK                                                      9

SEQ ID NO: 183           moltype = AA  length = 10
FEATURE                  Location/Qualifiers
source                   1..10
                         mol_type = protein
                         organism = Enterococcus common
SEQUENCE: 183
LVDAAYDYMK                                                     10

SEQ ID NO: 184           moltype = AA  length = 11
FEATURE                  Location/Qualifiers
source                   1..11
                         mol_type = protein
                         organism = Enterococcus common
SEQUENCE: 184
NVELGEYEVG K                                                   11

SEQ ID NO: 185           moltype = AA  length = 12
FEATURE                  Location/Qualifiers
source                   1..12
                         mol_type = protein
                         organism = Enterococcus common
SEQUENCE: 185
SLGSNTPINV VR                                                  12

SEQ ID NO: 186           moltype = AA  length = 10
FEATURE                  Location/Qualifiers
source                   1..10
                         mol_type = protein
                         organism = Enterococcus common
SEQUENCE: 186
FLGGIADMPR                                                     10

SEQ ID NO: 187           moltype = AA  length = 10
FEATURE                  Location/Qualifiers
source                   1..10
                         mol_type = protein
                         organism = Enterococcus common
SEQUENCE: 187
SVADAISILK                                                     10

SEQ ID NO: 188           moltype = AA  length = 14
FEATURE                  Location/Qualifiers
source                   1..14
```

-continued

```
                        mol_type = protein
                        organism = Enterococcus faecalis
SEQUENCE: 188
EEDESIVVES ALQK                                                           14

SEQ ID NO: 189          moltype = AA  length = 11
FEATURE                 Location/Qualifiers
source                  1..11
                        mol_type = protein
                        organism = Enterococcus faecalis
SEQUENCE: 189
QVLANLSIDT K                                                              11

SEQ ID NO: 190          moltype = AA  length = 11
FEATURE                 Location/Qualifiers
source                  1..11
                        mol_type = protein
                        organism = Enterococcus faecalis
SEQUENCE: 190
VVVLPAGVEI K                                                              11

SEQ ID NO: 191          moltype = AA  length = 12
FEATURE                 Location/Qualifiers
source                  1..12
                        mol_type = protein
                        organism = Enterococcus faecalis
SEQUENCE: 191
VSSVEQITAL AK                                                             12

SEQ ID NO: 192          moltype = AA  length = 13
FEATURE                 Location/Qualifiers
source                  1..13
                        mol_type = protein
                        organism = Enterococcus faecalis
SEQUENCE: 192
LADAAVSTIE IER                                                            13

SEQ ID NO: 193          moltype = AA  length = 13
FEATURE                 Location/Qualifiers
source                  1..13
                        mol_type = protein
                        organism = Enterococcus faecalis
SEQUENCE: 193
EVINQPFGVT ETK                                                            13

SEQ ID NO: 194          moltype = AA  length = 13
FEATURE                 Location/Qualifiers
source                  1..13
                        mol_type = protein
                        organism = Enterococcus faecalis
SEQUENCE: 194
FEDGTEVTPV VLK                                                            13

SEQ ID NO: 195          moltype = AA  length = 12
FEATURE                 Location/Qualifiers
source                  1..12
                        mol_type = protein
                        organism = Enterococcus faecium
SEQUENCE: 195
VYPVAEAVAL AK                                                             12

SEQ ID NO: 196          moltype = AA  length = 12
FEATURE                 Location/Qualifiers
source                  1..12
                        mol_type = protein
                        organism = Enterococcus faecium
SEQUENCE: 196
VSSLEEITAL AK                                                             12

SEQ ID NO: 197          moltype = AA  length = 10
FEATURE                 Location/Qualifiers
source                  1..10
                        mol_type = protein
                        organism = Enterococcus faecium
SEQUENCE: 197
VTIQNLEVVR                                                                10

SEQ ID NO: 198          moltype = AA  length = 9
FEATURE                 Location/Qualifiers
```

-continued

```
source                 1..9
                       mol_type = protein
                       organism = Enterococcus faecium
SEQUENCE: 198
NVQPVLEVK                                                                  9

SEQ ID NO: 199         moltype = AA  length = 14
FEATURE                Location/Qualifiers
source                 1..14
                       mol_type = protein
                       organism = Enterococcus faecium
SEQUENCE: 199
EENEDIVIES ALQK                                                            14

SEQ ID NO: 200         moltype = AA  length = 11
FEATURE                Location/Qualifiers
source                 1..11
                       mol_type = protein
                       organism = Escherichia coli
SEQUENCE: 200
YTAAITGAEG K                                                               11

SEQ ID NO: 201         moltype = AA  length = 7
FEATURE                Location/Qualifiers
source                 1..7
                       mol_type = protein
                       organism = Escherichia coli
SEQUENCE: 201
YTQLIER                                                                    7

SEQ ID NO: 202         moltype = AA  length = 8
FEATURE                Location/Qualifiers
source                 1..8
                       mol_type = protein
                       organism = Fusobacterium necrophorum
SEQUENCE: 202
LVNDELDK                                                                   8

SEQ ID NO: 203         moltype = AA  length = 8
FEATURE                Location/Qualifiers
source                 1..8
                       mol_type = protein
                       organism = Fusobacterium necrophorum
SEQUENCE: 203
SEWAVEGK                                                                   8

SEQ ID NO: 204         moltype = AA  length = 9
FEATURE                Location/Qualifiers
source                 1..9
                       mol_type = protein
                       organism = Fusobacterium necrophorum
SEQUENCE: 204
AGMYYVNSR                                                                  9

SEQ ID NO: 205         moltype = AA  length = 10
FEATURE                Location/Qualifiers
source                 1..10
                       mol_type = protein
                       organism = Fusobacterium necrophorum
SEQUENCE: 205
EMTSEDLVVK                                                                 10

SEQ ID NO: 206         moltype = AA  length = 9
FEATURE                Location/Qualifiers
source                 1..9
                       mol_type = protein
                       organism = Fusobacterium necrophorum
SEQUENCE: 206
DYNLYLSAR                                                                  9

SEQ ID NO: 207         moltype = AA  length = 7
FEATURE                Location/Qualifiers
source                 1..7
                       mol_type = protein
                       organism = Fusobacterium necrophorum
SEQUENCE: 207
NAFAFLR                                                                    7

SEQ ID NO: 208         moltype = AA  length = 13
```

-continued

```
FEATURE                Location/Qualifiers
source                 1..13
                       mol_type = protein
                       organism = Fusobacterium necrophorum
SEQUENCE: 208
FQLSLGQLTN TAK                                                    13

SEQ ID NO: 209         moltype = AA  length = 9
FEATURE                Location/Qualifiers
source                 1..9
                       mol_type = protein
                       organism = Granulicatella adiacens
SEQUENCE: 209
ELTNDELDR                                                         9

SEQ ID NO: 210         moltype = AA  length = 13
FEATURE                Location/Qualifiers
source                 1..13
                       mol_type = protein
                       organism = Granulicatella adiacens
SEQUENCE: 210
NVAVTTTFGP GVK                                                    13

SEQ ID NO: 211         moltype = AA  length = 14
FEATURE                Location/Qualifiers
source                 1..14
                       mol_type = protein
                       organism = Granulicatella adiacens
SEQUENCE: 211
AVVELAGISD VTSK                                                   14

SEQ ID NO: 212         moltype = AA  length = 17
FEATURE                Location/Qualifiers
source                 1..17
                       mol_type = protein
                       organism = Granulicatella adiacens
SEQUENCE: 212
IGNKPVVIPA GVTVDLK                                                17

SEQ ID NO: 213         moltype = AA  length = 12
FEATURE                Location/Qualifiers
source                 1..12
                       mol_type = protein
                       organism = Granulicatella adiacens
SEQUENCE: 213
AYPVQEAIAL AK                                                     12

SEQ ID NO: 214         moltype = AA  length = 12
FEATURE                Location/Qualifiers
source                 1..12
                       mol_type = protein
                       organism = Granulicatella adiacens
SEQUENCE: 214
EAGLEGMDDV FK                                                     12

SEQ ID NO: 215         moltype = AA  length = 13
FEATURE                Location/Qualifiers
source                 1..13
                       mol_type = protein
                       organism = Granulicatella adiacens
SEQUENCE: 215
AATILYNAFD IVK                                                    13

SEQ ID NO: 216         moltype = AA  length = 10
FEATURE                Location/Qualifiers
source                 1..10
                       mol_type = protein
                       organism = Granulicatella adiacens
SEQUENCE: 216
ELELIGVGYR                                                        10

SEQ ID NO: 217         moltype = AA  length = 8
FEATURE                Location/Qualifiers
source                 1..8
                       mol_type = protein
                       organism = Granulicatella adiacens
SEQUENCE: 217
VAIANILK                                                          8
```

```
SEQ ID NO: 218          moltype = AA  length = 14
FEATURE                 Location/Qualifiers
source                  1..14
                        mol_type = protein
                        organism = Haemophilus influenzae
SEQUENCE: 218
VNHWVAQGAS LSDR                                                   14

SEQ ID NO: 219          moltype = AA  length = 12
FEATURE                 Location/Qualifiers
source                  1..12
                        mol_type = protein
                        organism = Haemophilus influenzae
SEQUENCE: 219
DVAEAVTAAG VK                                                     12

SEQ ID NO: 220          moltype = AA  length = 12
FEATURE                 Location/Qualifiers
source                  1..12
                        mol_type = protein
                        organism = Haemophilus influenzae
SEQUENCE: 220
SAAEAAFVEM QK                                                     12

SEQ ID NO: 221          moltype = AA  length = 12
FEATURE                 Location/Qualifiers
source                  1..12
                        mol_type = protein
                        organism = Haemophilus influenzae
SEQUENCE: 221
ENLQALLAAL NK                                                     12

SEQ ID NO: 222          moltype = AA  length = 12
FEATURE                 Location/Qualifiers
source                  1..12
                        mol_type = protein
                        organism = Haemophilus influenzae
SEQUENCE: 222
AYEINEAIAV LK                                                     12

SEQ ID NO: 223          moltype = AA  length = 13
FEATURE                 Location/Qualifiers
source                  1..13
                        mol_type = protein
                        organism = Hafnia alvei
SEQUENCE: 223
VSQALETLAY TNK                                                    13

SEQ ID NO: 224          moltype = AA  length = 10
FEATURE                 Location/Qualifiers
source                  1..10
                        mol_type = protein
                        organism = Hafnia alvei
SEQUENCE: 224
GIETVLAEIR                                                        10

SEQ ID NO: 225          moltype = AA  length = 15
FEATURE                 Location/Qualifiers
source                  1..15
                        mol_type = protein
                        organism = Hafnia alvei
SEQUENCE: 225
DVTGIDPVSL IAFDK                                                  15

SEQ ID NO: 226          moltype = AA  length = 14
FEATURE                 Location/Qualifiers
source                  1..14
                        mol_type = protein
                        organism = Hafnia alvei
SEQUENCE: 226
SVEELNTELL SLLR                                                   14

SEQ ID NO: 227          moltype = AA  length = 10
FEATURE                 Location/Qualifiers
source                  1..10
                        mol_type = protein
                        organism = Hafnia alvei
SEQUENCE: 227
ATIDGLASMK                                                        10
```

```
SEQ ID NO: 228          moltype = AA  length = 9
FEATURE                 Location/Qualifiers
source                  1..9
                        mol_type = protein
                        organism = Hafnia alvei
SEQUENCE: 228
MFTIEATAR                                                                   9

SEQ ID NO: 229          moltype = AA  length = 10
FEATURE                 Location/Qualifiers
source                  1..10
                        mol_type = protein
                        organism = Hafnia alvei
SEQUENCE: 229
IGVPFVSGGK                                                                  10

SEQ ID NO: 230          moltype = AA  length = 9
FEATURE                 Location/Qualifiers
source                  1..9
                        mol_type = protein
                        organism = Klebsiella aerogenes
SEQUENCE: 230
AQIVSEFGR                                                                   9

SEQ ID NO: 231          moltype = AA  length = 15
FEATURE                 Location/Qualifiers
source                  1..15
                        mol_type = protein
                        organism = Klebsiella aerogenes
SEQUENCE: 231
DIADAVSAAG VAVAK                                                            15

SEQ ID NO: 232          moltype = AA  length = 15
FEATURE                 Location/Qualifiers
source                  1..15
                        mol_type = protein
                        organism = Klebsiella oxytoca
SEQUENCE: 232
AYEDAETVVG IINGK                                                            15

SEQ ID NO: 233          moltype = AA  length = 18
FEATURE                 Location/Qualifiers
source                  1..18
                        mol_type = protein
                        organism = Klebsiella oxytoca
SEQUENCE: 233
LSDLAHVEGD VIDLNTLK                                                         18

SEQ ID NO: 234          moltype = AA  length = 16
FEATURE                 Location/Qualifiers
source                  1..16
                        mol_type = protein
                        organism = Klebsiella oxytoca
SEQUENCE: 234
VGFFNPIASA TEEGTR                                                           16

SEQ ID NO: 235          moltype = AA  length = 18
FEATURE                 Location/Qualifiers
source                  1..18
                        mol_type = protein
                        organism = Klebsiella pneumoniae
SEQUENCE: 235
LSDLAHVEGD VVDLNALK                                                         18

SEQ ID NO: 236          moltype = AA  length = 8
FEATURE                 Location/Qualifiers
source                  1..8
                        mol_type = protein
                        organism = Lactobacillus casei
SEQUENCE: 236
VANVDMNR                                                                    8

SEQ ID NO: 237          moltype = AA  length = 19
FEATURE                 Location/Qualifiers
source                  1..19
                        mol_type = protein
                        organism = Lactobacillus casei
SEQUENCE: 237
```

```
AAAPVAAGAA AGGDAAATK                                              19

SEQ ID NO: 238          moltype = AA  length = 9
FEATURE                 Location/Qualifiers
source                  1..9
                        mol_type = protein
                        organism = Lactobacillus casei
SEQUENCE: 238
VPAGVTVTK                                                         9

SEQ ID NO: 239          moltype = AA  length = 12
FEATURE                 Location/Qualifiers
source                  1..12
                        mol_type = protein
                        organism = Lactobacillus casei
SEQUENCE: 239
TLLVSQSHTA GR                                                     12

SEQ ID NO: 240          moltype = AA  length = 10
FEATURE                 Location/Qualifiers
source                  1..10
                        mol_type = protein
                        organism = Lactobacillus casei
SEQUENCE: 240
HESLVVPASK                                                        10

SEQ ID NO: 241          moltype = AA  length = 10
FEATURE                 Location/Qualifiers
source                  1..10
                        mol_type = protein
                        organism = Lactobacillus casei
SEQUENCE: 241
AYVNEGPTLK                                                        10

SEQ ID NO: 242          moltype = AA  length = 12
FEATURE                 Location/Qualifiers
source                  1..12
                        mol_type = protein
                        organism = Lactobacillus casei
SEQUENCE: 242
DASILELNDL VK                                                     12

SEQ ID NO: 243          moltype = AA  length = 10
FEATURE                 Location/Qualifiers
source                  1..10
                        mol_type = protein
                        organism = Lactobacillus casei
SEQUENCE: 243
LSSVVASILR                                                        10

SEQ ID NO: 244          moltype = AA  length = 12
FEATURE                 Location/Qualifiers
source                  1..12
                        mol_type = protein
                        organism = Lactobacillus casei
SEQUENCE: 244
LNEEDILNWL QK                                                     12

SEQ ID NO: 245          moltype = AA  length = 9
FEATURE                 Location/Qualifiers
source                  1..9
                        mol_type = protein
                        organism = Morganella morganii
SEQUENCE: 245
NIHNAVEVK                                                         9

SEQ ID NO: 246          moltype = AA  length = 9
FEATURE                 Location/Qualifiers
source                  1..9
                        mol_type = protein
                        organism = Morganella morganii
SEQUENCE: 246
HTGYVGGIK                                                         9

SEQ ID NO: 247          moltype = AA  length = 8
FEATURE                 Location/Qualifiers
source                  1..8
                        mol_type = protein
                        organism = Morganella morganii
```

```
SEQUENCE: 247
VSEGQIVR                                                        8

SEQ ID NO: 248          moltype = AA  length = 8
FEATURE                 Location/Qualifiers
source                  1..8
                        mol_type = protein
                        organism = Morganella morganii
SEQUENCE: 248
ANLAAQIK                                                        8

SEQ ID NO: 249          moltype = AA  length = 16
FEATURE                 Location/Qualifiers
source                  1..16
                        mol_type = protein
                        organism = Morganella morganii
SEQUENCE: 249
VGTVTPNVAE AVNNAK                                               16

SEQ ID NO: 250          moltype = AA  length = 13
FEATURE                 Location/Qualifiers
source                  1..13
                        mol_type = protein
                        organism = Morganella morganii
SEQUENCE: 250
AANVIGPQIE YAK                                                  13

SEQ ID NO: 251          moltype = AA  length = 8
FEATURE                 Location/Qualifiers
source                  1..8
                        mol_type = protein
                        organism = Morganella morganii
SEQUENCE: 251
SLENYFGR                                                        8

SEQ ID NO: 252          moltype = AA  length = 9
FEATURE                 Location/Qualifiers
source                  1..9
                        mol_type = protein
                        organism = Morganella morganii
SEQUENCE: 252
VFLSGELTR                                                       9

SEQ ID NO: 253          moltype = AA  length = 10
FEATURE                 Location/Qualifiers
source                  1..10
                        mol_type = protein
                        organism = Morganella morganii
SEQUENCE: 253
VEGVNTLLVK                                                      10

SEQ ID NO: 254          moltype = AA  length = 11
FEATURE                 Location/Qualifiers
source                  1..11
                        mol_type = protein
                        organism = Morganella morganii
SEQUENCE: 254
LYLGAVATSV R                                                    11

SEQ ID NO: 255          moltype = AA  length = 11
FEATURE                 Location/Qualifiers
source                  1..11
                        mol_type = protein
                        organism = Morganella morganii
SEQUENCE: 255
IGFFNPIAAG K                                                    11

SEQ ID NO: 256          moltype = AA  length = 14
FEATURE                 Location/Qualifiers
source                  1..14
                        mol_type = protein
                        organism = Morganella morganii
SEQUENCE: 256
TVPMFNDALA ELNK                                                 14

SEQ ID NO: 257          moltype = AA  length = 16
FEATURE                 Location/Qualifiers
source                  1..16
                        mol_type = protein
```

```
                        organism = Morganella morganii
SEQUENCE: 257
ALVNAMVVGV TEGFSK                                                      16

SEQ ID NO: 258          moltype = AA  length = 12
FEATURE                 Location/Qualifiers
source                  1..12
                        mol_type = protein
                        organism = Morganella morganii
SEQUENCE: 258
LYDINEAVAL LK                                                          12

SEQ ID NO: 259          moltype = AA  length = 14
FEATURE                 Location/Qualifiers
source                  1..14
                        mol_type = protein
                        organism = Morganella morganii
SEQUENCE: 259
GNTGENLLSL LEGR                                                        14

SEQ ID NO: 260          moltype = AA  length = 15
FEATURE                 Location/Qualifiers
source                  1..15
                        mol_type = protein
                        organism = Morganella morganii
SEQUENCE: 260
DVTAIDPVSL IAFGK                                                       15

SEQ ID NO: 261          moltype = AA  length = 11
FEATURE                 Location/Qualifiers
source                  1..11
                        mol_type = protein
                        organism = Morganella morganii
SEQUENCE: 261
ALLSAFNFPF R                                                           11

SEQ ID NO: 262          moltype = AA  length = 8
FEATURE                 Location/Qualifiers
source                  1..8
                        mol_type = protein
                        organism = Morganella morganii
SEQUENCE: 262
GTVVAIDK                                                               8

SEQ ID NO: 263          moltype = AA  length = 11
FEATURE                 Location/Qualifiers
source                  1..11
                        mol_type = protein
                        organism = Morganella morganii
SEQUENCE: 263
GATVLPNGTG R                                                           11

SEQ ID NO: 264          moltype = AA  length = 8
FEATURE                 Location/Qualifiers
source                  1..8
                        mol_type = protein
                        organism = Morganella morganii
SEQUENCE: 264
AGNALPMR                                                               8

SEQ ID NO: 265          moltype = AA  length = 13
FEATURE                 Location/Qualifiers
source                  1..13
                        mol_type = protein
                        organism = Neisseria meningitidis
SEQUENCE: 265
SGSNVEAAAI VGK                                                         13

SEQ ID NO: 266          moltype = AA  length = 17
FEATURE                 Location/Qualifiers
source                  1..17
                        mol_type = protein
                        organism = Neisseria meningitidis
SEQUENCE: 266
MFLNTIQPAV GATHAGR                                                     17

SEQ ID NO: 267          moltype = AA  length = 11
FEATURE                 Location/Qualifiers
source                  1..11
```

```
                         mol_type = protein
                         organism = Neisseria meningitidis
SEQUENCE: 267
GLIEFALTEE K                                                         11

SEQ ID NO: 268           moltype = AA  length = 18
FEATURE                  Location/Qualifiers
source                   1..18
                         mol_type = protein
                         organism = Neisseria meningitidis
SEQUENCE: 268
DLQVLMGVPV HVNIEEIR                                                  18

SEQ ID NO: 269           moltype = AA  length = 12
FEATURE                  Location/Qualifiers
source                   1..12
                         mol_type = protein
                         organism = Neisseria meningitidis
SEQUENCE: 269
AGMATILSQL TR                                                        12

SEQ ID NO: 270           moltype = AA  length = 10
FEATURE                  Location/Qualifiers
source                   1..10
                         mol_type = protein
                         organism = Neisseria meningitidis
SEQUENCE: 270
SWVVSELVEK                                                           10

SEQ ID NO: 271           moltype = AA  length = 8
FEATURE                  Location/Qualifiers
source                   1..8
                         mol_type = protein
                         organism = Ochrobactrum anthropi
SEQUENCE: 271
TAFIALIR                                                             8

SEQ ID NO: 272           moltype = AA  length = 12
FEATURE                  Location/Qualifiers
source                   1..12
                         mol_type = protein
                         organism = Ochrobactrum anthropi
SEQUENCE: 272
VLDVLQSEGY IR                                                        12

SEQ ID NO: 273           moltype = AA  length = 8
FEATURE                  Location/Qualifiers
source                   1..8
                         mol_type = protein
                         organism = Ochrobactrum anthropi
SEQUENCE: 273
FITIALPR                                                             8

SEQ ID NO: 274           moltype = AA  length = 12
FEATURE                  Location/Qualifiers
source                   1..12
                         mol_type = protein
                         organism = Pantoea agglomerans
SEQUENCE: 274
APVVVPAGVE VK                                                        12

SEQ ID NO: 275           moltype = AA  length = 8
FEATURE                  Location/Qualifiers
source                   1..8
                         mol_type = protein
                         organism = Pantoea agglomerans
SEQUENCE: 275
EGSYVTLR                                                             8

SEQ ID NO: 276           moltype = AA  length = 14
FEATURE                  Location/Qualifiers
source                   1..14
                         mol_type = protein
                         organism = Pantoea agglomerans
SEQUENCE: 276
GLPTPVVITV YSDR                                                      14

SEQ ID NO: 277           moltype = AA  length = 11
FEATURE                  Location/Qualifiers
```

-continued

```
source                  1..11
                        mol_type = protein
                        organism = Pantoea agglomerans
SEQUENCE: 277
QPLELLDLVG K                                                              11

SEQ ID NO: 278          moltype = AA  length = 13
FEATURE                 Location/Qualifiers
source                  1..13
                        mol_type = protein
                        organism = Parvimonas micra
SEQUENCE: 278
ILDALTIDAF STK                                                            13

SEQ ID NO: 279          moltype = AA  length = 13
FEATURE                 Location/Qualifiers
source                  1..13
                        mol_type = protein
                        organism = Parvimonas micra
SEQUENCE: 279
ITGDALVMML ETR                                                            13

SEQ ID NO: 280          moltype = AA  length = 14
FEATURE                 Location/Qualifiers
source                  1..14
                        mol_type = protein
                        organism = Parvimonas micra
SEQUENCE: 280
VLFEMSGVPV DVAR                                                           14

SEQ ID NO: 281          moltype = AA  length = 11
FEATURE                 Location/Qualifiers
source                  1..11
                        mol_type = protein
                        organism = Parvimonas micra
SEQUENCE: 281
ALLELLGMPF K                                                              11

SEQ ID NO: 282          moltype = AA  length = 12
FEATURE                 Location/Qualifiers
source                  1..12
                        mol_type = protein
                        organism = Proteus mirabilis
SEQUENCE: 282
QYEINEAVAL LK                                                             12

SEQ ID NO: 283          moltype = AA  length = 9
FEATURE                 Location/Qualifiers
source                  1..9
                        mol_type = protein
                        organism = Proteus mirabilis
SEQUENCE: 283
EAFQLAAAK                                                                 9

SEQ ID NO: 284          moltype = AA  length = 9
FEATURE                 Location/Qualifiers
source                  1..9
                        mol_type = protein
                        organism = Proteus mirabilis
SEQUENCE: 284
VDFNEAQLK                                                                 9

SEQ ID NO: 285          moltype = AA  length = 7
FEATURE                 Location/Qualifiers
source                  1..7
                        mol_type = protein
                        organism = Proteus mirabilis
SEQUENCE: 285
IVAEFGR                                                                   7

SEQ ID NO: 286          moltype = AA  length = 9
FEATURE                 Location/Qualifiers
source                  1..9
                        mol_type = protein
                        organism = Proteus mirabilis
SEQUENCE: 286
ATMAGLGLR                                                                 9

SEQ ID NO: 287          moltype = AA  length = 13
```

-continued

```
FEATURE               Location/Qualifiers
source                1..13
                      mol_type = protein
                      organism = Proteus vulgaris
SEQUENCE: 287
LATLPTYDEA IAR                                                    13

SEQ ID NO: 288        moltype = AA  length = 12
FEATURE               Location/Qualifiers
source                1..12
                      mol_type = protein
                      organism = Proteus vulgaris
SEQUENCE: 288
QYEITEAVAL LK                                                     12

SEQ ID NO: 289        moltype = AA  length = 9
FEATURE               Location/Qualifiers
source                1..9
                      mol_type = protein
                      organism = Proteus vulgaris
SEQUENCE: 289
VDFNETQLK                                                         9

SEQ ID NO: 290        moltype = AA  length = 11
FEATURE               Location/Qualifiers
source                1..11
                      mol_type = protein
                      organism = Pseudomonas aeruginosa
SEQUENCE: 290
AALSAVVADA R                                                      11

SEQ ID NO: 291        moltype = AA  length = 12
FEATURE               Location/Qualifiers
source                1..12
                      mol_type = protein
                      organism = Pseudomonas aeruginosa
SEQUENCE: 291
IIQQIEAEQM NK                                                     12

SEQ ID NO: 292        moltype = AA  length = 8
FEATURE               Location/Qualifiers
source                1..8
                      mol_type = protein
                      organism = Pseudomonas aeruginosa
SEQUENCE: 292
LPAGVEIK                                                          8

SEQ ID NO: 293        moltype = AA  length = 15
FEATURE               Location/Qualifiers
source                1..15
                      mol_type = protein
                      organism = Pseudomonas aeruginosa
SEQUENCE: 293
VHPSVEVIQD SGELR                                                  15

SEQ ID NO: 294        moltype = AA  length = 7
FEATURE               Location/Qualifiers
source                1..7
                      mol_type = protein
                      organism = Pseudomonas aeruginosa
SEQUENCE: 294
YTALIGR                                                           7

SEQ ID NO: 295        moltype = AA  length = 9
FEATURE               Location/Qualifiers
source                1..9
                      mol_type = protein
                      organism = Pseudomonas aeruginosa
SEQUENCE: 295
STPAAVLLK                                                         9

SEQ ID NO: 296        moltype = AA  length = 12
FEATURE               Location/Qualifiers
source                1..12
                      mol_type = protein
                      organism = Pseudomonas aeruginosa
SEQUENCE: 296
VEGDVVSLQT LK                                                     12
```

-continued

```
SEQ ID NO: 297          moltype = AA  length = 10
FEATURE                 Location/Qualifiers
source                  1..10
                        mol_type = protein
                        organism = Pseudomonas aeruginosa
SEQUENCE: 297
IGLPVVEGAK                                                            10

SEQ ID NO: 298          moltype = AA  length = 10
FEATURE                 Location/Qualifiers
source                  1..10
                        mol_type = protein
                        organism = Pseudomonas aeruginosa
SEQUENCE: 298
VTVQSLEIVR                                                            10

SEQ ID NO: 299          moltype = AA  length = 10
FEATURE                 Location/Qualifiers
source                  1..10
                        mol_type = protein
                        organism = Pseudomonas aeruginosa
SEQUENCE: 299
LVVGGVNLIK                                                            10

SEQ ID NO: 300          moltype = AA  length = 8
FEATURE                 Location/Qualifiers
source                  1..8
                        mol_type = protein
                        organism = Pseudomonas aeruginosa
SEQUENCE: 300
AGDVVAVR                                                              8

SEQ ID NO: 301          moltype = AA  length = 9
FEATURE                 Location/Qualifiers
source                  1..9
                        mol_type = protein
                        organism = Pseudomonas oryzihabitans
SEQUENCE: 301
TVLNQQAGK                                                             9

SEQ ID NO: 302          moltype = AA  length = 8
FEATURE                 Location/Qualifiers
source                  1..8
                        mol_type = protein
                        organism = Pseudomonas oryzihabitans
SEQUENCE: 302
STGEVHLR                                                              8

SEQ ID NO: 303          moltype = AA  length = 11
FEATURE                 Location/Qualifiers
source                  1..11
                        mol_type = protein
                        organism = Pseudomonas oryzihabitans
SEQUENCE: 303
SVLEAENSAE R                                                          11

SEQ ID NO: 304          moltype = AA  length = 12
FEATURE                 Location/Qualifiers
source                  1..12
                        mol_type = protein
                        organism = Pseudomonas oryzihabitans
SEQUENCE: 304
ALDAIAPLVE VK                                                         12

SEQ ID NO: 305          moltype = AA  length = 7
FEATURE                 Location/Qualifiers
source                  1..7
                        mol_type = protein
                        organism = Pseudomonas oryzihabitans
SEQUENCE: 305
FGFVSLK                                                               7

SEQ ID NO: 306          moltype = AA  length = 16
FEATURE                 Location/Qualifiers
source                  1..16
                        mol_type = protein
                        organism = Raoultella ornithinolytica
SEQUENCE: 306
ALLNSVVIGV TEGFTK                                                     16
```

-continued

```
SEQ ID NO: 307          moltype = AA  length = 8
FEATURE                 Location/Qualifiers
source                  1..8
                        mol_type = protein
                        organism = Raoultella ornithinolytica
SEQUENCE: 307
SATGLGLK                                                                    8

SEQ ID NO: 308          moltype = AA  length = 12
FEATURE                 Location/Qualifiers
source                  1..12
                        mol_type = protein
                        organism = Rothia dentocariosa
SEQUENCE: 308
QAQEVIAEQA TR                                                               12

SEQ ID NO: 309          moltype = AA  length = 15
FEATURE                 Location/Qualifiers
source                  1..15
                        mol_type = protein
                        organism = Rothia dentocariosa
SEQUENCE: 309
AHETLAATGV NPDTR                                                            15

SEQ ID NO: 310          moltype = AA  length = 8
FEATURE                 Location/Qualifiers
source                  1..8
                        mol_type = protein
                        organism = Rothia dentocariosa
SEQUENCE: 310
HIMVDGVR                                                                    8

SEQ ID NO: 311          moltype = AA  length = 11
FEATURE                 Location/Qualifiers
source                  1..11
                        mol_type = protein
                        organism = Rothia dentocariosa
SEQUENCE: 311
IVYGALEGVE K                                                                11

SEQ ID NO: 312          moltype = AA  length = 13
FEATURE                 Location/Qualifiers
source                  1..13
                        mol_type = protein
                        organism = Rothia dentocariosa
SEQUENCE: 312
AEAAEEPMAA WER                                                              13

SEQ ID NO: 313          moltype = AA  length = 10
FEATURE                 Location/Qualifiers
source                  1..10
                        mol_type = protein
                        organism = Rothia dentocariosa
SEQUENCE: 313
LIDVVDPTPK                                                                  10

SEQ ID NO: 314          moltype = AA  length = 8
FEATURE                 Location/Qualifiers
source                  1..8
                        mol_type = protein
                        organism = Rothia dentocariosa
SEQUENCE: 314
IIDIDMDR                                                                    8

SEQ ID NO: 315          moltype = AA  length = 10
FEATURE                 Location/Qualifiers
source                  1..10
                        mol_type = protein
                        organism = Rothia dentocariosa
SEQUENCE: 315
VLNLNESVMR                                                                  10

SEQ ID NO: 316          moltype = AA  length = 12
FEATURE                 Location/Qualifiers
source                  1..12
                        mol_type = protein
                        organism = Rothia dentocariosa
SEQUENCE: 316
```

```
ELSLVEVSEF VK                                                12

SEQ ID NO: 317          moltype = AA  length = 18
FEATURE                 Location/Qualifiers
source                  1..18
                        mol_type = protein
                        organism = Rothia dentocariosa
SEQUENCE: 317
TADPVTVGMV NTVAHLVK                                          18

SEQ ID NO: 318          moltype = AA  length = 11
FEATURE                 Location/Qualifiers
source                  1..11
                        mol_type = protein
                        organism = Rothia dentocariosa
SEQUENCE: 318
LSIEELIAAF K                                                 11

SEQ ID NO: 319          moltype = AA  length = 12
FEATURE                 Location/Qualifiers
source                  1..12
                        mol_type = protein
                        organism = Rothia dentocariosa
SEQUENCE: 319
GSVILPEAIT PK                                                12

SEQ ID NO: 320          moltype = AA  length = 15
FEATURE                 Location/Qualifiers
source                  1..15
                        mol_type = protein
                        organism = Salmonella enterica
SEQUENCE: 320
DIADAVTAAG VDVAK                                             15

SEQ ID NO: 321          moltype = AA  length = 14
FEATURE                 Location/Qualifiers
source                  1..14
                        mol_type = protein
                        organism = Salmonella enterica
SEQUENCE: 321
VAVFTQGPNA EAAK                                              14

SEQ ID NO: 322          moltype = AA  length = 8
FEATURE                 Location/Qualifiers
source                  1..8
                        mol_type = protein
                        organism = Serratia marcescens
SEQUENCE: 322
SLDTDGYR                                                     8

SEQ ID NO: 323          moltype = AA  length = 9
FEATURE                 Location/Qualifiers
source                  1..9
                        mol_type = protein
                        organism = Serratia marcescens
SEQUENCE: 323
TIHDAVEVK                                                    9

SEQ ID NO: 324          moltype = AA  length = 12
FEATURE                 Location/Qualifiers
source                  1..12
                        mol_type = protein
                        organism = Serratia marcescens
SEQUENCE: 324
INELGSVTIA SK                                                12

SEQ ID NO: 325          moltype = AA  length = 11
FEATURE                 Location/Qualifiers
source                  1..11
                        mol_type = protein
                        organism = Serratia marcescens
SEQUENCE: 325
QEANALTFAP R                                                 11

SEQ ID NO: 326          moltype = AA  length = 15
FEATURE                 Location/Qualifiers
source                  1..15
                        mol_type = protein
                        organism = Serratia marcescens
```

```
SEQUENCE: 326
DVAGIDPVSL IAFDK                                            15

SEQ ID NO: 327          moltype = AA  length = 8
FEATURE                 Location/Qualifiers
source                  1..8
                        mol_type = protein
                        organism = Serratia marcescens
SEQUENCE: 327
DGSYVTLR                                                    8

SEQ ID NO: 328          moltype = AA  length = 15
FEATURE                 Location/Qualifiers
source                  1..15
                        mol_type = protein
                        organism = Staphylococcus aureus
SEQUENCE: 328
SGVMEGNVIT AEEVK                                            15

SEQ ID NO: 329          moltype = AA  length = 19
FEATURE                 Location/Qualifiers
source                  1..19
                        mol_type = protein
                        organism = Staphylococcus aureus
SEQUENCE: 329
IIEQIGTYNP TSANAPEIK                                        19

SEQ ID NO: 330          moltype = AA  length = 9
FEATURE                 Location/Qualifiers
source                  1..9
                        mol_type = protein
                        organism = Staphylococcus aureus
SEQUENCE: 330
SQSVLVFAK                                                   9

SEQ ID NO: 331          moltype = AA  length = 10
FEATURE                 Location/Qualifiers
source                  1..10
                        mol_type = protein
                        organism = Staphylococcus aureus
SEQUENCE: 331
VLELVGVGYR                                                  10

SEQ ID NO: 332          moltype = AA  length = 10
FEATURE                 Location/Qualifiers
source                  1..10
                        mol_type = protein
                        organism = Staphylococcus aureus
SEQUENCE: 332
MAVEEIFNVK                                                  10

SEQ ID NO: 333          moltype = AA  length = 12
FEATURE                 Location/Qualifiers
source                  1..12
                        mol_type = protein
                        organism = Staphylococcus aureus
SEQUENCE: 333
NYAVEATPGN LK                                               12

SEQ ID NO: 334          moltype = AA  length = 7
FEATURE                 Location/Qualifiers
source                  1..7
                        mol_type = protein
                        organism = Staphylococcus aureus
SEQUENCE: 334
AGIDINR                                                     7

SEQ ID NO: 335          moltype = AA  length = 10
FEATURE                 Location/Qualifiers
source                  1..10
                        mol_type = protein
                        organism = Staphylococcus aureus
SEQUENCE: 335
VVVEGVNIMK                                                  10

SEQ ID NO: 336          moltype = AA  length = 12
FEATURE                 Location/Qualifiers
source                  1..12
                        mol_type = protein
```

```
                        organism = Staphylococcus aureus
SEQUENCE: 336
ILEEANVSAD TR                                                      12

SEQ ID NO: 337          moltype = AA  length = 8
FEATURE                 Location/Qualifiers
source                  1..8
                        mol_type = protein
                        organism = Staphylococcus aureus
SEQUENCE: 337
VDEALALK                                                           8

SEQ ID NO: 338          moltype = AA  length = 14
FEATURE                 Location/Qualifiers
source                  1..14
                        mol_type = protein
                        organism = Staphylococcus coagulase negative
SEQUENCE: 338
AVLELAGITD ILSK                                                    14

SEQ ID NO: 339          moltype = AA  length = 11
FEATURE                 Location/Qualifiers
source                  1..11
                        mol_type = protein
                        organism = Staphylococcus coagulase negative
SEQUENCE: 339
VIFLDTTTDF K                                                       11

SEQ ID NO: 340          moltype = AA  length = 10
FEATURE                 Location/Qualifiers
source                  1..10
                        mol_type = protein
                        organism = Staphylococcus coagulase negative
SEQUENCE: 340
MFAIIETGGK                                                         10

SEQ ID NO: 341          moltype = AA  length = 8
FEATURE                 Location/Qualifiers
source                  1..8
                        mol_type = protein
                        organism = Staphylococcus coagulase negative
SEQUENCE: 341
IDEELALK                                                           8

SEQ ID NO: 342          moltype = AA  length = 8
FEATURE                 Location/Qualifiers
source                  1..8
                        mol_type = protein
                        organism = Staphylococcus coagulase negative
SEQUENCE: 342
SLLQPLPK                                                           8

SEQ ID NO: 343          moltype = AA  length = 11
FEATURE                 Location/Qualifiers
source                  1..11
                        mol_type = protein
                        organism = Staphylococcus pettenkorferi
SEQUENCE: 343
VIFLDTTTNY K                                                       11

SEQ ID NO: 344          moltype = AA  length = 11
FEATURE                 Location/Qualifiers
source                  1..11
                        mol_type = protein
                        organism = Staphylococcus saprophyticus
SEQUENCE: 344
ALINNMIQGV K                                                       11

SEQ ID NO: 345          moltype = AA  length = 10
FEATURE                 Location/Qualifiers
source                  1..10
                        mol_type = protein
                        organism = Staphylococcus saprophyticus
SEQUENCE: 345
ILYSAFDLVK                                                         10

SEQ ID NO: 346          moltype = AA  length = 12
FEATURE                 Location/Qualifiers
source                  1..12
```

-continued

```
                        mol_type = protein
                        organism = Stenotrophomonas maltophilia
SEQUENCE: 346
AYAFEDAINI LK                                                        12

SEQ ID NO: 347          moltype = AA  length = 15
FEATURE                 Location/Qualifiers
source                  1..15
                        mol_type = protein
                        organism = Stenotrophomonas maltophilia
SEQUENCE: 347
DFSEDLVHQV VVAYR                                                     15

SEQ ID NO: 348          moltype = AA  length = 12
FEATURE                 Location/Qualifiers
source                  1..12
                        mol_type = protein
                        organism = Stenotrophomonas maltophilia
SEQUENCE: 348
DTAEVLLYAL DK                                                        12

SEQ ID NO: 349          moltype = AA  length = 9
FEATURE                 Location/Qualifiers
source                  1..9
                        mol_type = protein
                        organism = Streptococcus agalactiae
SEQUENCE: 349
TQLESETTR                                                            9

SEQ ID NO: 350          moltype = AA  length = 8
FEATURE                 Location/Qualifiers
source                  1..8
                        mol_type = protein
                        organism = Streptococcus agalactiae
SEQUENCE: 350
GQVPGVTK                                                             8

SEQ ID NO: 351          moltype = AA  length = 12
FEATURE                 Location/Qualifiers
source                  1..12
                        mol_type = protein
                        organism = Streptococcus agalactiae
SEQUENCE: 351
EGASEAEANE IK                                                        12

SEQ ID NO: 352          moltype = AA  length = 9
FEATURE                 Location/Qualifiers
source                  1..9
                        mol_type = protein
                        organism = Streptococcus agalactiae
SEQUENCE: 352
SMVALEAGK                                                            9

SEQ ID NO: 353          moltype = AA  length = 11
FEATURE                 Location/Qualifiers
source                  1..11
                        mol_type = protein
                        organism = Streptococcus agalactiae
SEQUENCE: 353
GLTVEQDTNL R                                                         11

SEQ ID NO: 354          moltype = AA  length = 12
FEATURE                 Location/Qualifiers
source                  1..12
                        mol_type = protein
                        organism = Streptococcus agalactiae
SEQUENCE: 354
FTSVEEINAL AK                                                        12

SEQ ID NO: 355          moltype = AA  length = 11
FEATURE                 Location/Qualifiers
source                  1..11
                        mol_type = protein
                        organism = Streptococcus agalactiae
SEQUENCE: 355
LEAAGASVTL K                                                         11

SEQ ID NO: 356          moltype = AA  length = 12
FEATURE                 Location/Qualifiers
```

```
source                  1..12
                        mol_type = protein
                        organism = Streptococcus agalactiae
SEQUENCE: 356
DVLSAGQEVT VK                                                      12

SEQ ID NO: 357          moltype = AA  length = 11
FEATURE                 Location/Qualifiers
source                  1..11
                        mol_type = protein
                        organism = Streptococcus agalactiae
SEQUENCE: 357
AIVDNAPSVI K                                                       11

SEQ ID NO: 358          moltype = AA  length = 12
FEATURE                 Location/Qualifiers
source                  1..12
                        mol_type = protein
                        organism = Streptococcus agalactiae
SEQUENCE: 358
GTHIYPGANV GR                                                      12

SEQ ID NO: 359          moltype = AA  length = 7
FEATURE                 Location/Qualifiers
source                  1..7
                        mol_type = protein
                        organism = Streptococcus agalactiae
SEQUENCE: 359
SDIPEFR                                                            7

SEQ ID NO: 360          moltype = AA  length = 10
FEATURE                 Location/Qualifiers
source                  1..10
                        mol_type = protein
                        organism = Streptococcus bovis
SEQUENCE: 360
FDETTGDYSR                                                         10

SEQ ID NO: 361          moltype = AA  length = 8
FEATURE                 Location/Qualifiers
source                  1..8
                        mol_type = protein
                        organism = Streptococcus bovis
SEQUENCE: 361
AEDVAALR                                                           8

SEQ ID NO: 362          moltype = AA  length = 16
FEATURE                 Location/Qualifiers
source                  1..16
                        mol_type = protein
                        organism = Streptococcus bovis
SEQUENCE: 362
TAEFANVLSA LNVDSK                                                  16

SEQ ID NO: 363          moltype = AA  length = 15
FEATURE                 Location/Qualifiers
source                  1..15
                        mol_type = protein
                        organism = Streptococcus bovis
SEQUENCE: 363
GTAASIVYDA FEQIK                                                   15

SEQ ID NO: 364          moltype = AA  length = 7
FEATURE                 Location/Qualifiers
source                  1..7
                        mol_type = protein
                        organism = Streptococcus bovis
SEQUENCE: 364
LTAPSVK                                                            7

SEQ ID NO: 365          moltype = AA  length = 9
FEATURE                 Location/Qualifiers
source                  1..9
                        mol_type = protein
                        organism = Streptococcus bovis
SEQUENCE: 365
TVAALGLGK                                                          9

SEQ ID NO: 366          moltype = AA  length = 13
```

-continued

```
FEATURE                  Location/Qualifiers
source                   1..13
                         mol_type = protein
                         organism = Streptococcus bovis
SEQUENCE: 366
FIQTELADAS VSR                                                     13

SEQ ID NO: 367           moltype = AA  length = 8
FEATURE                  Location/Qualifiers
source                   1..8
                         mol_type = protein
                         organism = Streptococcus bovis
SEQUENCE: 367
EVVPAENR                                                           8

SEQ ID NO: 368           moltype = AA  length = 14
FEATURE                  Location/Qualifiers
source                   1..14
                         mol_type = protein
                         organism = Streptococcus bovis
SEQUENCE: 368
NEIASENFDE ATEK                                                    14

SEQ ID NO: 369           moltype = AA  length = 10
FEATURE                  Location/Qualifiers
source                   1..10
                         mol_type = protein
                         organism = Streptococcus bovis
SEQUENCE: 369
IAGVDIPNEK                                                         10

SEQ ID NO: 370           moltype = AA  length = 8
FEATURE                  Location/Qualifiers
source                   1..8
                         mol_type = protein
                         organism = Streptococcccus common
SEQUENCE: 370
DFHGVPTK                                                           8

SEQ ID NO: 371           moltype = AA  length = 13
FEATURE                  Location/Qualifiers
source                   1..13
                         mol_type = protein
                         organism = Streptococccus common
SEQUENCE: 371
NGIHVIDLQQ TVK                                                     13

SEQ ID NO: 372           moltype = AA  length = 6
FEATURE                  Location/Qualifiers
source                   1..6
                         mol_type = protein
                         organism = Streptococcus common
SEQUENCE: 372
VLVFAR                                                             6

SEQ ID NO: 373           moltype = AA  length = 12
FEATURE                  Location/Qualifiers
source                   1..12
                         mol_type = protein
                         organism = Streptococcus common
SEQUENCE: 373
SLGSNTPINI VR                                                      12

SEQ ID NO: 374           moltype = AA  length = 7
FEATURE                  Location/Qualifiers
source                   1..7
                         mol_type = protein
                         organism = Streptococcus common
SEQUENCE: 374
MIEGTAR                                                            7

SEQ ID NO: 375           moltype = AA  length = 7
FEATURE                  Location/Qualifiers
source                   1..7
                         mol_type = protein
                         organism = Streptococcus common
SEQUENCE: 375
INVADSR                                                            7
```

```
SEQ ID NO: 376          moltype = AA  length = 10
FEATURE                 Location/Qualifiers
source                  1..10
                        mol_type = protein
                        organism = Streptococcus common
SEQUENCE: 376
AIITLTADSK                                                                10

SEQ ID NO: 377          moltype = AA  length = 7
FEATURE                 Location/Qualifiers
source                  1..7
                        mol_type = protein
                        organism = Streptococcus common
SEQUENCE: 377
LGLATTR                                                                   7

SEQ ID NO: 378          moltype = AA  length = 10
FEATURE                 Location/Qualifiers
source                  1..10
                        mol_type = protein
                        organism = Streptococcus dysgalactiae
SEQUENCE: 378
VEAGQVISVR                                                                10

SEQ ID NO: 379          moltype = AA  length = 7
FEATURE                 Location/Qualifiers
source                  1..7
                        mol_type = protein
                        organism = Streptococcus dysgalactiae
SEQUENCE: 379
VINDFAK                                                                   7

SEQ ID NO: 380          moltype = AA  length = 10
FEATURE                 Location/Qualifiers
source                  1..10
                        mol_type = protein
                        organism = Streptococcus dysgalactiae
SEQUENCE: 380
VVVEGVGMIK                                                                10

SEQ ID NO: 381          moltype = AA  length = 7
FEATURE                 Location/Qualifiers
source                  1..7
                        mol_type = protein
                        organism = Streptococcus dysgalactiae
SEQUENCE: 381
VLEWLAK                                                                   7

SEQ ID NO: 382          moltype = AA  length = 15
FEATURE                 Location/Qualifiers
source                  1..15
                        mol_type = protein
                        organism = Streptococcus other streptococcus
SEQUENCE: 382
AADGQTVTGG SILYR                                                          15

SEQ ID NO: 383          moltype = AA  length = 11
FEATURE                 Location/Qualifiers
source                  1..11
                        mol_type = protein
                        organism = Streptococcus other streptococcus
SEQUENCE: 383
QAVEAAFEGV K                                                              11

SEQ ID NO: 384          moltype = AA  length = 10
FEATURE                 Location/Qualifiers
source                  1..10
                        mol_type = protein
                        organism = Streptococcus other streptococcus
SEQUENCE: 384
IVSGPEADIK                                                                10

SEQ ID NO: 385          moltype = AA  length = 13
FEATURE                 Location/Qualifiers
source                  1..13
                        mol_type = protein
                        organism = Streptococcus other streptococcus
SEQUENCE: 385
FVAVDSLSFT APK                                                            13
```

-continued

```
SEQ ID NO: 386          moltype = AA  length = 11
FEATURE                 Location/Qualifiers
source                  1..11
                        mol_type = protein
                        organism = Streptococcus other streptococcus
SEQUENCE: 386
IQIFEGVVIA R                                                            11

SEQ ID NO: 387          moltype = AA  length = 10
FEATURE                 Location/Qualifiers
source                  1..10
                        mol_type = protein
                        organism = Streptococcus pneumoniae
SEQUENCE: 387
AAGDYEGLSK                                                              10

SEQ ID NO: 388          moltype = AA  length = 9
FEATURE                 Location/Qualifiers
source                  1..9
                        mol_type = protein
                        organism = Streptococcus pneumoniae
SEQUENCE: 388
FVGQEFDTK                                                               9

SEQ ID NO: 389          moltype = AA  length = 9
FEATURE                 Location/Qualifiers
source                  1..9
                        mol_type = protein
                        organism = Streptococcus pyogenes
SEQUENCE: 389
SAEAAIIAK                                                               9

SEQ ID NO: 390          moltype = AA  length = 10
FEATURE                 Location/Qualifiers
source                  1..10
                        mol_type = protein
                        organism = Streptococcus pyogenes
SEQUENCE: 390
VDPGQVISVR                                                              10

SEQ ID NO: 391          moltype = AA  length = 7
FEATURE                 Location/Qualifiers
source                  1..7
                        mol_type = protein
                        organism = Streptococcus pyogenes
SEQUENCE: 391
VINDFTK                                                                 7

SEQ ID NO: 392          moltype = AA  length = 10
FEATURE                 Location/Qualifiers
source                  1..10
                        mol_type = protein
                        organism = Streptococcus pyogenes
SEQUENCE: 392
VIVEGVGMIK                                                              10

SEQ ID NO: 393          moltype = AA  length = 14
FEATURE                 Location/Qualifiers
source                  1..14
                        mol_type = protein
                        organism = Citrobacter amalonaticus
SEQUENCE: 393
AADMTGADIE AMTR                                                         14

SEQ ID NO: 394          moltype = AA  length = 11
FEATURE                 Location/Qualifiers
source                  1..11
                        mol_type = protein
                        organism = Citrobacter amalonaticus
SEQUENCE: 394
LADVLAAANA R                                                            11

SEQ ID NO: 395          moltype = AA  length = 12
FEATURE                 Location/Qualifiers
source                  1..12
                        mol_type = protein
                        organism = Citrobacter amalonaticus
SEQUENCE: 395
```

```
INALETVTIT SK                                                          12

SEQ ID NO: 396          moltype = AA  length = 9
FEATURE                 Location/Qualifiers
source                  1..9
                        mol_type = protein
                        organism = Bacteroides fragili
SEQUENCE: 396
MEVVNALGR                                                              9

SEQ ID NO: 397          moltype = AA  length = 10
FEATURE                 Location/Qualifiers
source                  1..10
                        mol_type = protein
                        organism = Bacteroides fragili
SEQUENCE: 397
YLTPPSVDVK                                                             10

SEQ ID NO: 398          moltype = AA  length = 14
FEATURE                 Location/Qualifiers
source                  1..14
                        mol_type = protein
                        organism = Citrobacter braakii
SEQUENCE: 398
YTAAITGAEG TIHR                                                        14

SEQ ID NO: 399          moltype = AA  length = 20
FEATURE                 Location/Qualifiers
source                  1..20
                        mol_type = protein
                        organism = Citrobacter braakii
SEQUENCE: 399
TLNDAVAVNH ADNALTFGPR                                                  20

SEQ ID NO: 400          moltype = AA  length = 14
FEATURE                 Location/Qualifiers
source                  1..14
                        mol_type = protein
                        organism = Citrobacter braakii
SEQUENCE: 400
AGDQVQSGVD AAIK                                                        14

SEQ ID NO: 401          moltype = AA  length = 14
FEATURE                 Location/Qualifiers
source                  1..14
                        mol_type = protein
                        organism = Klebsiella pneumoniae
SEQUENCE: 401
YTGAITAAAG TIHR                                                        14

SEQ ID NO: 402          moltype = AA  length = 9
FEATURE                 Location/Qualifiers
source                  1..9
                        mol_type = protein
                        organism = Proteus mirabilis
SEQUENCE: 402
AAFAALVEK                                                              9

SEQ ID NO: 403          moltype = AA  length = 8
FEATURE                 Location/Qualifiers
source                  1..8
                        mol_type = protein
                        organism = Proteus vulgari
SEQUENCE: 403
SIVVAIDR                                                               8

SEQ ID NO: 404          moltype = AA  length = 12
FEATURE                 Location/Qualifiers
source                  1..12
                        mol_type = protein
                        organism = Proteus vulgari
SEQUENCE: 404
INALGSVTIS SK                                                          12

SEQ ID NO: 405          moltype = AA  length = 13
FEATURE                 Location/Qualifiers
source                  1..13
                        mol_type = protein
                        organism = Providencia rettgeri
```

-continued

```
SEQUENCE: 405
AANVVGIQIE YAK                                                    13

SEQ ID NO: 406          moltype = AA  length = 14
FEATURE                 Location/Qualifiers
source                  1..14
                        mol_type = protein
                        organism = Providencia rettgeri
SEQUENCE: 406
AGDQIQSGVD SAIK                                                   14

SEQ ID NO: 407          moltype = AA  length = 11
FEATURE                 Location/Qualifiers
source                  1..11
                        mol_type = protein
                        organism = Providencia rettgeri
SEQUENCE: 407
DMVESAPATI K                                                      11

SEQ ID NO: 408          moltype = AA  length = 12
FEATURE                 Location/Qualifiers
source                  1..12
                        mol_type = protein
                        organism = Providencia rettgeri
SEQUENCE: 408
AAAFEGELIQ AK                                                     12

SEQ ID NO: 409          moltype = AA  length = 18
FEATURE                 Location/Qualifiers
source                  1..18
                        mol_type = protein
                        organism = Providencia rettgeri
SEQUENCE: 409
LSDFAAVEGD VIDLNALK                                               18

SEQ ID NO: 410          moltype = AA  length = 10
FEATURE                 Location/Qualifiers
source                  1..10
                        mol_type = protein
                        organism = Staphylococcus capitis
SEQUENCE: 410
SLELVGVGYR                                                        10

SEQ ID NO: 411          moltype = AA  length = 11
FEATURE                 Location/Qualifiers
source                  1..11
                        mol_type = protein
                        organism = Staphylococcus capitis
SEQUENCE: 411
YNSEVTENLV K                                                      11

SEQ ID NO: 412          moltype = AA  length = 15
FEATURE                 Location/Qualifiers
source                  1..15
                        mol_type = protein
                        organism = Staphylococcus capitis
SEQUENCE: 412
TGVMEGSVIS AEEVK                                                  15

SEQ ID NO: 413          moltype = AA  length = 15
FEATURE                 Location/Qualifiers
source                  1..15
                        mol_type = protein
                        organism = Staphylococcus capitis
SEQUENCE: 413
SGAEVSGPIP LPTEK                                                  15

SEQ ID NO: 414          moltype = AA  length = 8
FEATURE                 Location/Qualifiers
source                  1..8
                        mol_type = protein
                        organism = Staphylococcus capra
SEQUENCE: 414
ELVDNAPK                                                          8

SEQ ID NO: 415          moltype = AA  length = 13
FEATURE                 Location/Qualifiers
source                  1..13
                        mol_type = protein
```

```
                        organism = Staphylococcus epidermidis
SEQUENCE: 415
APGSVGMASD ASK                                                  13

SEQ ID NO: 416          moltype = AA  length = 18
FEATURE                 Location/Qualifiers
source                  1..18
                        mol_type = protein
                        organism = Staphylococcus epidermidis
SEQUENCE: 416
HIGSPNEVLE PGQQVNVK                                             18

SEQ ID NO: 417          moltype = AA  length = 10
FEATURE                 Location/Qualifiers
source                  1..10
                        mol_type = protein
                        organism = Staphylococcus epidermidis
SEQUENCE: 417
ILGIDEDNER                                                      10

SEQ ID NO: 418          moltype = AA  length = 9
FEATURE                 Location/Qualifiers
source                  1..9
                        mol_type = protein
                        organism = Staphylococcus hominis
SEQUENCE: 418
YYSVEEAIK                                                       9

SEQ ID NO: 419          moltype = AA  length = 14
FEATURE                 Location/Qualifiers
source                  1..14
                        mol_type = protein
                        organism = Staphylococcus hominis
SEQUENCE: 419
ILFEIAGVSE DVAR                                                 14

SEQ ID NO: 420          moltype = AA  length = 10
FEATURE                 Location/Qualifiers
source                  1..10
                        mol_type = protein
                        organism = Staphylococcus lugdunensis
SEQUENCE: 420
ILGVDEDNER                                                      10

SEQ ID NO: 421          moltype = AA  length = 11
FEATURE                 Location/Qualifiers
source                  1..11
                        mol_type = protein
                        organism = Staphylococcus lugdunensis
SEQUENCE: 421
VPAVVYGYST K                                                    11

SEQ ID NO: 422          moltype = AA  length = 11
FEATURE                 Location/Qualifiers
source                  1..11
                        mol_type = protein
                        organism = Proteus vulgaris
SEQUENCE: 422
LAETLAAAEA R                                                    11

SEQ ID NO: 423          moltype = AA  length = 11
FEATURE                 Location/Qualifiers
source                  1..11
                        mol_type = protein
                        organism = Proteus vulgaris
SEQUENCE: 423
LYLTAAATAV R                                                    11

SEQ ID NO: 424          moltype = AA  length = 8
FEATURE                 Location/Qualifiers
source                  1..8
                        mol_type = protein
                        organism = Sus scrofa
SEQUENCE: 424
NKPGVYTK                                                        8

SEQ ID NO: 425          moltype = AA  length = 8
FEATURE                 Location/Qualifiers
source                  1..8
```

-continued

```
                         mol_type = protein
                         organism = sus scrofa
SEQUENCE: 425
VATVSLPR                                                                  8

SEQ ID NO: 426           moltype = AA  length = 20
FEATURE                  Location/Qualifiers
source                   1..20
                         mol_type = protein
                         organism = Sus scrofa
SEQUENCE: 426
LGEHNIDVLE GNEQFINAAK                                                     20

SEQ ID NO: 427           moltype = AA  length = 20
FEATURE                  Location/Qualifiers
source                   1..20
                         mol_type = protein
                         organism = Sus scrofa
SEQUENCE: 427
IITHPNFNGN TLDNDIMLIK                                                     20

SEQ ID NO: 428           moltype = AA  length = 231
FEATURE                  Location/Qualifiers
source                   1..231
                         mol_type = protein
                         organism = Sus scrofa
SEQUENCE: 428
FPTDDDDKIV GGYTCAANSI PYQVSLNSGS HFCGGSLINS QWVVSAAHCY KSRIQVRLGE  60
HNIDVLEGNE QFINAAKIIT HPNFNGNTLD NDIMLIKLSS PATLNSRVAT VSLPRSCAAA  120
GTECLISGWG NTKSSGSSYP SLLQCLKAPV LSDSSCKSSY PGQITGNMIC VGFLEGGKDS  180
CQGDSGGPVV CNGQLQGIVS WGYGCAQKNK PGVYTKVCNY VNWIQQTIAA N           231
```

IDENTIFICATION OF MICROORGANISMS BASED ON IDENTIFICATION OF PEPTIDES USING A LIQUID SEPARATION DEVICE COUPLED WITH A MASS SPECTROMETER AND PROCESSING MEANS

CROSS-REFERENCE TO RELATED APPLICATIONS

This application is a U.S. National Stage Application pursuant to 35 U.S.C. § 371 of International Patent Application PCT/EP2022/069857, filed on Jul. 15, 2022, and published as WO 2023/285653 on Jan. 19, 2023, which claims priority to European Patent Application 21305988.4, filed on Jul. 15, 2021, all of which are incorporated herein by reference in their entireties for all purposes.

FIELD OF THE INVENTION

The present invention relates to a method for identifying microorganisms in a sample, in particular in a biological sample such as a blood sample from a Human being. This method may be used for the detection of septicemia, i.e., blood infections.

BACKGROUND OF THE INVENTION

The identification of microorganisms responsible for an infection is an essential step in the management of a patient. The rapid access to this identification information is all the more important in the case of symptomatic blood bacteremia induced by the continuous diffusion of pathogens from an infectious site, which can then lead to a sepsis syndrome. From mild then to severe, sepsis can ultimately evolve to a septic shock with which is associated up to 80% mortality.

The rapid identification of the pathogen(s) responsible for the bacteremia is thus a key step to be able to orient the choice of antibiotic therapy, or to proceed to de-escalation of the initial broad spectrum antimicrobial therapy. The expected consequences of such a rapid diagnosis is to reduce the therapeutic side effects in the patient, but also to contain the contribution of antibiotics use to the emergence of new antimicrobial resistant strains or mechanisms.

In other fields than human health, rapid identification of microorganisms present in a sample is also a key factor for adapting the anti-microbial strategy.

Two types of techniques have emerged over the last two decades that have revolutionized microbiological identification, by allowing a singularly shortened identification time compared to previously-used biochemical techniques. These are Maldi-Tof mass spectrometry and molecular biology-based tools.

The principle of pathogen identification by Maldi-Tof (Matrix-assisted laser desorption ionization-Time of flight) mass spectrometry is based on the comparison between an experimental mass spectrum of a fingerprint of low molecular weight proteins released by the lysis of the microbe of interest and a database containing tens of thousands of mass spectra of fingerprints obtained from strains of known microbes. A concordance score is then established to identify the genus of the pathogen or the genus and species of the pathogen. The principle of identification of a microbe by Maldi-Tof was first described in 1999 (Holland et al., 1999) for low molecular weight proteins.

Then the technique was widely deployed in hospitals under the brand names VITEK® MS (Biomerieux) and MALDI Biotyper® (Brucker Daltonics).

When applied on a blood sample, in order to limit the sources of interfering signals on the mass spectrum, blood cells need to be lysed and eliminated. The patent U.S. Pat. No. 8,569,010 discloses a protocol based on the use of sodium dodecyl detergent to support efficient blood cell lysis prior to Maldi-Tof analysis.

Compared to biochemical identification techniques that require prior isolation of the microbe, the Maldi-Tof technique allows to shorten the identification time by about 24 hours and can therefore have a direct impact on mortality statistics and average hospitalization time. In addition, the calculated cost of analysis per sample is very low and the technique leads to very little hospital waste. These advantageous medico-economic characteristics explain the rapid deployment of Maldi-Tof in hospitals.

However, the Maldi-Tof technique has limitations. For example, it is difficult to identify species that are phylogenetically close (i.e. *Escherichia coli/Shigella*, members of the *Citrobacter freundii* or *Enterobacter cloacae* group). Similarly, identification is compromised in the case of polymicrobial infections due to overlapping fingerprints or when one microbe is poorly represented compared to a second predominant species. This situation is typically encountered in situations of bacteremia in the context of poly-microbial infections of digestive origin (peritonitis, intra-abdominal abscess).

This lack of sensitivity is less prominent with the molecular biology-based techniques. Commercial solutions using molecular biology in a broad sense can be distinguished in 4 categories according to whether they employ methods based on i) fluorescence in-situ hybridization (FISH); ii) DNA microarray hybridization; iii) nucleic acid amplification (PCR); or iv) the combination of methods.

The ideal pathogen identification technique should cover the majority of species associated with sepsis, be able to be deployed directly from a positive blood culture aliquot, have the shortest possible turnaround time (ideally less than 1 hour), be economically viable, allow the identification of the different pathogens constituting a polymicrobial infection, and incidentally give an estimate of the relative or even absolute quantification of the pathogen(s). Ideally, this technique should be able to be deployed on a single analysis platform allowing to simultaneously or successively characterize in any way the possible antibiotic resistance mechanism(s) or susceptibility profile associated with the identified pathogen.

Recently, several exploratory studies have evaluated the potential interest of liquid chromatography-mass spectrometry couplings combined with a bottom-up proteomic analysis approach to identify bacteria. In this approach, the protein content of bacteria or yeast is subjected to a specific enzymatic digestion in order to generate peptides, which are then partially separated during the chromatography step before generating mass spectra and/or chromatograms reconstituted on characteristic ions, which will be compared to public or proprietary databases. The mass spectrometry analysis can be conducted in a non-targeted or a targeted manner.

In the case of a non-targeted analysis, the mass spectrometer can operate in such a way as to obtain, for example, information on the exact (monoisotopic) or chemical or molecular or average mass of each of the peptides in the mixture resulting from the enzymatic hydrolysis. In this case, a simple analysis, called MS or MS1, is performed and, as in the case of Maldi-Tof, the experimental fingerprint of all the masses of the peptides (or mass to charge ratio values; m/z) resulting from the enzymatic digestion is compared with all the theoretical fingerprints obtained by the same enzymatic digestion of all the bacterial or yeast proteomes. This is the approach named LC-MS1, as described in (Lasch et al. 2020).

In another implementation, the process comprises in addition to, or as a substitute for peptide mass information, a step wherein peptides are subjected to a fragmentation step. This step can be conditioned by a preliminary observation at a time t of the chromatogram of the n masses of the intact peptides (or values of mass to charge ratio; m/z) which will be then selected one by one to record successively n fragmentation spectra. This mode of operation is called Data Dependent Acquisition (DDA) also known as shotgun proteomics or Information Dependent Acquisition (IDA). The experimental fragmentation spectra of the peptides combined or not with information on their mass are then compared to the theoretical fragmentation spectra of all the peptides resulting from the enzymatic digestion of bacterial or yeast proteomes in order to identify the pathogen(s). This process is used for example in (Boulund et al. 2017)

Alternatively, the peptides are not selected individually from the mass spectrum but systematically fragmented in a blind manner according to the acquisition mode called Data Independent Acquisition (DIA) also known as Sequential Window Acquisition of all Theoretical Mass Spectra (SWATH) or MSE. This is the method used by (Blumenscheit et al., 2020) to detect peptides resulting from the enzymatic digestion of proteins involved in antibiotic resistance.

The targeted acquisition mode is known as Selected Reaction Monitoring (SRM), Multiple Reaction Monitoring (MRM), Parallel Reaction Monitoring (PRM), Multiple Reaction Monitoring-High Resolution (MRM-HR), Multiple Reaction Monitoring cubed (MRM3). Several studies related to the implementation of targeted mass spectrometry for the identification of bacteria or yeasts have been reported, for example to identify bacteria in urine, in tracheobronchial aspirates or from isolated colonies. This method has also been implemented to type bacteria of the genus *Acinetobacter*, to detect and quantify toxins, to detect antibiotic resistance mechanisms.

The international application WO2011/045544 describes the use of this targeted mass spectrometry method, coupled with a chromatographic separation system, to type strains of *Staphylococus aureus* from isolated colonies and concomitantly detect virulence factors and n antibiotic resistance. Similarly, the applications WO2012/143535 and WO2012/143534 describe the use of this same method to detect proteins associated with various antibiotic resistance mechanisms.

Nevertheless, it should be noted that up to this day, no diagnostic method for blood infection is based on this method using a peptide separation method combined with their detection by mass spectrometry. The reasons are twofold.

Firstly, the duration of the analysis methods is too long, most often between 30 and 120 minutes of chromatographic separation. This limits the number of samples that can be analyzed per day and increases the cost of an analysis.

Secondly, a targeted mass spectrometry method requires that when a large number of targets are to be sampled, the signals of these targets should be followed only in the chromatographic retention time window during which they are expected to be detected. This ensures that the signal intensity of the compound eluted from the chromatographic separation system will be measured at least 8 times in order to be able to define the shape of the chromatographic peak of the compound with sufficient accuracy. This approach is called "scheduled MRM, scheduled MRM HR, timed MRM, dynamic MRM" according to the mass spectrometry manufacturers. The disadvantage is that if the retention time is unexpectedly changed (e.g. due to the influence of the sample composition or concentration, or wear of the chromatography column), then target compounds may fall outside their scheduled retention window and not be detected. To take this limitation into account, the user usually takes sufficiently wide retention time windows, but this precaution in turn implies a decrease in the number of compounds that can be detected with the method.

The patent EP 3 384 517 describes a technique that overcomes these limitations. The method relies on the monitoring of "sentinel signals" belonging to compounds spread over the chromatographic separation scale. Once a sentinel signal is detected above a defined threshold, then it triggers the monitoring of a set of signals specific of target molecules of interest, until a new sentinel signal is detected. Thus, all target compounds continue to be reliably detected despite any retention time drift.

SUMMARY OF THE INVENTION

The present patent application describes a method for rapid identification of microorganisms in less than 10 minutes, preferably in 5 to 7 minutes, targeting biomarker peptides selected exclusively from those derived from enzymatic digestion of ribosomal proteins of said microorganisms.

The method is based on a list of peptides that have been thoroughly selected for the implementation of the identification method. These peptides are specific to the species to be identified, and harbor physico-chemical properties that allow them to meet the specifications set for the separation step, i.e., having an optimal peak capacity during a gradient time of about 5 minutes.

The present invention relates to a method for the identification of at least one microorganism present in a sample, based on the detection of peptides issued from the cleavage of ribosomal proteins of said microorganism, comprising the following steps:

a) lysis of microorganism(s) and cleavage of the proteins present in said sample, to obtain a mixture of peptides,
b) decomplexing said peptides mixture using a liquid separation device coupled with a mass spectrometer,
c) nebulizing the liquid eluted from the separation device using an ion source, in order to produce an ion current,
d) receiving said ion current from the ion source using said mass spectrometer and, for each cycle of a plurality of cycles, executing on the ion current a series of filtering steps for detecting a transition, said transition comprising a precursor ion and at least one fragment ion of said precursor ion, said transition being read from a predefined list of transitions using the mass spectrometer, wherein for each transition of the series, the mass spectrometer selects and fragments a precursor ion of the each transition;
e) receiving data concerning a plurality of transitions to be used to monitor the mixture of peptides using the processor,
f) assigning said plurality of transitions into two or more contiguous groups of transitions, into said predefined list of transitions, using the processor,
g) monitoring at least one sentinel transition associated with one sentinel compound in each group of the two or more contiguous groups, wherein said at least one sentinel transition is selected as having the latest expected retention time in the group, using the processor, h) when the signal of at least one sentinel transition of a group is detected with the mass spectrometer, starting the monitoring of at least one transition in a next contiguous group while stopping the monitoring of the transitions of the preceding group, using the processor, i) optionally, generating a chromatogram or an electropherogram, from the detection of transitions read from a predefined list with said mass spectrometer, using the processor, wherein each transition read from the predefined listed is associated to a peptide, and wherein the microorganism is identified according to the detection of said peptide (s).

The present invention also concerns a system for implementing the method as defined above, comprising a mass spectrometer coupled to a liquid separation device, and processing means adapted for the implementation of the steps (e) to (h), in particular adpated:

to receive data concerning a plurality of transitions to be used to monitor the mixture of peptides, to assign the plurality of transitions into two or more contiguous groups of transitions, into said predefined list of transitions, to monitor at least one sentinel transition in each group of the two or more contiguous groups, to start the monitoring of at least one sentinel transition in a next contiguous group, when the signal of at least one sentinel transition of a group is detected by the mass spectrometer, and optionally, to generate a chromatogram or an electropherogram.

The present invention also relates to a group of peptides adapted for the implementation of the method as described above, wherein said peptides are issued from ribosomal proteins, comprise between 6 and 20 amino acids, and are decomplexed with a mobile phase comprising less than 40% of acetonitrile during the decomplexing step.

Group a: *Enterobacterales* group, contains transitions associated to peptides common to 18 *Enterobacterales* and peptides specific to each *Enterobacterales* (135 transitions)

Group b: *Pseudomonas aeruginosa* group, contains 47 transitions associated to 12 peptides specific to *Pseudomonas aeruginosa* (presenting the sequence SEQ ID NO. 290 to 300)

Group c: *Staphylococcus aureus_argenteus* group, contains 35 transitions associated to 10 peptides specific to *Staphylococcus aureus* and *Staphylococcus argenteus* (presenting the sequence SEQ ID NO. 328 to 337), the selected peptides are not present in the other *Staphylococcus* species of the panel (*staphylococcus coagulase* negative) (35 transitions)

Group d: *Acinetobacter* group, contains transitions associated to 16 peptides common to 4 *Acinetobacter* (presenting the sequences SEQ ID NO. 18 to 33) and peptides specific to each *Acinetobacter* (128 transitions)

Group e: *Enterococcus* group, contains transitions associated to peptides common to 2 *Enterococcus* and peptides specific to each *Enterococcus* (53 transitions)

Group f: *Candida* group, contains transitions associated to peptides common to 7 *Candida* and peptides specific to each *Candida* (81 transitions)

Group g: Other species group, contains transitions associated to peptides specific to 31 other species (139 transitions)

Group h: "*Streptococcus* and other" group, contains transitions associated to 17 *Streptococcus* and specific peptides to certain *Streptococcus* or group of *Streptococcus*. The group also contains transitions of 7 other species. It is the only group that is not triggered by sentinel peptides (105 transitions)

Figure 2:
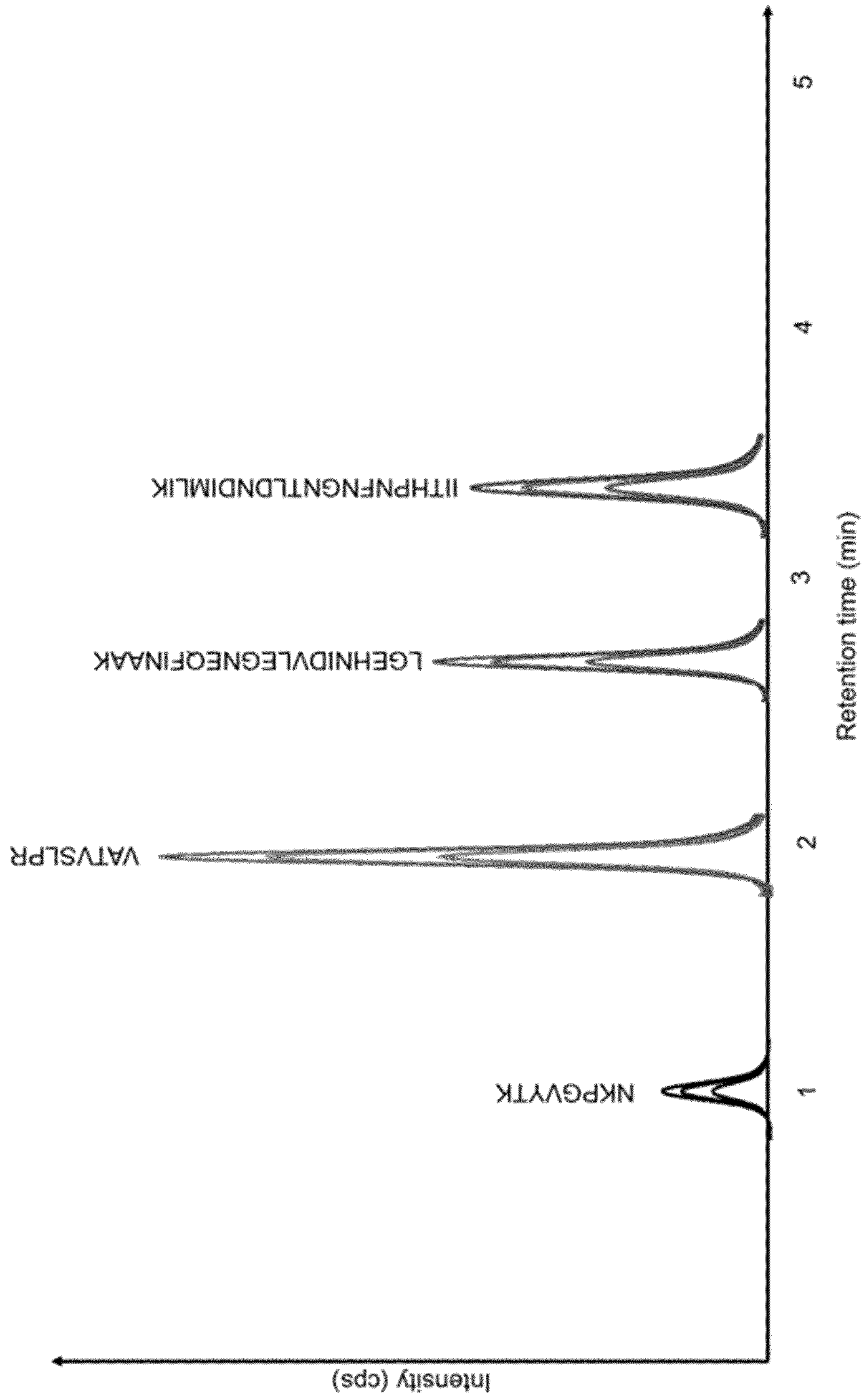

FIG. 2 shows the distribution of the following 4 sentinel peptides, issued from trypsin self-digestion, on a chromatographic gradient:

```
                                    (SEQ ID NO. 424)
NKPGVYTK

                                    (SEQ ID NO. 425)
VATVSLPR

                                    (SEQ ID NO. 426)
LGEHNIDVLEGNEQFINAAK

                                    (SEQ ID NO. 427)
IITHPNFNGNTLDNDIMLIK
```

Figure 3:
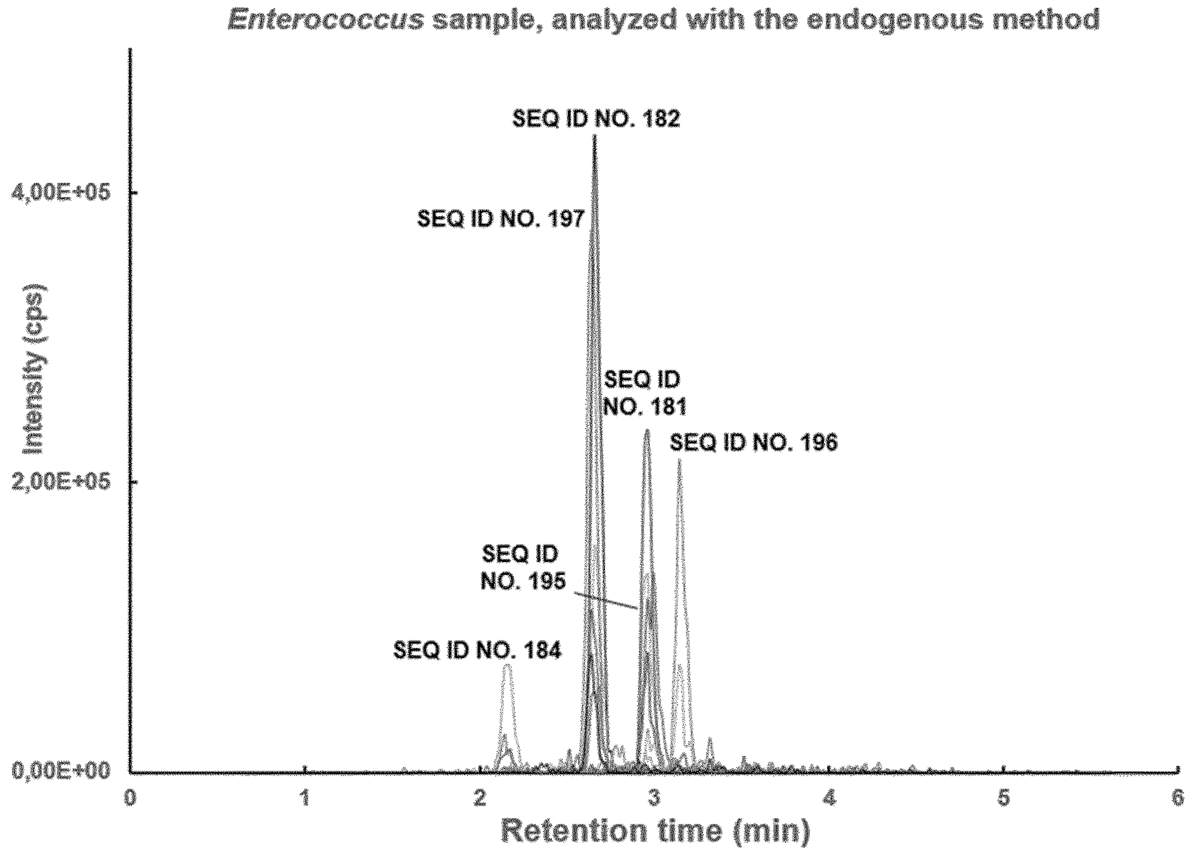

FIG. 3: Chromatogram obtained with the identification method of the invention, from a blood culture sample, analyzed with the "endogenous" sentinel peptides: the identified microorganism is *Enterococcus faecium.*

Figure 4:
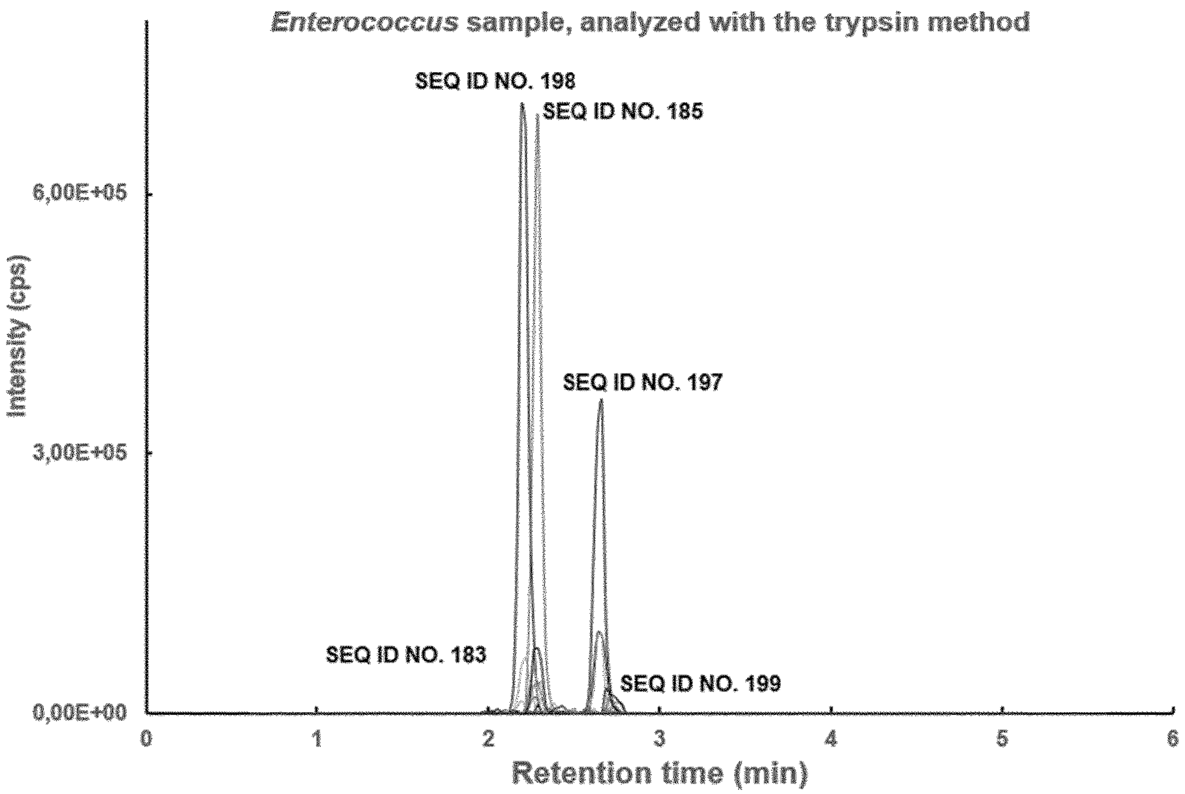

FIG. 4: Chromatogram obtained with the identification method of the invention, from a blood culture sample, analyzed with the "trypsin" sentinel peptides: the identified microorganism is *Enterococcus faecium.*

Figure 5:
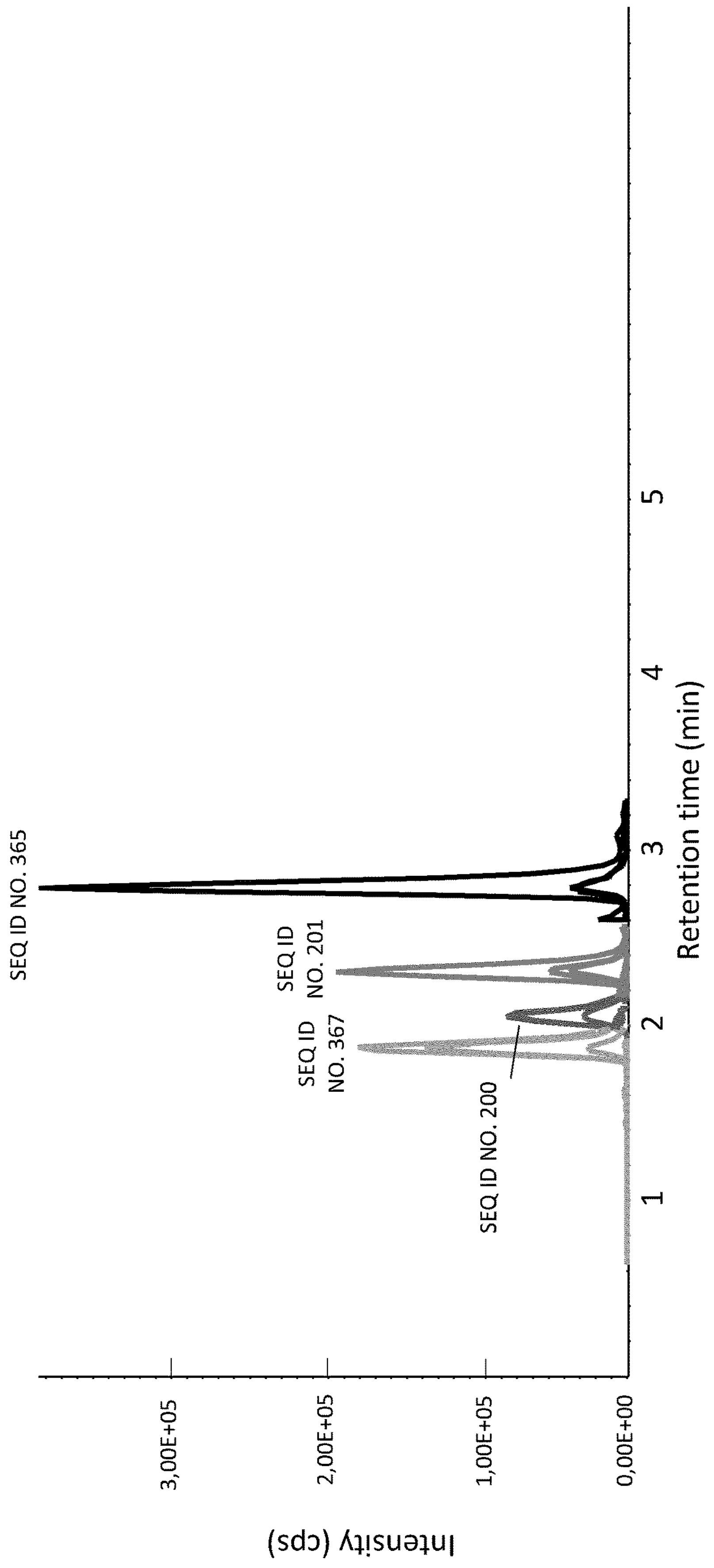

FIG. 5: Chromatogram obtained with the identification method of the invention, from a polymicrobial sample, analyzed with the "trypsin" sentinel peptides: the identified microorganisms are *Escherichia coli* (SEQ ID NO. 200 and 201) and *Streptococcus bovis* (SEQ ID NO. 365 and 367).

DETAILED DESCRIPTION OF EMBODIMENTS OF THE INVENTION

The objective of the method of the invention is to allow the identification of a microorganism in a short time, especially in a time of less than 10 minutes, with an inexpensive process, usable in routine without requiring highly qualified personnel.

In particular, the present invention concerns a method for the identification of at least one microorganism present in a sample, based on the detection of peptides issued from the cleavage of ribosomal proteins of said microorganism, comprising the following steps:

a) lysis of microorganism(s) and cleavage of the proteins present in said sample, to obtain a mixture of peptides, b) decomplexing said peptides mixture using a liquid separation device coupled with a mass spectrometer, c) nebulizing the liquid eluted from the separation device using an ion source, in order to produce an ion current, d) receiving said ion current from the ion source using said mass spectrometer and, for each cycle of a plurality of cycles, executing on the ion current a series of filtering steps for detecting a transition, said transition comprising a precursor ion and at least one fragment ion of said precursor ion, said transition being read from a predefined list of transitions using the mass spectrometer, wherein for each transition of the series, the mass spectrometer selects and fragments a precursor ion of the each transition;

e) receiving data concerning a plurality of transitions to be used to monitor the mixture of peptides using the processor, f) assigning said plurality of transitions into two or more contiguous groups of transitions, into said predefined list of transitions, using the processor, g) monitoring at least one sentinel transition associated with one sentinel compound in each group of the two or more contiguous groups, wherein said at least one sentinel transition is selected as having the latest expected retention time in the group, using the processor, h) when the signal of at least one sentinel transition of a group is detected with the mass spectrometer, starting the monitoring of at least one sentinel transition in a next contiguous group while stopping the monitoring of the transitions of the preceding group, using the processor, i) optionally, generating a chromatogram or electropherogram, from the detection of transitions read from a predefined list with said mass spectrometer, using the processor, wherein each transition read from the predefined listed is associated to a peptide, and wherein the microorganism is identified according to said peptide(s) that are detected.

Each of the steps of this identification method is presented with more details hereafter.

In the sense of the invention, the term "microorganism" designates a bacteria or a yeast.

In a specific embodiment of the invention, the microorganism is a pathogenic microorganism causing diseases to human beings. In particular, the microorganism is chosen among the most prevalent microorganisms causing bacterial infection, sepsis, or urinary tract infections.

The microorganisms that can be identified by the method of the invention can be a group of microorganisms representing a family, a genus or a species of microorganisms, pathogenic or not.

For example, the following bacteria belonging to the ESKAPE group are examples of identified microorganisms:

*Enterococcus faecium,*
*Staphylococcus aureus,*
*Klebsiella pneumoniae,*
*Acinetobacter baumannii,*
*Pseudomonas aeruginosa*, and
*Enterobacter* spp.

As other examples of microorganisms that can be identified, there may be mentioned:

Yeasts, for example *Candida krusei,*
*Streptococcus*, for example *Streptococcus pneumoniae,*
Coagulase negative *Staphylococcus.*

In the sense of the invention, the term "sample" designates:

a biological sample obtained from a mammal, chosen among the group consisting of: blood, serum, lymph, mucus, stink, saliva, tracheobronchial aspirate, cerebrospinal fluid and urine, or a sample chosen among the group consisting of: used waters, food, drink, soil sample and surface sample.

The sample may comprise one or multiple microorganisms. The method is adapted for the identification of at least one microorganism, and therefore can be implemented for identifying multiple microorganisms.

Advantageously, the method of the invention is realized in a short time, in any case in less than 10 minutes. Accordingly, this method is adapted for diagnosis and in particular for the diagnosis of sepsis in human beings.

In a preferred embodiment, the sample is a biological sample obtained from a human being, chosen among the group consisting of: blood, serum, lymph, mucus, stink, saliva, tracheobronchial aspirate, cerebrospinal fluid and urine, and is in particular a blood sample.

Step (a) of the Method

Before any step of analysis, microorganisms present in the sample are preferentially pelleted with centrifugation, filtration, acoustophoresis, levitation or spinning.

In a specific embodiment of the invention, step (a) comprises a preliminary substep of elimination of peptides that are not issued from the cleavage of ribosomal proteins. This is achieved, in particular, by addition of a surfactant into the assayed sample.

Lysis of microorganism(s) present in the sample and cleavage of the proteins are performed to obtain a mixture of peptides. In a specific embodiment, both actions are performed concomitantly.

Since the characterization of the microorganisms comes from proteins, it is necessary to process the sample before analysis by mass spectrometry. To generate peptides from the proteins present in the sample, it is possible to digest these proteins with a proteolytic enzyme (protease), for example trypsin or pepsin, or by the action of a chemical reagent, for example treatment with bromide cyanogen (CNBr) or treatment with hydroxyl radicals ($H_2O_2$).

Cleavage of proteins by enzymatic digestion is however preferable because it is easier to control and less denaturing for the structure of proteins compared to treatment with chemical reagent and particularly specific.

Enzymatic digestion is the action of one (or more) enzyme(s) which, under certain reaction conditions, will allow production of peptides from a protein. Enzymes that cut proteins in specific places, thus carrying out proteolysis are called proteases. Each protease usually has a specific cleavage site among an amino acid sequence that they are able to recognize.

The international application WO2005/098071 describes proteases that can be cited as examples:

Pepsin that hydrolyzes peptide bonds level with the amine function of aromatic amino acids (Tyr, Trp, Phe). It is used at acidic pH.

Endolysin that cuts the peptide bond of the CO group of lysines.

Trypsin that cuts the peptide bond at the level of the carboxylic group of the Lys and Arg residues.

In the method of the invention, cleavage of the proteins is preferably performed by digestion with the trypsin enzyme.

Advantageously the temperature of incubation during the step (a) of lysis and cleavage of proteins is of about 37° C.

The generation of the peptide mixture can be performed by simple dissolution. It can also be sped up using various ancillary processes such as pressurization, a microwave oven or even an ultrasound device. Lysis of the cells present in the sample may thus be more efficient with the use of one of the three methods.

Step (b)

The decomplexion of the peptides designates a partial step of separation of the peptide. This step is performed by a liquid separation technology such as liquid chromatography or capillary electrophoresis.

Liquid chromatography (LC) is a separation technique in which the mobile phase is a liquid. It can be carried out either in a column or a plane. It includes in particular high-performance liquid chromatography (HPLC), normal phase liquid chromatography (NPLC) and reversed phase liquid chromatography (RPLC).

Capillary electrophoresis (CE) is a family of separation methods performed in submillimeter diameter capillaries and in micro-and nanofluidic channels. It includes in particular capillary zone electrophoresis (CZE), capillary gel electrophoresis (CGE), capillary isoelectric focusing (CIEF), capillary isotachophoresis and micellar electrokinetic chromatography (MEKC).

In a preferred embodiment of the invention, the decomplexing step is performed by reverse phase liquid chromatography.

In an embodiment of the invention, the step of decomplexing the peptides mixture is carried out with a mobile phase comprising less than 40% of acetonitrile, on a reverse phase column. Peptides are selected as a function of their sequence length, as this feature is correlated with the retention factor k, hence the percentage of acetonitrile required for their elution out of the reverse phase column.

Acetonitrile (methyl cyanide) is a polar aprotic solvent.

Step (c)

The method is performed on a mass spectrometer that is coupled to the liquid separation device. Analysis with the mass spectrometry analysis is conducted in a targeted manner.

Typically, mass spectrometry (MS) is an analytical method where the liquid to be analyzed is ionized, using an ion source, in order to produce an ion current. The "nebulizing" of the liquid containing the mixture of peptides is well known by the person skilled in the art.

In a preferred embodiment, the mass spectrometry is of the type tandem mass spectrometry MS/MS, preferentially a parallel reaction monitoring (PRM) or a multiple reaction monitoring MRM.

In this embodiment, transitions are MRM transitions.

Step (d)

The mass spectrometer receives said ion current from the ion source and, for each cycle of a plurality of cycles, executes on the ion current a series of filtering steps for detecting a transition, said transition comprising a precursor ion and at least one fragment ion of said precursor ion, said transition being read from a predefined list of transitions using the mass spectrometer, wherein for each transition of the series, the mass spectrometer selects and fragments a precursor ion of the each transition.

In the sense of the invention, a "predefined list of transitions" designates a finite list of transitions, i.e., of specific pairs of m/z values associated to a precursor and fragment ions, wherein each transition is associated to a specific peptide. In other words, the mass spectrometer systematically monitors these transitions that are each associated to a specific peptide, and that have been defined before the analysis.

This process does not analyze in real-time the precursor ion spectrum, and does not add any information to the list. Such real-time analysis has been described, for example, in the international application WO 2014/116711.

The predefined list of transitions has been established on the basis of the table 1 regrouping 423 peptides presented below, having the sequences SEQ ID NO. 1 to SEQ ID NO. 423.

This predefined list contains transitions that are each associated to a specific peptide, possibly present in the mixture of peptides that is analyzed, and therefore that is monitored.

In a specific embodiment of the invention, the predefined list comprises at least one transition that is associated to a peptide presenting a peptide sequence selected from SEQ ID NO. 1 to SEQ ID NO. 423.

Advantageously, the predefined list comprises transitions associated to at least two, three, four, five, six, seven, eight, nine ten, twenty, thirty, forty, fifty, sixty, seventy, eighty, ninety, hundred, two hundred, three hundred or four hundred distinct peptides chosen among the group consisting of peptides having a peptide sequence selected from SEQ ID NO. 1 to SEQ ID NO. 423.

In particular, the predefined list comprises transitions associated to the 423 peptides as listed in table 1.

In another embodiment, the predefined list comprises transitions associated exclusively to at least one of the following group of peptides:

- peptides specific to *Enterobacterales*, in particular presenting a sequence chosen among SEQ ID NO. 155 to 158, SEQ ID NO. 168 to 180, SEQ ID NO. 200 to 201, SEQ ID NO. 223 to 229, SEQ ID NO. 245 to 264, SEQ ID NO. 274 to 277, SEQ ID NO. 282 to 289, SEQ ID NO. 306 to 307, SEQ ID NO. 320 to 327, SEQ ID NO. 393 to 395, SEQ ID NO. 398 to 409 and SEQ ID NO. 422 to 423;
- peptides specific to *Acinetobacter*, in particular presenting a sequence chosen among SEQ ID NO. 13 to SEQ ID NO. 42;
- peptides specific to *Enterococcus*, in particular presenting a sequence chosen among SEQ ID NO. 181 to SEQ ID NO. 199;
- peptides specific to *Candida*, in particular presenting a sequence chosen among SEQ ID NO. 81 to SEQ ID NO. 150;
- peptides specific to Staphylococcus, in particular presenting a sequence chosen among SEQ ID NO. 328 to SEQ ID NO. 345 and SEQ ID NO. 410 to SEQ ID NO. 421;
- peptides specific to *Streptococcus*, in particular presenting a sequence chosen among SEQ ID NO. 349 to SEQ ID NO. 392;
- peptides specific to *Pseudomonas aeruginosa*, in particular presenting a sequence chosen among SEQ ID NO. 290 to SEQ ID NO. 300; or
- peptides specific to other genus/species, in particular presenting a sequence chosen among SEQ ID NO. 1 to SEQ ID NO. 12, SEQ ID NO. 43 to 80, SEQ ID NO. 151 to 154, SEQ ID NO. 159 to 167, SEQ ID NO. 202 to 222, SEQ ID NO. 230 to 244, SEQ ID NO. 265 to 273, SEQ ID NO. 278 to 281, SEQ ID NO. 301 to 305, SEQ ID NO. 308 to 319, SEQ ID NO. 346 to 348, and SEQ ID NO. 396 to 397.

Step (e)

The plurality of generated transitions are data that are received by a processor and can be used to monitor the mixture of peptides, using said processor.

The term "processor" means, in the sense of the invention, any digital circuit which performs operations on some external data source. In particular, the processor is a computer. In the present case, the external data source is the mass spectrometer, and the transmitted data are the plurality of transitions.

In a classical way, the computer is adapted to execute code instructions to implement part of the data processing. It may also include a data storage module (a memory, for example flash) and advantageously a user interface (typically a screen), and biometric acquisition means.

Steps (f), (g), (h)

Said plurality of transitions is assigned into two or more contiguous groups of transitions, into said predefined list of transitions, using the processor.

According to an embodiment, the two or more contiguous groups of transitions are associated with groups of peptides, each of the peptides being specific of a microorganism genus and/or species.

Then a step of monitoring at least one sentinel transition associated with one sentinel compound in each group of the two or more contiguous groups is performed, wherein said at least one sentinel transition is selected as having the latest expected retention time in the group, using the processor.

Sentinel compounds are presented in more details in a dedicated chapter.

At the next step, when the signal of at least one sentinel transition of a group is detected with the mass spectrometer, the monitoring of at least one sentinel transition in a next contiguous group starts, while the monitoring of the transitions of the preceding group is stopped, using the processor.

Optional Step (i)

A chromatogram or electropherogram may be generated, from the detection of transitions read from a predefined list with said mass spectrometer, using the processor.

In this chromatogram or electropherogram, each peptide is represented by a peak that is "reconstituted" from the data obtained with the mass spectrometer.

While this step is not mandatory, it is useful for visual interpretation of the results.

Detected Peptides

The method for identification of microorganism(s) is based on the detection of peptides issued from the cleavage of ribosomal proteins belonging to said microorganism. Ribosomal proteins are known to be abundant, stable over time, that is to say not prone to mutations. These proteins are part of the ribosome and, among other things, translate genes encoded on messenger RNAs. There are two types of ribosomal proteins depending on the ribosome subunit to which it belongs. The letter L (for large) qualifies proteins for the large subunit and the letter S (for small) for the small subunit.

In the method of the invention, each transition read from the predefined list is associated to a peptide that is further represented by a peak on the edited chromatogram or electropherogram.

As shown in the examples section, based on the peaks present in said chromatogram or electropherogram, the microorganism can be identified.

In an embodiment of the invention, detection of one peptide specific of the genus and/or species of a microorganism is sufficient to identify such microorganism.

In another embodiment of the invention, detection of at least two peptides, specific of the genus and/or species of a microorganism, is used to identify said microorganism.

Advantageously, in the process of the invention, two or more distinct species can be identified with the detection of two or more peptides present in a same sample, each one being specific of a genus and/or a species.

Each transition is associated to a peptide issued from a ribosomal protein from a microorganism, hereafter designated as a "biomarker peptide", that has been thoroughly selected according to the features presented below.

First, these biomarker peptides need to be specific to the genus and/or species of the microorganisms to be identified.

Secondly, the biomarker peptides need to harbor physicochemical properties that allow them to meet the specifications set for the liquid separation, i.e., an optimal peak capacity during a short gradient time of few minutes.

Peak capacity is defined by the following equation:

$$P = 1 + \frac{\sqrt{N}}{4} \times \frac{B\Delta c}{B\Delta c\left(\frac{t0}{tg}\right) + 1}$$

where:

N is the column efficiency calculated in isocratic mode;

B is the slope of the linear dependency of In k versus the percentage of the organic solvent in the mobile phase ($B=2.303*0.25\sqrt{\text{Molecular}}$ weight);

Δc is the difference of the composition of the mobile phase during the gradient time (tg), with t0 corresponding to the void retention time.

For example, in an experimental set-up employing a column of 100 mm length, an internal diameter of 1 mm, a particle size of 3.5 μm, a flow of 100 μL/min and a reduced gradient time (4.12 min) to implement a rapid turnaround time, the peak capacity reaches an optimal value as soon as 30-35% of acetonitrile in the gradient solvent. Exceeding this percentage implies that more peptides will be eluted at the same peak capacity, which increases the probability of interference in the signals associated with the targets of interest.

Thirdly, the biomarker peptides are also selected as a function of their sequence length, as this feature is correlated with the retention factor k, hence the percentage of acetonitrile required for their elution out of the reverse phase column, in particular for elution out of an octadecyl reverse phase column. Among all the peptide candidates identified as specific biomarkers of the species, only those containing between 6 and 20 amino-acids were thus finally kept in the identification assay to ensure no more than 40% of acetonitrile in the gradient solvent.

In a preferred embodiment of the invention, the predefined list comprises at least one transition that is associated to a peptide comprising between 6 and 20 amino-acids, and that is decomplexed during step (b) with a mobile phase comprising less than 40% of acetonitrile.

More specifically, the predefined list comprises at least one transition that is associated to a peptide presenting a peptide sequence selected from SEQ ID NO. 1 to SEQ ID NO. 423, as presented in table 1 below.

Advantageously, each transition of the predefined list is associated to a peptide selected among the group of peptides comprising, or consisting of, peptides having the sequences as shown in SEQ ID NO. 1 to SEQ ID NO. 423.

In a specific implementation of the process, in the predefined list, at least one transition is associated with at least one peptide presenting a sequence selected from SEQ ID NO. 1 to SEQ ID NO. 423.

In another embodiment, the predefined list comprises transitions associated exclusively to at least one of the following group of peptides:

- peptides specific to *Enterobacterales*, in particular presenting a sequence chosen among SEQ ID NO. 155 to 158, SEQ ID NO. 168 to 180, SEQ ID NO. 200 to 201, SEQ ID NO. 223 to 229, SEQ ID NO. 245 to 264, SEQ ID NO. 274 to 277, SEQ ID NO. 282 to 289, SEQ ID NO. 306 to 307, SEQ ID NO. 320 to 327, SEQ ID NO. 393 to 395, SEQ ID NO. 398 to 409 and SEQ ID NO. 422 to 423;
- peptides specific to *Acinetobacter*, in particular presenting a sequence chosen among SEQ ID NO. 13 to SEQ ID NO. 42;
- peptides specific to *Enterococcus*, in particular presenting a sequence chosen among SEQ ID NO. 181 to SEQ ID NO. 199;
- peptides specific to *Candida*, in particular presenting a sequence chosen among SEQ ID NO. 81 to SEQ ID NO. 150;
- peptides specific to *Staphylococcus*, in particular presenting a sequence chosen among SEQ ID NO. 328 to SEQ ID NO. 345 and SEQ ID NO. 410 to SEQ ID NO. 421;
- peptides specific to *Streptococcus*, in particular presenting a sequence chosen among SEQ ID NO. 349 to SEQ ID NO. 392;
- peptides specific to *Pseudomonas aeruginosa*, in particular presenting a sequence chosen among SEQ ID NO. 290 to SEQ ID NO. 300; or
- peptides specific to other genus/species, in particular presenting a sequence chosen among SEQ ID NO. 1 to SEQ ID NO. 12, SEQ ID NO. 43 to 80, SEQ ID NO. 151 to 154, SEQ ID NO. 159 to 167, SEQ ID NO. 202 to 222, SEQ ID NO. 230 to 244, SEQ ID NO. 265 to 273, SEQ ID NO. 278 to 281, SEQ ID NO. 301 to 305, SEQ ID NO. 308 to 319, SEQ ID NO. 346 to 348 and SEQ ID NO. 396 to 397.

TABLE 1

Peptides specific of microorganism genus and/or species

| SEQ ID NO. | Species | Peptide sequence | Protein | Uniprot ID (Accession number) |
|---|---|---|---|---|
| 1 | *Abiotrophia defectiva* | SDEEAHALLK | 50S-L5 | A0A1F1LMP7 |
| 2 | *Abiotrophia defectiva* | GAMVLPHGTGK | 50S-L1 | A0A1F1LHQ2 |
| 3 | *Abiotrophia defectiva* | GSEAVSLTVNR | Ribosomal L25p family protein | W1Q6D2 |
| 4 | *Abiotrophia defectiva* | FVDQMITLGK | 50S-L17 | W1Q318 |
| 5 | *Abiotrophia defectiva* | AAALANLVEGSIVEGTVAR | 30S-S1 | A0A1F1LR69 |
| 6 | *Abiotrophia defectiva* | EYAVVNLEALNR | 50S-L15 | W1Q3H8 |
| 7 | *Abiotrophia defectiva* | LGFEGGQTQLFR | 50S-L15 | W1Q3H8 |
| 8 | *Abiotrophia defectiva* | ELDLIGVGYR | 50S-L6 | W1Q666 |
| 9 | *Achromobacter xylosoxidans* and *Achromobacter denitrificans* | LMQVILAPIVTEK | 50S-L23 | A0A427X0D6 |
| 10 | *Achromobacter xylosoxidans* and *Achromobacter denitrificans* | VVGALGQILGPR | 50S-L1 | A0A427X058 |
| 11 | *Achromobacter xylosoxidans* and *Achromobacter denitrificans* | VIEPLITLGK | 50S-L17 | A0A3R9MTD8 |
| 12 | *Achromobacter xylosoxidans* and *Achromobacter denitrificans* | GNTGETLIQLLESR | 30S-S4 | A0A427X0H0 |
| 13 | *Acinetobacter baumannii* | ILYEIEGVNEDLAR | 50S-L16 | V5VB35 |
| 14 | *Acinetobacter baumannii* | TDLPEFAPGDTVVVQVK | 50S-L19 | A0A5R9HP13 |
| 15 | *Acinetobacter baumannii* | ATIANVNASDEER | 30S-S14 | A0A3S8VGD7 |
| 16 | *Acinetobacter baumannii* | SGTTGNIEAATK | 50S-L18 | V5V9P3 |

TABLE 1-continued

Peptides specific of microorganism genus and/or species

| SEQ ID NO. | Species | Peptide sequence | Protein | Uniprot ID (Accession number) |
|---|---|---|---|---|
| 17 | *Acinetobacter baumannii* | STGESVAVAK | 50S-L24 | V5V9N7 |
| 18 | *Acinetobacter* common | TLEQYFGR | 30S-S9 | A0A429H485 |
| 19 | *Acinetobacter* common | QGLGIAIVSTSK | 30S-S8 | A0A3G9FV19 |
| 20 | *Acinetobacter* common | GGFTVDIGPVR | 30S-S1 | A0A4Y3J2V9 |
| 21 | *Acinetobacter* common | GIQPVSPWGQK | 50S-L2 | A0A3R9R8G4 |
| 22 | *Acinetobacter* common | VEGDIVSLETLK | 50S-L15 | A0A0B2XTW3 |
| 23 | *Acinetobacter* common | AGDAAPMAYVELVDR | 50S-L17 | A0A429H5X2 |
| 24 | *Acinetobacter* common | AALDYGLK | 30S-S11 | A0A429H627 |
| 25 | *Acinetobacter* common | EISMNIK | 30S-S13 | A0A2K8UNJ7 |
| 26 | *Acinetobacter* common | EPDLTGADLDAR | 50S-L11 | A0A0M3BX59 |
| 27 | *Acinetobacter* common | NVMEIPR | 50S-L5 | A0A0M3BYW4 |
| 28 | *Acinetobacter* common | LADEVEATLK | 30S-S1 | A0A0B2XY32 |
| 29 | *Acinetobacter* common | FNVLTSPHVNK | 30S-S10 | A0A0M3BZ77 |
| 30 | *Acinetobacter* common | VNIASIQVK | 30S-S4 | A0A2N6VEF0 |
| 31 | *Acinetobacter* common | LIDIVQPTDK | 30S-S10 | A0A2K8UNK9 |
| 32 | *Acinetobacter* common | AFTVQGVALTK | 50S-L15 | A0A0B2XTW3 |
| 33 | *Acinetobacter* common | IFEDGEIVTGVISGK | 30S-S1 | A0A4Y3J2V9 |
| 34 | *Acinetobacter lwoffii* and *Acinetobacter ursingii* | GMAMNPVDHPHGGGEGR | 50S-L2 | A0A2N6VEC5 |
| 35 | *Acinetobacter lwoffii* and *Acinetobacter ursingii* | AVEQLFGVEVVK | 50S-L23 | A0A2K8UNH0 |
| 36 | *Acinetobacter lwoffii* and *Acinetobacter ursingii* | QLGEDPWLAIMNR | 30S-S1 | A0A4Y3J2V9 |
| 37 | *Acinetobacter lwoffii* and *Acinetobacter ursingii* | SIAESIVYGALDR | 30S-S7 | A0A2K8UKR0 |
| 38 | *Acinetobacter pittii* | LQLAPVK | 50S-L6 | A0A0M3C360 |
| 39 | *Acinetobacter pittii* | ILYEIEGVNEELAR | 50S-L16 | A0A0M3BYW7 |
| 40 | *Acinetobacter pittii* | LFEDFAK | 50S-L10 | A0A429KCI7 |
| 41 | *Acinetobacter pittii* | AQVLGDTVGVQVFK | 50S-L23 | A0A3G6YJ34 |
| 42 | *Acinetobacter pittii* | QPLELLEVTEK | 30S-S9 | A0A0M3BW35 |
| 43 | *Actinomyces odontolyticus* | GTHFHPGDGVGR | 50S-L27 | A0A0V8RR43 |
| 44 | *Actinomyces odontolyticus* | IQVFQGVVIAR | 50S-L19 | A0A0V8RTA2 |
| 45 | *Actinomyces odontolyticus* | TAGLTGENLVELLEMR | 30S-S4 | A0A21112R6 |
| 46 | *Actinomyces odontolyticus* | VEDGIEGLVHISELAQR | 30S-S1 | A0A0V8RR48 |
| 47 | *Aerococcus viridans* | EATASAVSAQR | 50S-L9 | A0A2J9PM59 |
| 48 | *Aerococcus viridans* | GASSGWGK | 50S-L15 | A0A2N6UGG4 |
| 49 | *Aerococcus viridans* | MLDQAASK | 30S-S20 | A0A2N6UFJ2 |

TABLE 1-continued

Peptides specific of microorganism genus and/or species

| SEQ ID NO. | Species | Peptide sequence | Protein | Uniprot ID (Accession number) |
|---|---|---|---|---|
| 50 | *Aerococcus viridans* | IAIQEAHK | 30S-S2 | A0A2X0UMZ9 |
| 51 | *Aerococcus viridans* | VGDTLELVVIK | 30S-S1 | A0A2N6UEX7 |
| 52 | *Aerococcus viridans* | YALSEAIELLK | 50S-L1 | A0A2J9PLY4 |
| 53 | *Aerococcus viridans* | NWVVLDATDVPLGR | 50S-L13 | A0A2J9PLK4 |
| 54 | *Bacillus simplex* and *Bacillus cereus* | VATIEYDPNR | 50S-L2 | A0A2A8UL96 |
| 55 | *Bacillus simplex* and *Bacillus cereus* | MYAIIETGGK | 50S-L21 | A0A2B11YY8 |
| 56 | *Bacillus simplex* and *Bacillus cereus* | LDLPSGVDIEIK | 30S-S10 | A0A0G8F725 |
| 57 | *Bacillus simplex* and *Bacillus cereus* | WLGGTLTNFETIQK | 30S-S2 | A0A270AZC9 |
| 58 | *Bacillus simplex* and *Bacillus cereus* | EQLIFPEIDYDK | 50S-L5 | A0A2A8RT89 |
| 59 | *Bacillus simplex* and *Bacillus cereus* | MADAILEAK | 30S-S2 | A0A2B0MPM 4 |
| 60 | *Bacillus simplex* and *Bacillus cereus* | TGTVTFDVTK | 50S-L1 | A0A2B1K594 |
| 61 | *Bacteroides fragilis* | GITGEVLLQMLEGR | 30S-S4 | A0A4P8L9Z0 |
| 62 | *Bacteroides fragilis* | LLVVLPEANK | 50S-L4 | A0A4P8L976 |
| 63 | *Bacteroides fragilis* | QLTPHPWDALDPNLQVGDK | 30S-S1 | A0A081TN02 |
| 64 | *Bacteroides fragilis* and *Bacteroides thetaiotamicron* and *Bacteroides vulgatus* | AFAEQLVNLTVK | 50S-L7/ 12 | A0A081TQY3 |
| 65 | *Bacteroides fragilis* and *Bacteroides thetaiotamicron* and *Bacteroides vulgatus* | LNVVILDFDDEK | 30S-S1 | A0A3E5GBY9 |
| 66 | *Bacteroides fragilis* and *Bacteroides thetaiotamicron* and *Bacteroides vulgatus* | VINGLGIAIISTSK | 30S-S8 | A0A0P0LFV1 |
| 67 | *Bacteroides thetaiotaomicron* | VGEMIAK | 50S-L18 | A0A0P0F082 |
| 68 | *Bacteroides thetaiotaomicron* and *Bacteroides vulgatus* | FIPVYVTENMVGHK | 30S-19 | A0A0P0LM37 |
| 69 | *Bacteroides thetaiotaomicron* and *Bacteroides vulgatus* | GAPEGFVAPVTPGR | 50S-L16 | A0A0P0EVD2 |
| 70 | *Bacteroides thetaiotaomicron* and *Bacteroides vulgatus* | TSFDVVLK | 50S-L7/ L12 | A0A0P0F576 |
| 71 | *Bacteroides vulgatus* | AGDTITVAYR | 50S-L19 | A0A173YPU1 |
| 72 | *Bacteroides vulgatus* | ALYNVIPER | 50S-L25 | A0A0P0M4P9 |
| 73 | *Campylobacter coli* and *Campylobacter fetus* and *Capylobacter jejuni* | HSGYFGSVK | 50S-L13 | A0A5L4WW85 |

TABLE 1-continued

Peptides specific of microorganism genus and/or species

| SEQ ID NO. | Species | Peptide sequence | Protein | Uniprot ID (Accession number) |
|---|---|---|---|---|
| 74 | *Campylobacter coli* and *Campylobacter fetus* and *Capylobacter jejuni* | LDVGDALLVR | 50S-L25 | A0A317XDX5 |
| 75 | *Campylobacter coli* and *Campylobacter fetus* and *Capylobacter jejuni* | SLGSNNSANVVR | 30S-S5 | A0A0Q2L2L4 |
| 76 | *Campylobacter coli* and *Campylobacter fetus* and *Capylobacter jejuni* | FMYGVSEK | 30S-S4 | A0A3Z9F5H4 |
| 77 | *Campylobacter coli* and *Campylobacter fetus* and *Capylobacter jejuni* | LAAELLDAANSK | 30S-S7 | A0A1T1Z147 |
| 78 | *Campylobacter coli* and *Campylobacter fetus* and *Capylobacter jejuni* | ALMDLGSFR | 30S-S13 | A0A5L4WVV9 |
| 79 | *Campylobacter coli* and *Campylobacter fetus* and *Capylobacter jejuni* | MLDIVAATPDTVDSLTK | 30S-S10 | A0A5L4WXB7 |
| 80 | *Campylobacter coli* and *Campylobacter fetus* and *Capylobacter jejuni* | LLELIGVPFTK | 50S-L5 | A0A400M8E2 |
| 81 | *Candida albicans* (yeast) | VETGNFSWGSEGVSR | 40S-S8 | Q59T44 |
| 82 | *Candida albicans* (yeast) | IIVAPIATETAMK | 60S-L25 | C4YSV1 |
| 83 | *Candida albicans* (yeast) | YGNVNNDFVLLK | 60S-L3 | C4YKL4 |
| 84 | *Candida albicans* (yeast) | QVVFEIPGESH | 40S-S7 | Q5AJ93 |
| 85 | *Candida albicans* (yeast) | SVDAALLSEIK | 60S-S6 | Q9P834 |
| 86 | *Candida albicans* (yeast) | AVASGASVVSK | 60S-L24 | C4YGY5 |
| 87 | *Candida auris* (yeast) | APSTFER | 40S-S1 | A0A2H0ZC96 |
| 88 | *Candida auris* (yeast) | AVEVPEK | 60S-L13 | A0A2H0ZMU1 |
| 89 | *Candida auris* (yeast) | TAYETLR | 60S-L13 | A0A2H0ZMU1 |
| 90 | *Candida auris* (yeast) | LVMVTGGK | 40S-S4 | A0A2H0ZMW6 |
| 91 | *Candida auris* (yeast) | VGVLPEDK | 40S ribosomal protein S9-A | A0A2H1A2S6 |
| 92 | *Candida auris* (yeast) | AVDPFAK | 40S-S1 | A0A2H0ZC96 |
| 93 | *Candida auris* (yeast) | EVGLGFK | 40S ribosomal protein S11-A | A0A2H0ZRL1 |
| 94 | *Candida auris* (yeast) | VAPLPLAAK | 60S-L8 | A0A2H0ZJ33 |
| 95 | *Candida auris* (yeast) | LLAGLPIR | 40S-S3 | A0A2H0ZW29 |
| 96 | *Candida auris* (yeast) | SPLDVFSEEAK | 40S-S2 | A0A2H0ZCD6 |
| 97 | *Candida auris* (yeast) | SIVSEVSGLAPYER | 60S-L36 | A0A2H1A421 |
| 98 | *Candida auris* (yeast) | TINPLGGFVR | 60S-L3 | A0A2H0ZM86 |
| 99 | *Candida auris* (yeast) | VIDLQAPAQIVK | 40S-S20 | A0A2H1A705 |
| 100 | *Candida auris* (yeast) | GQLPQVPIIVK | 60S-L28 | A0A510P2R6 |

TABLE 1-continued

Peptides specific of microorganism genus and/or species

| SEQ ID NO. | Species | Peptide sequence | Protein | Uniprot ID (Accession number) |
|---|---|---|---|---|
| 101 | *Candida auris* (yeast) | ALAIFVPVPSLVGYR | 40S-S7 | A0A2H1A787 |
| 102 | *Candida* common | TSFFQALGVPTK | 60S acidic ribosomal protein P0 | C4YTG6 |
| 103 | *Candida* common | AFLIEEQK | 60S ribosomal protein L34-B | A0A0W0EQF1 |
| 104 | *Candida* common | LLGTAFK | 40S-S23 | A0A2H0ZN64 |
| 105 | *Candida* common | IGPLGLSPK | 60S-L12 | C4YPY4 |
| 106 | *Candida* common | FQTPAEK | 60S-L3 | C4YKL4 |
| 107 | *Candida* common | TFGASVR | 60S ribosomal protein L33-B | W0T8U8 |
| 108 | *Candida glabrata* (yeast) | ALSEQAEAR | 60S ribosomal protein L19-B | A0A0W0CHG0 |
| 109 | *Candida glabrata* (yeast) | TLVQAPR | 40S-S27 | A0A0W0CD45 |
| 110 | *Candida glabrata* (yeast) | TPVTLAR | 40S-S28 | A0A0W0CZC9 |
| 111 | *Candida glabrata* (yeast) | DDEVLVTR | 60S ribosomal protein L26-B | A0A0W0D7E5 |
| 112 | *Candida glabrata* (yeast) | LAASVIGAGK | 60S ribosomal protein L19-B | A0A0W0CHG0 |
| 113 | *Candida glabrata* (yeast) | VISDILTR | 40S-S1 | A0A0W0D935 |
| 114 | *Candida glabrata* (yeast) | QFLELTR | 60S-L38 | A0A0W0CD94 |
| 115 | *Candida glabrata* (yeast) | GVIGVIAGGGR | 60S-L2 | A0A0W0D2G7 |
| 116 | *Candida glabrata* (yeast) | YTLDVESFK | 60S-L27 | A0A0W0C5M3 |
| 117 | *Candida glabrata* (yeast) | LLEMSTEDFIK | 40S-S15 | A0A0W0CBJ6 |
| 118 | *Candida glabrata* (yeast) | GFSLAEIK | 60S-L13 | A0A0W0D4Y9 |
| 119 | *Candida glabrata* (yeast) | QIVFEIPETH | 40S-S7 | A0A0W0C9H1 |
| 120 | *Candida kefyr* (*Kluyveromyces marxianus*) (yeast) | QYATVSR | 60S ribosomal protein L34-B | W0TG39 |
| 121 | *Candida kefyr* (*Kluyveromyces marxianus*) (yeast) | TPGGVLR | 60S ribosomal protein L34-B | W0TG39 |
| 122 | *Candida kefyr* (*Kluyveromyces marxianus*) (yeast) | VIEQPITSETAMK | Ribosomal protein L23 | W0T9W9 |
| 123 | *Candida kefyr* (*Kluyveromyces marxianus*) (yeast) | VVYALTTIR | 40S-S18 | W0TCR0 |

TABLE 1-continued

| SEQ ID NO. | Species | Peptide sequence | Protein | Uniprot ID (Accession number) |
|---|---|---|---|---|
| Peptides specific of microorganism genus and/or species | | | | |
| 124 | *Candida kefyr* (*Kluyveromyces marxianus*) (yeast) | AVVGASLELIK | 60S-L24 | W0T4H8 |
| 125 | *Candida kefyr* (*Kluyveromyces marxianus*) (yeast) | LWTLVPEEK | Ribo-somal_L18e super family | W0T7U8 |
| 126 | *Candida kefyr* (*Kluyveromyces marxianus*) (yeast) | EGDILVLMESER | 40S-S28 | P33286 |
| 127 | *Candida krusei* (*Pichia kudriavzevii*) (yeast) | AVVVPEQTAYR | 60S-L13 | A0A099P3K9 |
| 128 | *Candida krusei* (*Pichia kudriavzevii*) (yeast) | ALEQVNLK | 60S-L3 | A0A099NWB6 |
| 129 | *Candida krusei* (*Pichia kudriavzevii*) (yeast) | VIQSPITSESATK | 60S-L25 | A0A099P8P7 |
| 130 | *Candida krusei* (*Pichia kudriavzevii*) (yeast) | VFLDVGLQR | 60S-L5 | A0A099NWE2 |
| 131 | *Candida krusei* (*Pichia kudriavzevii*) (yeast) | TITPMGGFVR | 60S-L3 | A0A099NWB6 |
| 132 | *Candida krusei* (*Pichia kudriavzevii*) (yeast) | AIVGASLDLIK | 60S-L24B | A0A099P162 |
| 133 | *Candida krusei* (*Pichia kudriavzevii*) (yeast) | ILDDLVFPTEIVGK | 40S-S7 | A0A099P5W9 |
| 134 | *Candida krusei* (*Pichia kudriavzevii*) (yeast) | FTPGSFTNYITK | 40S-S0 | A0A1Z8JQ17 |
| 135 | *Candida krusei* (*Pichia kudriavzevii*) (yeast) | SAIVQIDATPFK | 40S-S8 | A0A099P980 |
| 136 | *Candida krusei* (*Pichia kudriavzevii*) (yeast) | MIIIAANTPVLR | 60S-L30 | A0A1Z8JHE8 |
| 137 | *Candida parapsilosis (yeast)* | NSLVHDGLAR | 40S-S12 | G8BBC0 |
| 138 | *Candida parapsilosis (yeast)* | AVEVPEQSAYR | 60S-L13 | G8B7X6 |
| 139 | *Candida parapsilosis (yeast)* | LLVQQPR | 40S-S27 | G8BKA5 |
| 140 | *Candida parapsilosis (yeast)* | IAGVVYHPSNNELVR | 40S-S8 | G8BDI1 |
| 141 | *Candida parapsilosis (yeast)* | LISTIDANYLQK | 60S-L8 | G8BAV5 |
| 142 | *Candida parapsilosis (yeast)* | ILAESPSPLDLK | 40S-S7 | G8BH01 |
| 143 | *Candida parapsilosis (yeast)* | QVVFEIPGETH | 40S-S7 | G8BH01 |
| 144 | *Candida parapsilosis (yeast)* | ALAIFVPPPSVVGYR | 40S-S7 | G8BH01 |
| 145 | *Candida tropicalis* (yeast) | YASSIGR | 60S ribosomal protein L17-B | C5M6X7 |

TABLE 1-continued

Peptides specific of microorganism genus and/or species

| SEQ ID NO. | Species | Peptide sequence | Protein | Uniprot ID (Accession number) |
|---|---|---|---|---|
| 146 | *Candida tropicalis* (yeast) | LAASGASVVSK | 60S-L24 | C5MI38 |
| 147 | *Candida tropicalis* (yeast) | NFGIGQSVQPK | 60S ribosomal protein L8 | C5M7Z4 |
| 148 | *Candida tropicalis* (yeast) | QVVFEIPGENH | 40S-S7 | C5M9K3 |
| 149 | *Candida tropicalis* (yeast) | SGYTLPANIISNTDVTR | 60S-L24B | C5MC94 |
| 150 | *Candida tropicalis* (yeast) | ALAVFVPPPSLAAYR | 40S-S7 | C5M9K3 |
| 151 | *Capnocytophaga sputigena* | TAPAAVQLLEAAK | 50S-L11 | A0A2A3N613 |
| 152 | *Capnocytophaga sputigena* | NFAEQLVNLTVK | 50S-L7/L12 | A0A250FJ57 |
| 153 | *Capnocytophaga sputigena* | STLGDLEVLQELK | 30S-S1 | A0A2A3N2R7 |
| 154 | *Capnocytophaga sputigena* | IMFEVGGVPLDVAK | 50S-L16 | A0A2A3N6A5 |
| 155 | *Citrobacter freundii* and *Citrobacter braakii* | GNTGENLLGLLEGR | 30S-S4 | A0A1R0FPJ3 |
| 156 | *Citrobacter freundii* and *Citrobacter braakii* | LADVLSAAEAR | 50S-L9 | A0A1R0FR83 |
| 157 | *Citrobacter koseri* | LATELALR | 50S-L13 | A0A078LQE7 |
| 158 | *Citrobacter koseri* | VSVVNNPTGR | 30S-S22 | A0A078LDZ9 |
| 159 | *Clostridium perfringens* | NALYTPAEALELAVK | 50S-L1 | A0A133N9J9 |
| 160 | *Clostridium perfringens* | ALLNNMVVGVSQGFSK | 50S-L6 | A0A133N954 |
| 161 | *Clostridium perfringens* | VLFELSGVDEEK | 50S-L16 | A0A133N961 |
| 162 | *Clostridium perfringens* | EIETYFGLETLR | 30S-S9 | A0A133N969 |
| 163 | *Clostridium perfringens* | AIVNILLQEGYLK | 30s-s8 | A0A133N9F3 |
| 164 | *Eggerthella lenta* | EALVNYALTPFK | 30S-S9 | A0A369N4F7 |
| 165 | *Eggerthella lenta* | SLLAPLSNK | 50S-L2 | A0A369MGD7 |
| 166 | *Eggerthella lenta* | LLDAAMGDLR | 50S-L5 | A0A369MT16 |
| 167 | *Eggerthella lenta* | AADLLVIK | 30S-S4 | A0A369MX18 |
| 168 | *Enterobacter asburiae* and *Enterobacter hormachei* and *Enterobacter cloacae* | GISNVSFDR | 50S-L18 | A0A0F1R797 |
| 169 | *Enterobacterales* common | YLSLLPYTDR | 30S-S18 | A0A37617P4 |
| 170 | *Enterobacterales* common | QLGEDPWVAIAK | 30S-S1 | A0A155WS80 |
| 171 | *Enterobacterales* common | FTVLISPHVNK | 30S-S10 | A0A5B9AU26 |
| 172 | *Enterobacterales* common | VVEPLITLAK | 50S-L17 | A0A2T4HMB2 |
| 173 | *Enterobacterales* common | LVADSITSQLER | 30S-S3 | A0A4Q8WTY4 |

TABLE 1-continued

Peptides specific of microorganism genus and/or species

| SEQ ID NO. | Species | Peptide sequence | Protein | Uniprot ID (Accession number) |
|---|---|---|---|---|
| 174 | *Enterobacterales* common | FGFTSR | 50S-L15 | A0A078LPA6 |
| 175 | *Enterobacterales* common | VANLGSLGDQVNVK | 50S-L9 | A0A376V1H3 |
| 176 | *Enterobacterales* common | GGFTVELNGIR | 30S-S1 | A0A2S4QIF8 |
| 177 | *Enterobacterales* common | NYITESGK | 30S-S18 | A0A0G3SJ24 |
| 178 | *Enterobacterales* common | AVIESENSAER | 30S-S1 | A0A3R7KQS5 |
| 179 | *Enterobacterales* common | NMAGSLVR | 50S-L17 | A0A133LFI8 |
| 180 | *Enterobacterales* common | FVNILMVDGK | 30S-S7 | A0A078LHA4 |
| 181 | *Enterococcus* common | EGVVLAAFPK | 50S-L24 | A0A1B4XKV5 |
| 182 | *Enterococcus* common | TQTVLVFAK | 50S-L1 | A0A2S7S2B2 |
| 183 | *Enterococcus* common | LVDAAYDYMK | 30S-S2 | A0A1B4XQD8 |
| 184 | *Enterococcus* common | NVELGEYEVGK | 50S-L3 | A0A1B4XKR3 |
| 185 | *Enterococcus* common | SLGSNTPINVVR | 30S-S5 | A0A1B4XKW0 |
| 186 | *Enterococcus* common | FLGGIADMPR | 30S-S2 | A0A1V2U816 |
| 187 | *Enterococcus* common | SVADAISILK | 50S-L22 | A0A133N7C4 |
| 188 | *Enterococcus faecalis* | EEDESIVVESALQK | 50S-L17 | A0A1B4XKX1 |
| 189 | *Enterococcus faecalis* | QVLANLSIDTK | 50S-L4 | A0A1B4XKU7 |
| 190 | *Enterococcus faecalis* | VVVLPAGVEIK | 50S-L6 | A0A4U4BXV7 |
| 191 | *Enterococcus faecalis* | VSSVEQITALAK | 50S-L10 | A0A1B4XR41 |
| 192 | *Enterococcus faecalis* | LADAAVSTIEIER | 30S-S3 | A0A1B4XKR8 |
| 193 | *Enterococcus faecalis* | EVINQPFGVTETK | 30S-S9 | A0A4U3L7L1 |
| 194 | *Enterococcus faecalis* | FEDGTEVTPVVLK | 50S-L15 | A0A4U3MQ94 |
| 195 | *Enterococcus faecium* | VYPVAEAVALAK | 50S-L1 | A0A2S7S2B2 |
| 196 | *Enterococcus faecium* | VSSLEEITALAK | 50S-L10 | A0A3N3L9L2 |
| 197 | *Enterococcus faecium* | VTIQNLEVVR | 50S-L3 | A0A132P5N2 |
| 198 | *Enterococcus faecium* | NVQPVLEVK | 30S-S7 | A0A2A7SUB5 |
| 199 | *Enterococcus faecium* | EENEDIVIESALQK | 50S-L17 | A0A2G0EBS6 |
| 200 | *Escherichia coli* | YTAAITGAEGK | 30S-S6 | A0A376ZL25 |
| 201 | *Escherichia coli* | YTQLIER | 30S-S15 | A0A2K3TX98 |
| 202 | *Fusobacterium necrophorum* and *Fusobacterium nucleatum* | LVNDELDK | 50S-L2 | A0A4Q2L2G5 |
| 203 | *Fusobacterium necrophorum* and *Fusobacterium nucleatum* | SEWAVEGK | 30S-S3 | A0A4Q2L157 |

TABLE 1-continued

| Peptides specific of microorganism genus and/or species | | | | |
|---|---|---|---|---|
| SEQ ID NO. | Species | Peptide sequence | Protein | Uniprot ID (Accession number) |
| 204 | *Fusobacterium necrophorum* and *Fusobacterium nucleatum* | AGMYYVNSR | 30S-S2 | A0A2N6THS5 |
| 205 | *Fusobacterium necrophorum* and *Fusobacterium nucleatum* | EMTSEDLVVK | 50S-L29 | A0A4Q2KY41 |
| 206 | *Fusobacterium necrophorum* and *Fusobacterium nucleatum* | DYNLYLSAR | 50S-L4 | A0A4Q2KY35 |
| 207 | *Fusobacterium necrophorum* and *Fusobacterium nucleatum* | NAFAFLR | 50S-L17 | A0A133P930 |
| 208 | *Fusobacterium necrophorum* and *Fusobacterium nucleatum* | FQLSLGQLTNTAK | 50S-L29 | A0A4Q2KY41 |
| 209 | *Granulicatella adiacens* | ELTNDELDR | 30S-S13 | C8NH00 |
| 210 | *Granulicatella adiacens* | NVAVTTTFGPGVK | 50S-L1 | C8NHK4 |
| 211 | *Granulicatella adiacens* | AVVELAGISDVTSK | 30S-S5 | C8NH07 |
| 212 | *Granulicatella adiacens* | IGNKPVVIPAGVTVDLK | 50S-L6 | C8NH09 |
| 213 | *Granulicatella adiacens* | AYPVQEAIALAK | 50S-L1 | C8NHK4 |
| 214 | *Granulicatella adiacens* | EAGLEGMDDVFK | 50S-L10 | C8NHK3 |
| 215 | *Granulicatella adiacens* | AATILYNAFDIVK | 30S-S7 | A0A420YPY2 |
| 216 | *Granulicatella adiacens* | ELELIGVGYR | 50S-L6 | A0A420YUP9 |
| 217 | *Granulicatella adiacens* | VAIANILK | 30S-S8 | C8NH10 |
| 218 | *Haemophilus influenzae* | VNHWVAQGASLSDR | 30S-S16 | A0A0D0IKF5 |
| 219 | *Haemophilus influenzae* | DVAEAVTAAGVK | 50S-L9 | A0A0K9LCT6 |
| 220 | *Haemophilus influenzae* | SAAEAAFVEMQK | 30S-S20 | A0A3E1R4M8 |
| 221 | *Haemophilus influenzae* | ENLQALLAALNK | 50S-L1 | A0A2R3FVP7 |
| 222 | *Haemophilus influenzae* | AYEINEAIAVLK | 50S-L1 | A0A2R3GAS0 |
| 223 | *Hafnia alvei* | VSQALETLAYTNK | 50S-L22 | A0A0K0HMQ1 |
| 224 | *Hafnia alvei* | GIETVLAEIR | 50S-L28 | A0A0K0HUF1 |
| 225 | *Hafnia alvei* | DVTGIDPVSLIAFDK | 50S-L4 | A0A0K0HNJ7 |
| 226 | *Hafnia alvei* | SVEELNTELLSLLR | 50S-L29 | A0A0K0HLV5 |
| 227 | *Hafnia alvei* | ATIDGLASMK | 30S-S5 | A0A0K0HNG2 |
| 228 | *Hafnia alvei* | MFTIEATAR | 50S-L25 | A0A0M2N8U2 |
| 229 | *Hafnia alvei* | IGVPFVSGGK | 50S-L21 | A0A0K0HR96 |
| 230 | *Klebsiella aerogenes* | AQIVSEFGR | 30S-S15 | A0A094X3B8 |
| 231 | *Klebsiella aerogenes* | DIADAVSAAGVAVAK | 50S-L9 | A0A094WYW2 |
| 232 | *Klebsiella oxytoca* | AYEDAETVVGIINGK | 30S-S1 | A0A0G3SAC3 |

TABLE 1-continued

| SEQ ID NO. | Species | Peptide sequence | Protein | Uniprot ID (Accession number) |
|---|---|---|---|---|
| Peptides specific of microorganism genus and/or species | | | | |
| 233 | *Klebsiella oxytoca* | LSDLAHVEGDVIDLNTLK | 50S-L15 | A0A181WY16 |
| 234 | *Klebsiella oxytoca* | VGFFNPIASATEEGTR | 30S-S16 | A0A0G3S3W6 |
| 235 | *Klebsiella pneumoniae* | LSDLAHVEGDVVDLNALK | 50S-L15 | A0A0V9RMF1 |
| 236 | *Lactobacillus casei* | VANVDMNR | 50S-L20 | A0A510WG4 |
| 237 | *Lactobacillus casei* | AAAPVAAGAAAGGDAAATK | 50S-L7/ L12 | A0A5R8LHU0 |
| 238 | *Lactobacillus casei* | VPAGVTVTK | 50S-L6 | A0A0H0YRV1 |
| 239 | *Lactobacillus casei* | TLLVSQSHTAGR | 50S-L2 | A0A0H0YRU3 |
| 240 | *Lactobacillus casei* | HESLVVPASK | 30S-S8 | J7M404 |
| 241 | *Lactobacillus casei* | AYVNEGPTLK | 50S-L22 | J7MDP4 |
| 242 | *Lactobacillus casei* | DASILELNDLVK | 50S-L7/ L12 | A0A510WWL3 |
| 243 | *Lactobacillus casei* | LSSVVASILR | 50S-L13 | A0A510WKM4 |
| 244 | *Lactobacillus casei* | LNEEDILNWLQK | 30S-S16 | A0A0B8TJY0 |
| 245 | *Morganella morganii* | NIHNAVEVK | 50S-L6 | A0A0D8LD26 |
| 246 | *Morganella morganii* | HTGYVGGIK | 50S-L13 | A0A0A5SEE0 |
| 247 | *Morganella morganii* | VSEGQIVR | 50S-L21 | A0A0A2RI57 |
| 248 | *Morganella morganii* | ANLAAQIK | 30S-S20 | A0A0A2R704 |
| 249 | *Morganella morganii* | VGTVTPNVAEAVNNAK | 50S-L1 | A0A2X1V4V4 |
| 250 | *Morganella morganii* | AANVIGPQIEYAK | 50S-L15 | A0A0A5SG52 |
| 251 | *Morganella morganii* | SLENYFGR | 30S-S9 | A0A0A5SDF9 |
| 252 | *Morganella morganii* | VFLSGELTR | 50S-L15 | A0A0A5SG52 |
| 253 | *Morganella morganii* | VEGVNTLLVK | 50S-L23 | A0A0A2R0G5 |
| 254 | *Morganella morganii* | LYLGAVATSVR | 30S-S2 | A0A433ZRX6 |
| 255 | *Morganella morganii* | IGFFNPIAAGK | 30S-S16 | A0A433ZWE8 |
| 256 | *Morganella morganii* | TVPMFNDALAELNK | 30S-S2 | A0A433ZRX6 |
| 257 | *Morganella morganii* | ALVNAMVVGVTEGFSK | 50S-L6 | A0A0D8LD26 |
| 258 | *Morganella morganii* | LYDINEAVALLK | 50S-L1 | A0A1M7NIE9 |
| 259 | *Morganella morganii* | GNTGENLLSLLEGR | 30S-S4 | A0A0A2R0C2 |
| 260 | *Morganella morganii* | DVTAIDPVSLIAFGK | 50S-L4 | A0A0A2RFD7 |
| 261 | *Morganella morganii* | ALLSAFNFPFR | 50S-L5 | A0A433ZXX7 |
| 262 | *Morganella morganii* | GTVVAIDK | 30S-S1 | A0A0A5SJM7 |
| 263 | *Morganella morganii* | GATVLPNGTGR | 50S-L1 | A0A2X1V4V4 |
| 264 | *Morganella morganii* | AGNALPMR | 50S-L2 | A0A2T4HMC2 |
| 265 | *Neisseria meningitidis* | SGSNVEAAAIVGK | 50S-L18 | A0A0E1IDN6 |
| 266 | *Neisseria meningitidis* | MFLNTIQPAVGATHAGR | 50S-L15 | A0A1B1X0F4 |
| 267 | *Neisseria meningitidis* | GLIEFALTEEK | 50S-L3 | A0A0Y5NCX1 |
| 268 | *Neisseria meningitidis* | DLQVLMGVPVHVNIEEIR | 30S-S3 | X5END1 |

TABLE 1-continued

Peptides specific of microorganism genus and/or species

| SEQ ID NO. | Species | Peptide sequence | Protein | Uniprot ID (Accession number) |
|---|---|---|---|---|
| 269 | *Neisseria meningitidis* | AGMATILSQLTR | 50S-L4 | A0A378WCJ9 |
| 270 | *Neisseria meningitidis* | SWVVSELVEK | 30S-S17 | A0A0E1IAC4 |
| 271 | *Ochrobactrum anthropi* | TAFIALIR | 50S-L2 | A0A011T1K8 |
| 272 | *Ochrobactrum anthropi* | VLDVLQSEGYIR | 30S-S8 | A0A011VAK8 |
| 273 | *Ochrobactrum anthropi* | FITIALPR | 50S-L5 | A0A011UHY9 |
| 274 | *Pantoea agglomerans* | APVVVPAGVEVK | 50S-L6 | A0A1T4SAR2 |
| 275 | *Pantoea agglomerans* | EGSYVTLR | 50S-L2 | A0A379AA07 |
| 276 | *Pantoea agglomerans* | GLPTPVVITVYSDR | 50S-L11 | A0A1T4SCA6 |
| 277 | *Pantoea agglomerans* | QPLELLDLVGK | 30S-S9 | A0A2A7V6D3 |
| 278 | *Parvimonas micra* | ILDALTIDAFSTK | 50S-L4 | A0A0B4S0G8 |
| 279 | *Parvimonas micra* | ITGDALVMMLETR | 30S-S4 | A0A3B7DNI5 |
| 280 | *Parvimonas micra* | VLFEMSGVPVDVAR | 50S-L16 | A0A3B7DDP4 |
| 281 | *Parvimonas micra* | ALLELLGMPFK | 50S-L5 | A0A3B7DGA2 |
| 282 | *Proteus mirabilis* | QYEINEAVALLK | 50S-L1 | A0A1Z1SRZ3 |
| 283 | *Proteus mirabilis* | EAFQLAAAK | 50S-L16 | A0A2X2EDT7 |
| 284 | *Proteus mirabilis* | VDFNEAQLK | 50S-L1 | A0A1Z1SRZ3 |
| 285 | *Proteus mirabilis* | IVAEFGR | 30S-S15 | A0A5F0SX42 |
| 286 | *Proteus mirabilis* | ATMAGLGLR | 50S-L30 | A0A1Z1T0D6 |
| 287 | *Proteus vulgaris* | LATLPTYDEAIAR | 50S-L10 | A0A2J9L748-1 |
| 288 | *Proteus vulgaris* | QYEITEAVALLK | 50S-L1 | A0A379F9S2 |
| 289 | *Proteus vulgaris* | VDFNETQLK | 50S-L1 | A0A379F9S2 |
| 290 | *Pseudomonas aeruginosa* | AALSAVVADAR | 50S-L10 | A0A072ZCB6 |
| 291 | *Pseudomonas aeruginosa* | IIQQIEAEQMNK | 50S-L19 | A0A5K1SQJ0 |
| 292 | *Pseudomonas aeruginosa* | LPAGVEIK | 50S-L6 | A0A2V3F3S9 |
| 293 | *Pseudomonas aeruginosa* | VHPSVEVIQDSGELR | 50S-L6 | A0A2V3F3S9 |
| 294 | *Pseudomonas aeruginosa* | YTALIGR | 30S-S15 | A0A071L3R7 |
| 295 | *Pseudomonas aeruginosa* | STPAAVLLK | 50S-L11 | A0A1C7BKP7 |
| 296 | *Pseudomonas aeruginosa* | VEGDVVSLQTLK | 50S-L15 | A0A5E5R746 |
| 297 | *Pseudomonas aeruginosa* | IGLPVVEGAK | 50S-L21 | A0A2R3IZT6 |
| 298 | *Pseudomonas aeruginosa* | VTVQSLEIVR | 50S-L3 | A0A072ZBZ2 |
| 299 | *Pseudomonas aeruginosa* | LVVGGVNLIK | 50S-L24 | A0A1C7B7C3 |
| 300 | *Pseudomonas aeruginosa* | AGDVVAVR | 30S-S4 | A0A072ZDF7 |
| 301 | *Pseudomonas oryzihabitans* and *Pseudomonas putida* | TVLNQQAGK | 50S-L29 | A0A178LBZ8 |
| 302 | *Pseudomonas oryzihabitans* and *Pseudomonas putida* | STGEVHLR | 50S-L32 | A0A160GMP7 |

TABLE 1-continued

Peptides specific of microorganism genus and/or species

| SEQ ID NO. | Species | Peptide sequence | Protein | Uniprot ID (Accession number) |
|---|---|---|---|---|
| 303 | *Pseudomonas oryzihabitans* and *Pseudomonas putida* | SVLEAENSAER | 30S-S1 | A0A2Z5AD07 |
| 304 | *Pseudomonas oryzihabitans* and *Pseudomonas putida* | ALDAIAPLVEVK | 30S-S7 | A0A178LAS2 |
| 305 | *Pseudomonas oryzihabitans* and *Pseudomonas putida* | FGFVSLK | 50S-L15 | A0A2Z5ADV2 |
| 306 | *Raoultella ornithinolytica* | ALLNSVVIGVTEGFTK | 50S-L6 | A0A4R2XU01 |
| 307 | *Raoultella ornithinolytica* | SATGLGLK | 50S-L7/ L12 | A0A038CMN2 |
| 308 | *Rothia dentocariosa* | QAQEVIAEQATR | 30S-S2 | A0A2A8D5U0 |
| 309 | *Rothia dentocariosa* | AHETLAATGVNPDTR | 30S-S13 | A0A2A8D8A9 |
| 310 | *Rothia dentocariosa* | HIMVDGVR | 30S-S4 | A0A269YJQ1 |
| 311 | *Rothia dentocariosa* | IVYGALEGVEK | 30S-S7 | A0A2A8D8D8 |
| 312 | *Rothia dentocariosa* | AEAAEEPMAAWER | 30S-S2 | A0A2A8D5U0 |
| 313 | *Rothia dentocariosa* | LIDVVDPTPK | 30S-S10 | A0A2A8D817 |
| 314 | *Rothia dentocariosa* | IIDIDMDR | 30S-S1 | A0A269YL77 |
| 315 | *Rothia dentocariosa* | VLNLNESVMR | 30S-S6 | A0A269YH40 |
| 316 | *Rothia dentocariosa* | ELSLVEVSEFVK | 50S- L7/L12 | A0A211VKP6 |
| 317 | *Rothia dentocariosa* | TADPVTVGMVNTVAHLVK | 50S-L30 | A0A2A8D8M0 |
| 318 | *Rothia dentocariosa* | LSIEELIAAFK | 50S-L7/ L12 | A0A211VKP6 |
| 319 | *Rothia dentocariosa* | GSVILPEAITPK | 30S-S16 | A0A3S5C0X3 |
| 320 | *Salmonella enterica* | DIADAVTAAGVDVAK | 50S-L9 | A0A100PT80 |
| 321 | *Salmonella enterica* | VAVFTQGPNAEAAK | 50S-L1 | A0A447PRH1 |
| 322 | *Serratia marcescens* | SLDTDGYR | 50S-L3 | A0A1C3HK02 |
| 323 | *Serratia marcescens* | TIHDAVEVK | 50S-L6 | A0A080UYA0 |
| 324 | *Serratia marcescens* | INELGSVTIASK | 50S-L9 | A0A086FJA0 |
| 325 | *Serratia marcescens* | QEANALTFAPR | 50S-L6 | A0A080UYA0 |
| 326 | *Serratia marcescens* | DVAGIDPVSLIAFDK | 50S-L4 | A0A379YCZ8 |
| 327 | *Serratia marcescens* | DGSYVTLR | 50S-L2 | A0A0M5M078 |
| 328 | *Staphylococcus aureus* and *Staphylococcus argenteus* | SGVMEGNVITAEEVK | 50S-L10 | A0A0H2HJN6 |
| 329 | *Staphylococcus aureus* and *Staphylococcus argenteus* | IIEQIGTYNPTSANAPEIK | 30S-S16 | A0A380C4X4 |
| 330 | *Staphylococcus aureus* and *Staphylococcus argenteus* | SQSVLVFAK | 50S-L1 | A0A2X2KBV1 |

TABLE 1-continued

Peptides specific of microorganism genus and/or species

| SEQ ID NO. | Species | Peptide sequence | Protein | Uniprot ID (Accession number) |
|---|---|---|---|---|
| 331 | *Staphylococcus aureus* and *Staphylococcus argenteus* | VLELVGVGYR | 50S-L6 | A0A380ENQ7 |
| 332 | *Staphylococcus aureus* and *Staphylococcus argenteus* | MAVEEIFNVK | 50S-L23 | A0A380DT12 |
| 333 | *Staphylococcus aureus* and *Staphylococcus argenteus* | NYAVEATPGNLK | 50S-L9 | A0A5C8X5P0 |
| 334 | *Staphylococcus aureus* and *Staphylococcus argenteus* | AGIDINR | 50S-L20 | A0A077VMP6 |
| 335 | *Staphylococcus aureus* and *Staphylococcus argenteus* | VVVEGVNIMK | 50S-L24 | A0A380CL60 |
| 336 | *Staphylococcus aureus* and *Staphylococcus argenteus* | ILEEANVSADTR | 30S-S13 | W8U8U6 |
| 337 | *Staphylococcus aureus* and *Staphylococcus argenteus* | VDEALALK | 30S-S16 | A0A380C4X4 |
| 338 | *Staphylococcus coagulase* negative | AVLELAGITDILSK | 30S-S5 | A0A2T4LTV0 |
| 339 | *Staphylococcus coagulase* negative | VIFLDTTTDFK | 50S-L31 type B | A0A2T7BSB7 |
| 340 | *Staphylococcus coagulase* negative | MFAIIETGGK | 50S-L21 | A0A2T4LQZ0 |
| 341 | *Staphylococcus coagulase* negative | IDEELALK | 30S-S16 | A0A0U1EFK2 |
| 342 | *Staphylococcus coagulase* negative | SLLQPLPK | 50S-L2 | A0A2N6QET1 |
| 343 | *Staphylococcus pettenkorferi* | VIFLDTTTNYK | 50S-L31 type B | A0A2K4DRZ8 |
| 344 | *Staphylococcus saprophyticus* | ALINNMIQGVK | 50S-L6 | A0A4Y9KNP3 |
| 345 | *Staphylococcus saprophyticus* | ILYSAFDLVK | 30S-S7 | A0A4Y9KN52 |
| 346 | *Stenotrophomonas maltophilia* | AYAFEDAINILK | 50S-L1 | A0A2J0URS2 |
| 347 | *Stenotrophomonas maltophilia* | DFSEDLVHQVVVAYR | 50S-L4 | A0A4S2CXM0 |
| 348 | *Stenotrophomonas maltophilia* | DTAEVLLYALDK | 50S-L15 | A0A2W5HNQ9 |
| 349 | *Streptococcus agalactiae* | TQLESETTR | 50S-L9 | A0A380IJI9 |
| 350 | *Streptococcus agalactiae* | GQVPGVTK | 30S ribosomal protein S14 type Z | R4Z8C7 |
| 351 | *Streptococcus agalactiae* | EGASEAEANEIK | 50S-L7/L12 | A0A0H1HYJ3 |

TABLE 1-continued

Peptides specific of microorganism genus and/or species

| SEQ ID NO. | Species | Peptide sequence | Protein | Uniprot ID (Accession number) |
|---|---|---|---|---|
| 352 | *Streptococcus agalactiae* | SMVALEAGK | 50S-L23 | A0A5N0LG39 |
| 353 | *Streptococcus agalactiae* | GLTVEQDTNLR | 50S-L10 | A0A076YXU6 |
| 354 | *Streptococcus agalactiae* | FTSVEEINALAK | 50S-L10 | A0A076YXU6 |
| 355 | *Streptococcus agalactiae* | LEAAGASVTLK | 50S-L7/ L12 | A0A0H1HYJ3 |
| 356 | *Streptococcus agalactiae* | DVLSAGQEVTVK | 30S-S1 | A0A3P1APL0 |
| 357 | *Streptococcus agalactiae* | AIVDNAPSVIK | 50S-L7/ L12 | A0A0H1HYJ3 |
| 358 | *Streptococcus agalactiae* | GTHIYPGANVGR | 50S-L27 | X5K262 |
| 359 | *Streptococcus agalactiae* | SDIPEFR | 50S-L19 | R4Z9H3 |
| 360 | *Streptococcus bovis* and related | FDETTGDYSR | 50S-L32 | A0A0W7V274 |
| 361 | *Streptococcus bovis* and related | AEDVAALR | 30S-S5 | A0A060RIT2 |
| 362 | *Streptococcus bovis* and related | TAEFANVLSALNVDSK | 50S-L4 | A0A380KMA3 |
| 363 | *Streptococcus bovis* and related | GTAASIVYDAFEQIK | 30S-S7 | A0A135YPT7 |
| 364 | *Streptococcus bovis* and related | LTAPSVK | 50S-L32 | A0A0U3E3C5 |
| 365 | *Streptococcus bovis* and related | TVAALGLGK | 50S-L30 | A0A211YE03 |
| 366 | *Streptococcus bovis* and related | FIQTELADASVSR | 30S-S3 | A0A368UCF0 |
| 367 | *Streptococcus bovis* and related | EVVPAENR | 30S-S1 | A0A3E2SH26 |
| 368 | *Streptococcus bovis* and related | NEIASENFDEATEK | 50S-L17 | A0A0U3EVP9 |
| 369 | *Streptococcus bovis* and related | IAGVDIPNEK | 30S-S13 | A0A380K260 |
| 370 | *Streptocococcus* common | DFHGVPTK | 50S-L5 | A0A0C1K3D8 |
| 371 | *Streptocococcus* common | NGIHVIDLQQTVK | 30S-S2 | A0A0E1EJH5 |
| 372 | *Streptococcus* common | VLVFAR | 50S-L1 | A0A098ZG22 |
| 373 | *Streptococcus* common | SLGSNTPINIVR | 30S-S5 | A0A564S853 |
| 374 | *Streptococcus* common | MIEGTAR | 50S-L11 | A0A1L7MTN8 |
| 375 | *Streptococcus* common | INVADSR | 30S-S16 | A0A0F5MHU4 |
| 376 | *Streptococcus* common | AIITLTADSK | 50S-L23 | A0A5N0LG39 |
| 377 | *Streptococcus* common | LGLATTR | 30S-S4 | A0A4V6L8K5 |
| 378 | *Streptococcus dysgalactiae* | VEAGQVISVR | 30S-S4 | A0A2X2YUF3 |
| 379 | *Streptococcus dysgalactiae* | VINDFAK | 50S-L10 | A0A2X2UQ03 |
| 380 | *Streptococcus dysgalactiae* | VVVEGVGMIK | 50S-L24 | A0A2Z6G1V6 |

TABLE 1-continued

Peptides specific of microorganism genus and/or species

| SEQ ID NO. | Species | Peptide sequence | Protein | Uniprot ID (Accession number) |
|---|---|---|---|---|
| 381 | *Streptococcus dysgalactiae* | VLEWLAK | 30S-S16 | A0A2X2WJV0 |
| 382 | *Streptococcus* other *streptococcus* | AADGQTVTGGSILYR | 50S-L27 | A0A380JJ90 |
| 383 | *Streptococcus* other *streptococcus* | QAVEAAFEGVK | 50S-L23 | A0A081QM54 |
| 384 | *Streptococcus* other *streptococcus* | IVSGPEADIK | 50S-L2 | A0A0F2CL38 |
| 385 | *Streptococcus* other *streptococcus* | FVAVDSLSFTAPK | 50S-L4 | A0A0F2CNQ7 |
| 386 | *Streptococcus* other *streptococcus* | IQIFEGVVIAR | 50S-L19 | A0A1L7MUI0 |
| 387 | *Streptococcus pneumoniae* | AAGDYEGLSK | 30S-S14 | J1P244 |
| 388 | *Streptococcus pneumoniae* | FVGQEFDTK | 30S-S1 | A0A4M3JJF9 |
| 389 | *Streptococcus pyogenes* | SAEAAIIAK | 50S-L15 | A0A4U7HLR0 |
| 390 | *Streptococcus pyogenes* | VDPGQVISVR | 30S-S4 | A0A4Q1PT68 |
| 391 | *Streptococcus pyogenes* | VINDFTK | 50S-L10 | A0A4V6EC94 |
| 392 | *Streptococcus pyogenes* | VIVEGVGMIK | 50S-L24 | A0A4V6ELU1 |
| 393 | *Citrobacter amalonaticus* and *Citrobacter farmeri* and *Citrobacter sedlakii* and *Citrobacter koseri* | AADMTGADIEAMTR | 50S-L11 | A0A2S4RQD3 |
| 394 | *Citrobacter amalonaticus* and *Citrobacter farmeri* and *Citrobacter sedlakii* and *Citrobacter koseri* | LADVLAAANAR | 50S-L9 | A0A381GFD3 |
| 395 | *Citrobacter amalonaticus* and *Citrobacter farmeri* | INALETVTITSK | 50S-L9 | A0A381GFD3 |
| 396 | *Bacteroides fragilis* and *Bacteroides thetaiotamicron* and *Bacteroides vulgatus* | MEVVNALGR | 30S-S9 | A0A0K6BYT6 |
| 397 | *Bacteroides fragilis* and *Bacteroides thetaiotamicron* and *Bacteroides vulgatus* | YLTPPSVDVK | 30S-S18 | A0A0P0F6X2 |
| 398 | *Citrobacter braakii* and *Citrobacter freundii* and *Citrobacter youngae* and *Citrobacter werkmanii* and *Citrobacter portucalensis* and *Citrobacter cronae* | YTAAITGAEGTIHR | 30S-S6 | A0A1R0FR01 |
| 399 | *Citrobacter braakii* and *Citrobacter freundii* and *Citrobacter youngae* and *Citrobacter werkmanii* and *Citrobacter portucalensis* and *Citrobacter cronae* | TLNDAVAVNHADNALTFGPR | 50S-L6 | A0A1R0FPQ2 |
| 400 | *Citrobacter braakii* and *Citrobacter cronae* | AGDQVQSGVDAAIK | 50S-L2 | A0A1R0FPH1 |

TABLE 1-continued

Peptides specific of microorganism genus and/or species

| SEQ ID NO. | Species | Peptide sequence | Protein | Uniprot ID (Accession number) |
|---|---|---|---|---|
| 401 | *Klebsiella pneumoniae* | YTGAITAAAGTIHR | 30S-S6 | A0A377UTB6 |
| 402 | *Proteus mirabilis* | AAFAALVEK | 50S-L20 | B4ETK9 |
| 403 | *Proteus vulgaris* and *Proteus columbae* and *Proteus penneri* and *Proteus terrae* | SIVVAIDR | 30S-S17 | A0A0J1CB87 |
| 404 | *Proteus vulgaris* and *Proteus columbae* and *Proteus penneri* and *Proteus terrae* | INALGSVTISSK | 50S-L9 | A0A617CX33 |
| 405 | *Providencia rettgeri* and *Providencia stuartii* | AANVVGIQIEYAK | 50S-L15 | A0A1B8SN57 |
| 406 | *Providencia rettgeri* and *Providencia stuartii* | AGDQIQSGVDSAIK | 50S-L2 | A0A2A5PZW6 |
| 407 | *Providencia rettgeri* and *Providencia stuartii* | DMVESAPATIK | 50S-L7/L12 | A0A2A5Q0U7 |
| 408 | *Providencia rettgeri* and *Providencia stuartii* | AAAFEGELIQAK | 50S-L10 | A0A1J0E2F3 |
| 409 | *Providencia rettgeri* and *Providencia stuartii* | LSDFAAVEGDVIDLNALK | 50S-L15 | A0A1B8SN57 |
| 410 | *Staphylococcus capitis* | SLELVGVGYR | 50S-L6 | A0A4U9T7X3 |
| 411 | *Staphylococcus capitis* and *Staphylococcus caprae* | YNSEVTENLVK | 50S-L5 | A0A0U1E9T8 |
| 412 | *Staphylococcus capitis* and *Staphylococcus caprae* and *Staphylococcus haemolyticus* | TGVMEGSVISAEEVK | 50S-L10 | A0A0S4MFX3 |
| 413 | *Staphylococcus capitis* and *Staphylococcus haemolyticus* | SGAEVSGPIPLPTEK | 30S-S10 | A0A2K0A6A6 |
| 414 | *Staphylococcus caprae* and *Staphylococcus haemolyticus* and *Staphylococcus hominis* | ELVDNAPK | 50S-L7/L12 | A0A657ZQ88 |
| 415 | *Staphylococcus epidermidis* | APGSVGMASDASK | 50S-L3 | A0A0N1MT05 |
| 416 | *Staphylococcus epidermidis* | HIGSPNEVLEPGQQVNVK | 30S-S1 | A0A0N0LVM7 |
| 417 | *Staphylococcus epidermidis* | ILGIDEDNER | 30S-S1 | A0A7I0BF73 |
| 418 | *Staphylococcus hominis* | YYSVEEAIK | 50S-L1 | A0A4Q9WUN2 |
| 419 | *Staphylococcus hominis* | ILFEIAGVSEDVAR | 50S-L16 | A0A1L8Y808 |
| 420 | *Staphylococcus lugdunensis* | ILGVDEDNER | 30S-S1 | A0A4Q9WAN7 |
| 421 | *Staphylococcus lugdunensis* | VPAVVYGYSTK | 50S-L25 | A0A133PZL6 |
| 422 | *Proteus vulgaris* and *Proteus columbae* and *Proteus penneri* and *Proteus terrae* and *Proteus mirabilis* | LAETLAAAEAR | 50S-L9 | A0A1Z1SQ72 |

TABLE 1-continued

| Peptides specific of microorganism genus and/or species | | | | |
|---|---|---|---|---|
| SEQ ID NO. | Species | Peptide sequence | Protein | Uniprot ID (Accession number) |
| 423 | *Proteus vulgaris* and *Proteus columbae* and *Proteus penneri* and *Proteus terrae* and *Proteus mirabilis* | LYLTAAATAVR | 30S-S2 | A0A617D3V2 |

The method of the invention allows in particular the identification of the microorganisms belonging to the following groups:

*Enterobacterales*
*Acinetobacter*
*Enterococcus*
*Candida*
*Staphylococcus*, and
*Streptococcus.*

The group of *Enterobacterales* called *Enterobacterales*_common includes 32 species: *Citrobacter freundii, Citrobacter braakii, Citrobacter koseri, Citrobacter youngae, Citrobacter werkmanii, Citrobacter portucalensis, Citrobacter cronae, Citrobacter amalonaticus, Citrobacter farmeri, Citrobacter sedlakii, Citrobacter koseri, Enterobacter asburiae, Enterobacter cloacae, Enterobacter hormachei, Escherichia Coli, Hafnia alvei, Klebsiella aerogenes, Klebsiella oxytoca, Klebsiella pneumoniae, Morganella_morganii, Pantoea agglomerans, Proteus mirabilis, Proteus vulgaris, Proteus columbae, Proteus penneri, Proteus terrae, Raoultella ornithinolytica, Salmonella enterica, Serratia marcescens, Providencia rettgeri* and *Providencia stuartii.*

Peptides for this *Enterobacterales*_common group are common to all species in the group.

The *Acinetobacter* group called *Acinetobacter*_common includes 4 *Acinetobacter: Acinetobacter baumannii, Acinetobacter lwoffii, Acinetobacter ursingii* and *Acinetobacter pittii.*

Peptides for this *Acinetobacter*_common group are common to all species in the group.

The *Enterococcus* group called *Enterococcus*_common includes 2 *Enterococcus: Enterococcus faecium* and *Enterococcus faecalis.*

Peptides for this *Enterococcus*_common group are common to all species in the group.

The group of *Candida* called *Candida*_common includes 7 *Candida: Candida albicans, Candida auris, Candida glabrata, Candida kefyr, Candida krusei, Candida tropicalis* and *Candida parapsilosis.*

Peptides for this *Candida*_common group are common to all species in the group.

The *Staphylococcus*_coagulase_negative group comprises 10 Coagulase Negative *Staphylococcus: Staphylococcus capitis, Staphylococcus caprae, Stapylococcus cohnii, Staphylococcus epidermidis, Stahylococcus haemolyticus, Staphylococcus hominis, Staphylococcus lugdunensis, Staphylococcus pettenkorferi, Staphylococcus saprophyticus, Staphylococcus warneri.*

Peptides for this *Staphylococcus*_coagulase_negative group are common to all species in the group.

The *Streptococcus*_common group includes 17 *Streptococcus: Streptococcus agalactiae, Streptococcus dysgalactiae, Streptococcus pneunomiae, Streptococcus pyogenes, Streptococcus gallolyticus* subsp. *Gallolyticus, Streptococcus pasteurianus* (*Streptococcus gallolyticus* spp. *Pasteurianus*), *Streptococcus infantarius* spp. *Coli* (or *Streptococcus lutetiensis*), *Streptococcus infantarius* subsp. *Infantarius, Streptococcus mitis, Streptococcus oralis, Streptococcus salivarius, Streptococcus anginosus, Streptococcus parasanguinis, Streptococcus constellatus, Streptococcus sanguinis, Streptococcus gordonii, Streptococcus intermedius.*

Peptides for this *Streptococcus*_common group are common to all species in the group.

The *Streptococcus_bovis*_and_related group includes 4 *Streptococcus: Streptococcus gallolyticus* subsp. *Gallolyticus, Streptococcus pasteurianus* (*Streptococcus gallolyticus* spp. *Pasteurianus*), *Streptococcus infantarius* spp. *Coli* (or *Streptococcus lutetiensis*), *Streptococcus infantarius* subsp. *Infantarius.*

Peptides for this *Streptococcus_bovis*_and_related group are common to all species in the group.

The *Streptococcus*_other_*streptococcus* group includes 9 *Streptococcus: Streptococcus mitis, Streptococcus oralis, Streptococcus salivarius, Streptococcus anginosus, Streptococcus parasanguinis, Streptococcus constellatus, Streptococcus sanguinis, Streptococcus gordonii, Streptococcus intermedius.*

Peptides for this *Streptococcus*_other_*streptococcus* group are common to all species in the group.

Mass Spectrometer

The present method uses a mass spectrometer coupled to a liquid separation device and to processing means.

In a specific embodiment of the invention, the mass spectrometer is a tandem mass spectrometer.

A tandem mass spectrometer is capable of multiple rounds of mass spectrometry, usually separated by some form of molecule fragmentation. Tandem MS can also be done in a single mass analyzer over time, as in a quadrupole ion trap. There are various methods for fragmenting molecules for tandem MS, including collision-induced dissociation (CID), electron capture dissociation (ECD), electron transfer dissociation (ETD), infrared multiphoton dissociation (IRMPD), blackbody infrared radiative dissociation (BIRD), electron-detachment dissociation (EDD) and surface-induced dissociation (SID).

In another embodiment of the invention, the mass spectrometer uses one of the following technologies: PRM (Parallel Reaction Monitoring), MRM (Multi Reaction Monitoring), DIA (Data Independent Acquisition) or SWATH (Sequential Window Acquisition of all THeoretical fragment ion spectra mass spectrometry).

These techniques are well known by the person skilled in the art.

The present invention also concerns a system for the implementation of the method described above, comprising a mass spectrometer coupled to a liquid separation device, and comprising processing means adapted for implementing steps (e) to (h), in particular adapted:

to receive data concerning a plurality of transitions to be used to monitor the mixture of peptides, to assign the plurality of transitions into two or more contiguous groups of transitions, into said predefined list of transitions, to monitor at least one sentinel transition in each group of the two or more contiguous groups, to start the monitoring of at least one transition in a next contiguous group, when the signal of at least one sentinel transition of a group is detected by the mass spectrometer, and optionally, to generate a chromatogram or an electropherogram.

In a classical way, the system comprises a data processing module, i.e. a computer such as a processor, a microprocessor, a controller, a microcontroller, an FPGA, etc. This computer is adapted to execute code instructions to implement, if necessary, part of the data processing which is presented above. This computer is adapted to execute code instructions to implement part of the data processing that is presented above.

The system also includes a data storage module (a memory, for example flash) and advantageously a user interface (typically a screen), and biometric acquisition means.

Sentinel Compounds

The present invention uses the technology described in the patent EP 3 384 517, herein designated as the "Sentinel" acquisition mode, that allows great multiplexing capacity.

This methodology involves detection of "sentinel compounds" with a tandem mass spectrometer, which is more precisely a method for triggering a group of multiple reaction monitoring (MRM) transitions from a series of contiguous groups when at least one sentinel transition of the group is detected as part of a previous group, comprising:

separating one or more compounds from a sample using a separation device;

ionizing the separated one or more compounds received from the separation device using an ion source, producing an ion beam of one or more precursor ions;

receiving the ion beam from the ion source using a tandem mass spectrometer and, for each cycle of a plurality of cycles, executing on the ion beam a series of MRM precursor ion to product ion transitions read from a list using the tandem mass spectrometer, wherein for each transition of the series, the tandem mass spectrometer selects and fragments a precursor ion of the each transition and mass analyzes a small mass-to-charge ratio (m/z) range around the m/z of a product ion of the each transition to determine if the product ion of the each transition is detected;

receiving a plurality of MRM transitions to be used to monitor the sample using a processor;

characterized in that the method further comprises:

dividing the plurality of MRM transitions into two or more contiguous groups of MRM transitions so that different groups can be monitored separately during the plurality of cycles using the processor;

selecting at least one sentinel transition in each group of the two or more contiguous groups that identifies a next group of the two or more contiguous groups that is to be monitored using the processor;

placing a first group of the two or more contiguous groups on the list of the tandem mass spectrometer using the processor; and when at least one sentinel transition of the first group is detected by the tandem mass spectrometer, placing a next group of the two or more contiguous groups identified by the sentinel transition on the list using the processor.

Application of this method to the detection of microorganisms is described in the present specification.

The sentinel compound used in the present method may be chosen among the following compounds:

peptides issued from step (a) of cleavage of proteins of the microorganism, also designated as "endogenous peptides"; in this case, the method is hereafter designated as "Sentinel-endogenous" method;

peptides issued from autocleavage (self-digestion) of the trypsin enzyme, or peptides issued from the cleavage of proteins or peptides introduced into the sample, or exogenous introduced peptides, also designated as "exogenous peptides"; in this case, the method is hereafter designated as "Sentinel-exogenous" method;

other compounds.

Each of the implementation of the method is presented in more details in the examples section.

During the process of the invention, in steps (g) and (h), at least one sentinel transition associated with one sentinel compound is monitored, using the processor; and when the signal of at least one sentinel transition of a group is detected with the mass spectrometer, the monitoring of at least one sentinel transition in a next contiguous group starts, while the monitoring of the transitions of the preceding group is stopped, using the processor.

Sentinel compounds are selected as having the latest expected retention time in their group of transitions. In other words, they are adapted to stop the monitoring of transitions associated to a peptides group with earlier retention times than the sentinel, and thus to initiate monitoring of transitions associated to the peptides group with later retention times than the sentinel, using the processor.

Group of Peptides

In another aspect, the present invention relates to a group of peptides adapted for the implementation of the method as described above, wherein said peptides are issued from ribosomal proteins of microorganisms, comprise between 6 and 20 amino acids, and are decomplexed with a mobile phase comprising less than 40% of acetonitrile, on a reverse phase column, preferentially on an octadecyl reverse phase column.

Furthermore, these peptides are specific of a genus and/or a species of a microorganism, and therefore are useful for its identification.

This group of peptides may comprise at least two, three, four, five, six, seven, eight, nine ten, twenty, thirty, forty, fifty, sixty, seventy, eighty, ninety, hundred, two hundred, three hundred or four hundred distinct peptides.

In a specific embodiment of the invention, the group of peptides comprises at least one peptide presenting a peptide sequence selected from SEQ ID NO. 1 to SEQ ID NO. 423.

Advantageously, this group of peptides comprise at least two, three, four, five, six, seven, eight, nine ten, twenty, thirty, forty, fifty, sixty, seventy, eighty, ninety, hundred, two hundred, three hundred or four hundred distinct peptides chosen among the group of peptides having a peptide sequence selected from SEQ ID NO. 1 to SEQ ID NO. 423.

Particular groups of peptides according to the invention are the following:

- peptides specific to *Enterobacterales*, in particular presenting a sequence chosen among SEQ ID NO. 155 to 158, SEQ ID NO. 168 to 180, SEQ ID NO. 200 to 201, SEQ ID NO. 223 to 229, SEQ ID NO. 245 to 264, SEQ ID NO. 274 to 277, SEQ ID NO. 282 to 289, SEQ ID NO. 306 to 307, SEQ ID NO. 320 to 327, SEQ ID NO. 393 to 395, SEQ ID NO. 398 to 409 and SEQ ID NO. 422 to 423;
- peptides specific to *Acinetobacter*, in particular presenting a sequence chosen among SEQ ID NO. 13 to SEQ ID NO. 42;
- peptides specific to *Enterococcus*, in particular presenting a sequence chosen among SEQ ID NO. 181 to SEQ ID NO. 199;
- peptides specific to *Candida*, in particular presenting a sequence chosen among SEQ ID NO. 81 to SEQ ID NO. 150;
- peptides specific to *Staphylococcus*, in particular presenting a sequence chosen among SEQ ID NO. 328 to SEQ ID NO. 345 and SEQ ID NO. 410 to SEQ ID NO. 421;
- peptides specific to *Streptococcus*, in particular presenting a sequence chosen among SEQ ID NO. 349 to SEQ ID NO. 392;
- peptides specific to *Pseudomonas aeruginosa*, in particular presenting a sequence chosen among SEQ ID NO. 290 to SEQ ID NO. 300; or
- peptides specific to other genus/species, in particular presenting a sequence chosen among SEQ ID NO. 1 to SEQ ID NO. 12, SEQ ID NO. 43 to 80, SEQ ID NO. 151 to 154, SEQ ID NO. 159 to 167, SEQ ID NO. 202 to 222, SEQ ID NO. 230 to 244, SEQ ID NO. 265 to 273, SEQ ID NO. 278 to 281, SEQ ID NO. 301 to 305, SEQ ID NO. 308 to 319, SEQ ID NO. 346 to 348 and SEQ ID NO. 396 to 397.

In a specific embodiment, the group of peptides comprises all the peptides listed in table 1.

In another embodiment, the group of peptides consists of the 423 peptides as listed in table 1.

These groups of peptides according to the invention may be used in any method or process for the identification of at least one microorganism in a sample.

The present invention also relates to the use of one of this group of peptides as defined above, for the identification of at least one microorganism in a sample, in particular in a biological sample, more particularly in a human blood sample.

EXAMPLES

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Example 1: Construction of a Sentinel-MRM Method with Endogenous Peptides as Group Triggers To identify a microorganism, it is possible, for example, to use endogenous peptides as group triggers, i.e., as sentinel compounds.

For example, it is possible to build a Sentinel-MRM method as described below.

The specific peptides of each micro-organism are divided into the following 8 major groups:

a) An *Enterobacterales* group to identify 32 *Enterobacterales;* b) A *Pseudomonas aeruginosa* group to identify *Pseudomonas aeruginosa;* c) A *Staphylococcus aureus-argenteus* group to identify *Staphylococcus aureus* or *argenteus;* d) An *Acinetobacter* group to identify 4 *Acinetobacter;* e) An *Enterococcus* group to identify 2 *Enterococcus;* f) A *Candida* group to identify 7 *Candida;* g) A *Streptococcus* and others group to identify 17 *Streptococcus* and 4 other species;

h) A "other species" group identifying 34 species including 10 coagulase negative *Staphylococcus.*

Each group (except group h) comprises peptides specific to each species of the group and peptides common to all species of the group.

For groups a to f, two Sentinel peptides are able to trigger the group. These two Sentinel peptides are strictly specific to the desired genus and common to all the species of the group.

For example, for the group a) *Enterobacterales*, the Sentinel peptides are two peptides common to all *Enterobacterales* and present only in *Enterobacterales* species, meaning they are not found in any of the other groups.

Consider the example of a sample containing the pathogen *Acinetobacter baumannii*, during the Sentinel-MRM analysis of the sample, group d) and only group d) will be triggered and the transitions of the *Acinetobacter* peptides will be monitored. As the group also includes peptides specific to *Acinetobacter baumannii*, the identification will be successful.

Figure 1:
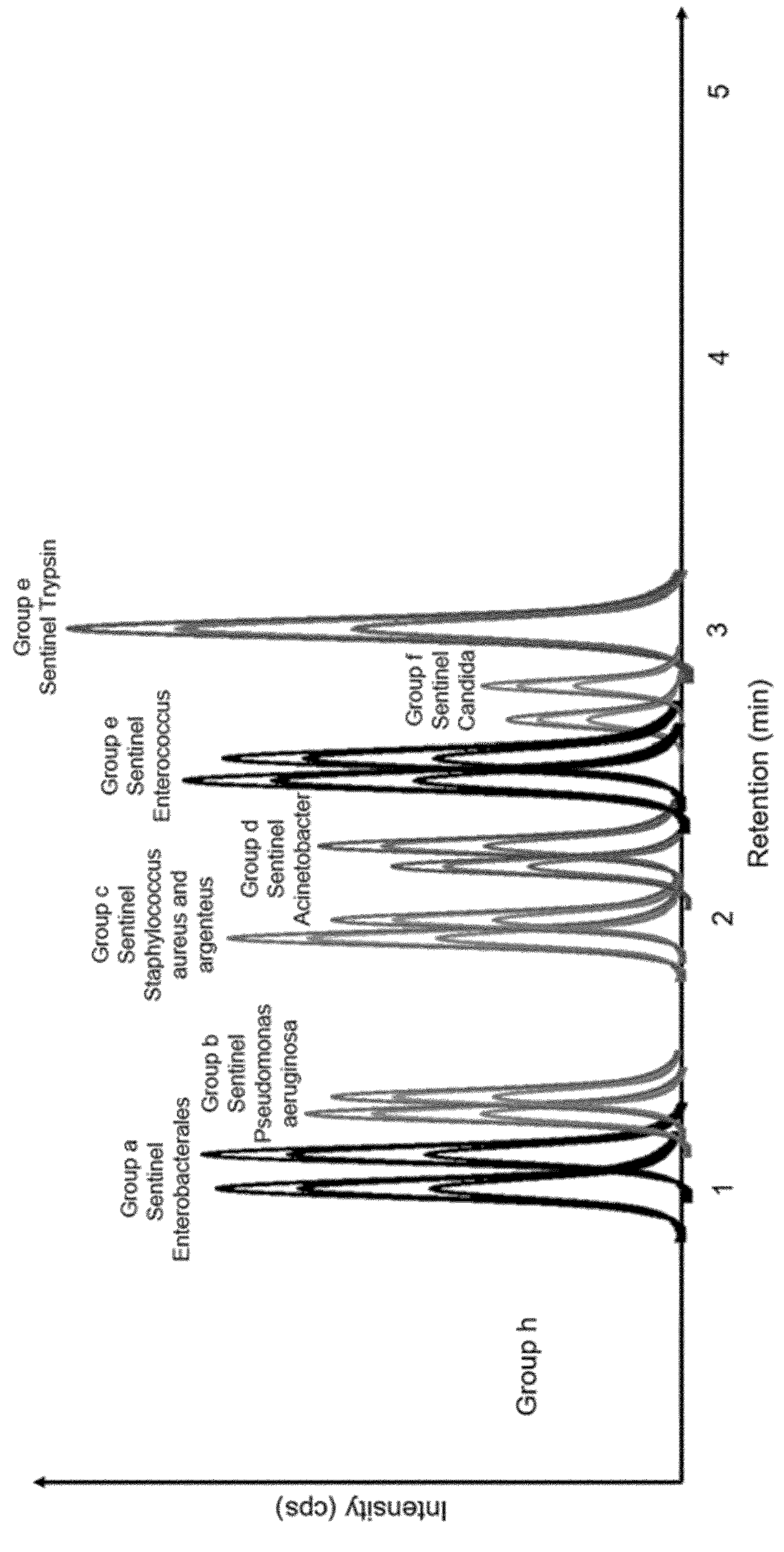
FIG. 1 illustrates a chromatogram obtained with the "sentinel-endogenous" method. The intensity of the peptides is shown in function of the retention time. Intensities are expressed in counts par seconds.

FIG. 1 shows a chromatogram obtained as an example of an endogenous Sentinel-MRM method. The intensity of the peptides are expressed in arbitrary units.

The interest of using two peptides as sentinel compounds, instead of only one, is to secure the trigger of a transition group. For example, if a peptide is mutated, or non-present in the analyzed sample, the second peptide will be able to trigger the transition group.

Example 2: Construction of an Exogenous Sentinel-MRM Method with Exogenous Peptides (Trypsin) as Group Triggers Trypsin is used as a digesting enzyme in the preparation of the samples. It is therefore present in excess in all samples; the peptides resulting from the self-digestion of trypsin itself can be used as sentinel compounds of groups of transitions. The principle is to distribute the specific peptides of each bacterial species (see table 1) into 4 groups triggered by 4 peptides resulting from the self-digestion of trypsin.

The FASTA sequence of trypsin (accession number P00761), hereafter referenced as SEQ ID NO. 428, is as follows:

FPTDDDDKIVGGYTCAANSIPYQVSLNSGSHFCGGSLINSQWVVSAAHCY KSRIQVRLGEHNIDVLEGNEQFINAAKIITHPNFNGNTLDNDIMLIKLSS PATLNSRVATVSLPRSCAAAGTECLISGWGNTKSSGSSYPSLLQCLKAPV LSDSSCKSSYPGQITGNMICVGFLEGGKDSCQGDSGGPVVCNGQLQGIVS WGYGCAQKNKPGVYTKVCNYVNWIQQTIAAN

The 4 peptides selected as Sentinel triggers (sentinel compounds) are as follows:

(SEQ ID NO. 424)
NKPGVYTK (SEQ ID NO. 425)
VATVSLPR (SEQ ID NO. 426)
LGEHNIDVLEGNEQFINAAK (SEQ ID NO. 427)
IITHPNFNGNTLDNDIMLIK

FIG. 2 shows the distribution of these 4 peptides on a chromatogram.

One of the advantages of using peptides derived from trypsin is the possibility of following all the transitions of the selected peptides, without the risk of not triggering a group due to a low intensity (few quantity of bacteria present in the sample for example) or the triggering of a group by an interference in the sample.

Another advantage of this implementation is to be able to identify several bacteria in the context of a poly-infection, for example.

This implementation of the method could also be more easily incremented than the "endogenous" method with peptides from new or different species from the panel chosen in the context of this invention. For example, it will suffice to create an MRM method with the "new" peptides to know their retention time and to place them in the group of transitions corresponding to the order of elution of the tryptic peptides.

Example 3: Identification of a Microorganism from a Positive Blood Culture by Sentinel-MRM Mode of Acquisition 1. Isolation of Microorganisms from a Positive Blood Culture To isolate the bacteria/yeast present in a blood culture flask that has been detected as being positive, i.e., as comprising at least one microorganism, the procedure consists of lysing the blood cells using a lysis buffer (here, 12% SDS) and then recovering the bacteria by centrifugation.

- Using a syringe and a 21G needle, take 1 mL of blood culture medium and transfer it to a 1.5 mL Eppendorf tube
- Add 200 µL of 12% sodium dodecyl sulfate (SDS) then vortex for 10 seconds
- Centrifuge for 2 minutes at 16100 g and remove the supernatant
- Resuspend the pellet in 1 mL of physiological serum
- Centrifuge for 1 minute at 16100 g and discard the supernatant
- Resuspend the pellet in 1 mL of physiological serum 2. Generation of Peptides by Enzymatic Digestion and Cell Lysis

- In a 1.5 mL Eppendorf LowBind tube add a spoon of glass beads (Glass beads, acid-washed, 150-212 µm, Sigma-Aldrich, ref G1145) for a height of about 3-4 mm (one third of the final volume)
- Vortex the sample prepared according to paragraph 1 for 10 seconds then take 200 µl and dispense it in the tube containing the glass beads
- Prepare a 1 mg/mL solution of trypsin in 150 mM Ammonium Bicarbonate buffer from lyophilized trypsin.
- Add 50 µL of freshly prepared trypsin solution (1 mg/mL) to the tube containing the beads and bacteria/yeasts and vortex for 3 seconds
- Place the sample in the water bath of the sonicator, for example a Diagenode, set at 50° C.
- Immediately start the ultrasound 10 cycles of 1 minute
  - 30 seconds ultrasound ON
  - 30 seconds ultrasound OFF Ultrasonic power: Low
- After digestion add 5 µL of formic acid and vortex for 3 seconds to stop the reaction
- Centrifuge the tube at 9600 g (10,000 rpm on an Accuspin Micro 17 benchtop centrifuge) for 5 minutes
- Transfer 150 µL of the supernatant into an amber vial fitted with an insert 3. Analytical Conditions: Chromatographic and Mass Spectrometric Conditions Each sample is treated according to the protocols of paragraphs 1 and 2, then a volume of 5 µL of digested proteins is injected and analyzed under the following conditions:

- HPLC device Agilent Pump 1290 of the company AGILENT (AGILENT, Santa Clara, United States of America)
- WATERS chromatographic column (WATERS, Saint-Quentin en Yvelines, France) XBridge Peptide BEH C18, 1 mm internal diameter, 100 mm long, particle size 3.5 µm, pore size 130 Å)
- Solvent A: $H_2O$ 99.9%+0.1% formic acid
- Solvent B: Acetonitrile 99.9%+0.1% formic acid
- Column oven temperature: 60° C.
- HPLC gradient defined according to table 2 defined below:

TABLE 2 chromatographic gradient

| Step | Time (min) | Flow (µL/min) | Solvent A (%) | Solvent B (%) |
|---|---|---|---|---|
| Decomplexing | 0 | 100 | 98 | 2 |
| Decomplexing | 0.1 | 100 | 90 | 10 |
| Decomplexing | 4.22 | 100 | 65 | 35 |
| Washing | 4.25 | 100 | 25 | 75 |
| Washing | 4.28 | 200 | 25 | 75 |
| Washing | 4.30 | 300 | 25 | 75 |
| Washing | 5.22 | 300 | 25 | 75 |
| Equilibrating | 5.77 | 300 | 98 | 2 |
| Equilibrating | 5.78 | 200 | 98 | 2 |
| Equilibrating | 5.79 | 100 | 98 | 2 |
| Equilibrating | 7.00 | 100 | 98 | 2 |

The decomplexing step (i.e. partial separation) of the peptides is performed under conditions with less than 40% of solvent B, mainly composed of the polar solvent acetonitrile.

The eluate coming from the chromatographic column is injected directly into the ionization source of the QTRAP®6500+mass spectrometer from AB SCIEX (Framingham, Massachussetts, United States of America).

The other settings of the instrument are gathered in table 3 below.

TABLE 3

| Settings of the mass spectrometer | |
|---|---|
| Scan type | Sentinel-MRM |
| Polarity | Positive |
| Ionisation source | Turbo Spray IonDrive (AB SCIEX) |
| Resolution Q1 | unit |
| Resolution Q3 | unit |
| Dwell time | 5 ms |
| Pause between mass ranges | 5 ms |
| Scan rate | 10 Da/sec |
| Curtain gas | 50.00 psi |
| Ion spray voltage | 5500.00 V |
| Source Temperature | 550.00° C. |
| Gas source 1 (nebulising) | 70.00 psi |
| Gas source 2 (drying) | 60.00 psi |
| Collision Gas | high |
| Entrance Potential (EP) | 10.00 V |
| Collision Cell Exit Potential (CXP) | 12.00 V |
| Software version | Analyst 1.7.2 |

The peptides resulting from the digestion of the proteins of the bacteria with trypsin are analyzed by the mass spectrometer in the Sentinel-MRM mode. The peptides tracked and detected allow the identification of the microorganism because they are specific to it.

4. Identification of a Microorganism by Sentinel-MRM Mode of Acquisition, Use of Endogenous Peptides such as Sentinel, Application to a Blood Culture Sample (Blind Identification)

The Sentinel-MRM method shown in Example 1 is applied to a blood culture sample.

The Sentinel-MRM acquisition method uses 3 or more transitions of each peptide (see the acquisition method in table 4), which constitutes a method containing more than 1500 transitions. To increase the specificity of the trigger Sentinel and thus avoid triggering a group by an interference present in the sample, it was decided that the alignment of three transitions was necessary to trigger a group.

The chromatogram obtained is shown in FIG. 3. The *Enterococcus* group was successfully triggered and only peptides specific to the genus *Enterococcus* and the species *Enterococcus faecium* were detected. This result was confirmed by MALDI-TOF.

5. Identification of the Microorganism by Sentinel-MRM Mode of Acquisition, Use of Trypsine-Issued Peptides as Sentinel Compounds The same sample as the example above is analyzed by applying the Sentinel-MRM acquisition method with trypsin peptides as Sentinel triggering groups of transitions.

Results are presented in FIG. 4. Only peptides specific to the genus *Enterococcus* and the species *Enterococcus faecium* were detected. This result was confirmed by MALDI-TOF.

Example 4: Analysis Validation of the Two Acquisition Method in Comparison with the Analysis with a MALDI-TOF To validate the two acquisition methods, 42 samples have been analyzed. The results are shown in table 4.

TABLE 4

Implementation of the method of the invention on 42 blood samples

| Blood sample | Flask AEROBIC/ ANAEROBIC | Identification with MALDI-TOF | Identification with the « endogenous » method of the invention | Identification with the « exogenous » method of the invention |
|---|---|---|---|---|
| Sample1 | AER | *Staphylococcus epidermidis* | *Staphylococcus coagulase* negative | *Staphylococcus coagulase* negative |
| Sample2 | AER | *Escherichia coli* | *Escherichia coli* | *Escherichia coli* |
| Sample3 | AER | *Escherichia coli* | *Escherichia coli* | *Escherichia coli* |
| Sample4 | ANA | *Klebsiella pneumoniae* | *Klebsiella pneumoniae* | *Klebsiella pneumoniae* |
| Sample5 | AER | *Morganella morganii* | *Morganella morganii* | *Morganella morganii* |
| Sample6 | AER | *Klebsiella pneumoniae* | *Klebsiella pneumoniae* | *Klebsiella pneumoniae* |
| Sample7 | ANA | *Klebsiella aerogenes* | *Klebsiella aerogenes* | *Klebsiella aerogenes* |
| Sample8 | AER | *Klebsiella pneumoniae* | *Klebsiella pneumoniae* | *Klebsiella pneumoniae* |
| Sample9 | AER | *Escherichia coli* | *Escherichia coli* | *Escherichia coli* |
| Sample10 | AER | *Enterrococcus faecium* | *Enterrococcus faecium* | *Enterrococcus faecium* |
| Sample11 | AER | *Streptococcus gallolyticus* | *Streptococcus bovis* and related | *Streptococcus bovis* and related |
| Sample12 | AER | *Klebsiella oxytoca* | *Klebsiella oxytoca* | *Klebsiella oxytoca* |
| Sample13 | AER | *Escherichia coli* | *Escherichia coli* | *Escherichia coli* |
| Sample14 | AER | *Staphylococcus aureus* | *Staphylococcus aureus* or *argenteus* | *Staphylococcus aureus* or *argenteus* |
| Sample15 | AER | *Escherichia coli* | *Escherichia coli* | *Escherichia coli* |
| Sample16 | AER | *Staphylococcus aureus* and *Bacillus cereus* | *Staphylococcus aureus* or *argenteus* | *Staphylococcus aureus* or *argenteus* and *Bacillus* |
| Sample17 | AER | *Enterrococcus faecalis* | *Enterrococcus faecalis* | *Enterrococcus faecalis* |
| Sample18 | AER | *Enterobacter cloacae* complex | *Enterobacter asburiae hormachei cloacae* | *Enterobacter asburiae hormachei cloacae* |
| Sample19 | ANA | *Proteus mirabilis* | *Proteus mirabilis* | *Proteus mirabilis* |
| Sample20 | AER | *Enterobacter cloacae* | *Enterobacter asburiae hormachei cloacae* | *Enterobacter asburiae hormachei cloacae* |
| Sample21 | AER | *Escherichia coli* | *Escherichia coli* | *Escherichia coli* |
| Sample22 | AER | *Klebsiella pneumoniae* | *Klebsiella pneumoniae* | *Klebsiella pneumoniae* |
| Sample23 | AER | *Escherichia coli* | *Escherichia coli* | *Escherichia coli* |
| Sample24 | AER | *Escherichia coli* | *Escherichia coli* | *Escherichia coli* |
| Sample25 | AER | *Escherichia coli* and *Klebsiella pneumoniae* | *Escherichia coli* and *Klebsiella pneumoniae* | *Escherichia coli* and *Klebsiella pneumoniae* |

TABLE 4-continued

Implementation of the method of the invention on 42 blood samples

| Blood sample | Flask AEROBIC/ ANAEROBIC | Identification with MALDI-TOF | Identification with the « endogenous » method of the invention | Identification with the « exogenous » method of the invention |
|---|---|---|---|---|
| Sample26 | AER | *Pseudomonas aeruginosa* | *Pseudomonas aeruginosa* | *Pseudomonas aeruginosa* |
| Sample27 | AER | *Escherichia coli* | *Escherichia coli* | *Escherichia coli* |
| Sample28 | AER | *Klebsiella pneumoniae* | *Klebsiella pneumoniae* | *Klebsiella pneumoniae* |
| Sample29 | ANA | *Escherichia coli* | *Escherichia coli* | *Escherichia coli* |
| Sample30 | AER | *Pseudomonas aeruginosa* | *Pseudomonas aeruginosa* | *Pseudomonas aeruginosa* |
| Sample31 | AER | *Enterococcus faecalis* | *Enterococcus faecalis* | *Enterococcus faecalis* |
| Sample32 | ANA | *Bacillus* spp | *Bacillus cereus* or *Bacillus simplex* | *Bacillus cereus* or *Bacillus simplex* |
| Sample33 | AER | *Staphylococcus epidermidis* | *Staphylococcus coagulase* negative | *Staphylococcus coagulase* negative |
| Sample34 | AER | *Escherichia coli* | *Escherichia coli* | *Escherichia coli* |
| Sample35 | AER | *Staphylococcus epidermidis* | *Staphylococcus coagulase* negative | *Staphylococcus coagulase* negative |
| Sample36 | AER | *Klebsiella pneumoniae* | *Klebsiella pneumoniae* | *Klebsiella pneumoniae* |
| Sample37 | AER | *Klebsiella aerogenes* | *Klebsiella aerogenes* | *Klebsiella aerogenes* |
| Sample38 | AER | *Pseudomonas aeruginosa* | *Pseudomonas aeruginosa* | *Pseudomonas aeruginosa* |
| Sample39 | ANA | *Escherichia coli* | *Escherichia coli* | *Escherichia coli* |
| Sample40 | AER | *Proteus mirabilis* | *Proteus mirabilis* | *Proteus mirabilis* |
| Sample41 | AER | *Staphylococcus haemolyticus* | *Staphylococcus coagulase* negative | *Staphylococcus coagulase* negative |
| Sample42 | AER | *Staphylococcus epidermidis* | *Staphylococcus coagulase* negative | *Staphylococcus coagulase* negative |

Other tests on 264 positive blood culture (bacteria or yeast) samples obtained from patients have been conducted.

Results obtained with the process of the invention have been compared with those obtained with MALDI-TOF MS identification technique: a correlation of 100% of the results have been observed.

Regarding the percentage of identification, the process of the invention allowed the identification of at least one bacterial or yeast species in 93% of the assayed samples. In 7% of the samples, no identification could be obtained, probably due to an insufficient amount of microorganisms in the sample, or because the sample was actually microorganism-free.

Example 5. Identification of Two Different Bacterial Species Present in a Sample, Via the Trypsin-Method A positive blood sample has been analyzed by applying the Sentinel-MRM acquisition method with trypsin peptides as Sentinel triggering groups of transitions.

Results are presented in FIG. 5. Peptides specific to the group *Streptococcus bovis* (SEQ ID NO: 365, 367) and the species *Escherichia coli* (SEQ ID NO. 200, 201) were detected.

This result was confirmed by MALDI-TOF the day after, after an over-night sub-culturing step of the blood sample.

Advantageously, the process of the invention allows the identification of at least two different species in a same sample.

REFERENCES CITED IN ORDER OF CITATION IN THE TEXT

Patents

WO 2011/045544
WO 2012/143535
WO 2012/143534
EP 3384517
WO 2005/098071
WO 2014/116711

BIBLIOGRAPHIC REFERENCES

Holland, R. D., Duffy, C. R., Rafii, F., Sutherland, J. B., Heinze, T. M., Holder, C. L., Voorhees, K. J., Lay, J. O., Jr., 1999. *Identification of bacterial proteins observed in MALDI TOF mass spectra from whole cells*. Analytical chemistry. 71, 3226-3230

Lasch P, Schneider A, Blumenscheit C, Doellinger J. Identification of Microorganisms by Liquid Chromatography-Mass Spectrometry (LC-MS1) and in Silico Peptide Mass Libraries. Mol Cell Proteomics. 2020 December; 19(12):2125-2139. doi: 10.1074/mcp-.TIR120.002061. Epub 2020 Sep. 30. PMID: 32998977; PMCID: PMC7710138.

Boulund F, Karlsson R, Gonzales-Siles L, Johnning A, Karami N, Al-Bayati O, Åhrén C, Moore ERB, Kristiansson E. Typing and Characterization of Bacteria Using Bottom-up Tandem Mass Spectrometry Proteomics. Mol Cell Proteomics. 2017 June; 16(6):1052-1063.

Christian Blumenscheit, Yvonne Pfeifer, Guido Werner, Charlyn John, Andy Schneider, Peter Lasch, Joerg Doellinger. Unbiased antimicrobial resistance detection from clinical bacterial isolates using proteomics. bioRxiv 2020.11.17.386540; doi:

The invention claimed is:

1. A method for the identification of at least one microorganism present in a sample based on the detection of peptides issued from the cleavage of ribosomal proteins of said microorganism, comprising the following steps:

a) lysis of microorganism(s) and cleavage of the proteins present in said sample to obtain a mixture of peptides, b) decomplexing said peptides mixture using a liquid separation device coupled with a mass spectrometer, c) nebulizing a liquid eluted from the separation device using an ion source in order to produce an ion current, d) receiving said ion current from the ion source using said mass spectrometer and, for each cycle of a plurality of cycles, executing on the ion current a series of filtering steps for detecting a transition, said transition comprising a precursor ion and at least one fragment ion of said precursor ion, said transition being read from a predefined list of transitions using the mass spectrometer, wherein for each transition of the series, the mass spectrometer selects and fragments a precursor ion of the each transition, e) receiving data concerning a plurality of transitions to be used to monitor the mixture of peptides using the processor, f) assigning said plurality of transitions into two or more contiguous groups of transitions, into said predefined list of transitions using the processor, g) monitoring at least one sentinel transition associated with one sentinel compound in each group of the two or more contiguous groups, wherein said at least one sentinel transition is selected as having the latest expected retention time in the group, using the processor, h) when the signal of at least one sentinel transition of a group is detected with the mass spectrometer, starting the monitoring of at least one sentinel transition in a next contiguous group while stopping the monitoring of the transitions of the preceding group, using the processor, i) optionally, generating a chromatogram or electropherogram, from the detection of transitions read from a predefined list with said mass spectrometer, using the processor, wherein each transition read from the predefined listed is associated to a peptide, wherein the predefined list of transitions comprises at least one transition that is associated to a peptide presenting a sequence selected from SEQ ID NO:1 to SEQ ID NO:423, and wherein the microorganism is identified according to the detection of said peptide(s).

2. The method according to claim 1, wherein the step of decomplexing the peptides mixture is performed by liquid chromatography or capillary electrophoresis.

3. The method according to claim 1, wherein the step of decomplexing the peptides mixture is carried out with a mobile phase comprising less than 40% of acetonitrile.

4. The method according to claim 1, wherein the mass spectrometer is a tandem mass spectrometer.

5. The method according to claim 1, wherein the mass spectrometer uses PRM (Parallel Reaction Monitoring), MRM (Multi Reaction Monitoring), DIA (Data Independent Acquisition), or SWATH MS (Sequential Window Acquisition of all THEoretical fragment ion spectra mass spectrometry).

6. The method according to claim 1, comprising a preliminary step of elimination of peptides that are not issued from the cleavage of ribosomal proteins by addition of a surfactant into said sample.

7. The method according to claim 1, wherein the two or more contiguous groups of transitions are associated with groups of peptides, each of the peptides being specific of a microorganism genus and/or species.

8. The method according to claim 1, wherein the cleavage of proteins is performed by digestion with the trypsin enzyme.

9. The method according to claim 1, wherein the predefined list of transitions comprises at least one transition that is associated to a peptide comprising between 6 and 20 amino-acids and that is decomplexed during step (b) with less than 40% of acetonitrile.

10. The method according to claim 1, wherein the sentinel compound is chosen from a group of compounds consisting of: peptides issued from step (a) of cleavage of proteins of the microorganism, peptides issued from autocleavage of the trypsin enzyme, peptides issued from the cleavage of proteins or peptides introduced into the sample, exogenous introduced peptides, and other compounds.

11. The method according to claim 1, wherein the sample is:

a biological sample obtained from a mammal, chosen from a group consisting of: blood, serum, lymph, mucus, stink, saliva, tracheobronchial aspirate, cerebrospinal fluid, and urine, or a sample chosen from a group consisting of: used waters, food, drink, soil sample, and surface sample.

12. A system for implementing the method according to claim 1, comprising a mass spectrometer coupled to a liquid separation device, the liquid separation device configured to decomplex a peptides mixture, the mass spectrometer configured to nebulize a liquid eluted from the separation device using an ion source in order to produce an ion current, and receive said ion current from the ion source and, for each cycle of a plurality of cycles, executing on the ion current a series of filtering steps for detecting a transition, said transition comprising a precursor ion and at least one fragment ion of said precursor ion, said transition being read from a predefined list of transitions, wherein for each transition of the series, the mass spectrometer selects and fragments a precursor ion of the each transition, and a processor configured to:

receive data concerning a plurality of transitions to be used to monitor a mixture of peptides using the processor, assign said plurality of transitions into two or more contiguous groups of transitions, into said predefined list of transitions using the processor, monitor at least one sentinel transition associated with one sentinel compound in each group of the two or more contiguous groups, wherein said at least one sentinel transition is selected as having the latest expected retention time in the group, using the processor, h) when the signal of at least one sentinel transition of a group is detected with the mass spectrometer, start the monitoring of at least one sentinel transition in a next contiguous group while stopping the monitoring of the transitions of the preceding group, using the processor, i) optionally, generate a chromatogram or electropherogram, from the detection of transitions read from a predefined list with said mass spectrometer, using the processor, wherein each transition read from the predefined listed is associated to a peptide, wherein the predefined list of transitions comprises at least one transition that is associated to a peptide presenting a sequence selected from SEQ ID NO: 1 to SEQ ID NO: 423, and wherein the microorganism is identified according to the detection of said peptide(s).

* * * * *